United States Patent
Chang et al.

(10) Patent No.: US 10,730,892 B2
(45) Date of Patent: Aug. 4, 2020

(54) HOMOALLYLAMINES AS FORMALDEHYDE-RESPONSIVE TRIGGERS

(71) Applicant: The Regents of the University of California, Oakland, CA (US)

(72) Inventors: Christopher J. Chang, Berkeley, CA (US); Thomas Francis Brewer, Berkeley, CA (US); Jefferson Chan, Urbana, IL (US)

(73) Assignee: The Regents of the University of California, Oakland, CA (US)

( * ) Notice: Subject to any disclaimer, the term of this patent is extended or adjusted under 35 U.S.C. 154(b) by 83 days.

(21) Appl. No.: 15/747,125

(22) PCT Filed: Aug. 18, 2016

(86) PCT No.: PCT/US2016/047580
§ 371 (c)(1),
(2) Date: Jan. 23, 2018

(87) PCT Pub. No.: WO2017/034927
PCT Pub. Date: Mar. 2, 2017

(65) Prior Publication Data
US 2018/0215773 A1 Aug. 2, 2018

Related U.S. Application Data

(60) Provisional application No. 62/208,305, filed on Aug. 21, 2015.

(51) Int. Cl.
| | | |
|---|---|---|
| *C07F 7/08* | (2006.01) | |
| *C09K 11/06* | (2006.01) | |
| *G01N 1/30* | (2006.01) | |
| *C12Q 1/26* | (2006.01) | |
| *G01N 21/76* | (2006.01) | |
| *G01N 15/14* | (2006.01) | |

(52) U.S. Cl.
CPC ............ *C07F 7/0816* (2013.01); *C09K 11/06* (2013.01); *C12Q 1/26* (2013.01); *G01N 1/30* (2013.01); *G01N 21/76* (2013.01); *C09K 2211/104* (2013.01); *C09K 2211/1007* (2013.01); *C09K 2211/1018* (2013.01); *C09K 2211/1029* (2013.01); *G01N 15/1459* (2013.01)

(58) Field of Classification Search
None
See application file for complete search history.

(56) References Cited

U.S. PATENT DOCUMENTS

2011/0065105 A1    5/2011   Dietrich et al.
2011/0136130 A1*   6/2011   Gniewek .............. G01N 33/581
                                                            435/6.19

FOREIGN PATENT DOCUMENTS

CN            104193672 A         12/2014

OTHER PUBLICATIONS

Weglarz-Tomczak et al. Biochimie (2013) 95: 419-428 (Year: 2013).*
Wang et al. Tetrahedron (2005) 61: 8465-8474 (Year: 2005).*
Sun et al. Adv. Functional Mat (2005) 15(5): 818-822 (Year: 2005).*
Li, et al.; "Chromo-fluorogenic detection of aldehydes with a rhodamine based sensor featuring an intramolecular deoxylactam"; Org. Biomol. Chem.; vol. 9, pp. 7652-7654 (2011).
Roth, et al.; "A Reaction-Based Fluorescent Probe for Imaging of Formaldehyde in Living Cells"; The Journal of the American Chemical Society; vol. 137, pp. 10890-10893 (2015).
Song, et al.; "A tailor designed fluorescent 'turn-on' sensor of formaldehyde based on the BODIPY motif"; Tetrahedron Letters; vol. 53, pp. 4913-4916 (2012).
Zhou, et al.; "HCHO-reactive molecule with dual-emission-enhancement property for quantitatively detecting HCHO in near 100% water solution"; Sensors and Actuators B: Chemical; vol. 209, pp. 664-669 (2015).

* cited by examiner

*Primary Examiner* — Susan M Hanley
(74) *Attorney, Agent, or Firm* — Bozicevic, Field & Francis LLP; Paula A. Borden

(57) ABSTRACT

Probes for formaldehyde (FA) including a homoallylamine trigger group attached to a detectable moiety are provided. Aspects of the probes include luminogenic or fluorogenic probes, such as a probe including a quencher in energy-receiving proximity to a fluorophore. Also provided are methods of using the probes for sensitive and bio orthogonal detection of FA in a sample. Aspects of the methods include selectively reacting the probe with the formaldehyde in the sample to release (e.g., via a 2-aza-Cope rearrangement) a reporter group comprising a detectable moiety. Aspects of the methods detecting formaldehyde in a cell, tissue, organ or fluid in a subject. Also provided are compositions and kits including the subject probes that find use in practicing various embodiments of the subject methods.

17 Claims, 38 Drawing Sheets

ER-Tracker · LysoTracker · MitoTracker

ER-Tracker · LysoTracker · MitoTracker

FIG. 32

| | Pearson's Coefficient |
|---|---|
| ER-Tracker Green | 0.51 ± 0.02 |
| BODIPY Fl $C_5$-Ceramide | 0.60 ± 0.05 |
| LysoTracker Green DND-26 | 0.56 ± 0.06 |
| MitoTracker Green | 0.59 ± 0.04 |
| Hoechst 33342 | 0.09 ± 0.04 |

… 1 …

HOMOALLYLAMINES AS FORMALDEHYDE-RESPONSIVE TRIGGERS

CROSS-REFERENCE

This application claims the benefit of U.S. Provisional Patent Application No. 62/208,305, filed Aug. 21, 2015, which application is incorporated herein by reference in its entirety.

INTRODUCTION

Formaldehyde (FA), the simplest aldehyde, is a reactive carbonyl species (RCS) that has long been known as a human toxin and carcinogen that is released into the environment from natural (e.g., biomass combustion, solar degradation of humic substances, vegetation and microbe emissions) as well as anthropogenic (e.g., FA production and fumigation, vehicle exhaust, etc.) sources. At the same time, FA is also produced endogenously in the body by demethylase and oxidase enzymes that regulate epigenetics and metabolism, such as lysine-specific demethylase 1 (LSD1), JmjC domain-containing proteins and semicarbazide-sensitive amine oxidase. Active degradation by formaldehyde dehydrogenase/S-nitrosoglutathione reductase and aldehyde dehydrogenase 2 enzymes gives physiological FA levels ranging from 100 µM in blood to 400 µM intracellularly. Elevations of FA and related RCS are implicated in a variety of disease pathologies, including various cancers, neurodegenerative diseases, diabetes, and chronic liver and heart disorders.

Methods for monitoring FA within intact, living biological specimens include use of radiometry, gas chromatography, selected ion flow tube mass spectrometry, and high performance liquid chromatography, which offer high sensitivity and selectivity but involve sample processing and/or destruction of intact specimens.

SUMMARY

Probes for formaldehyde (FA) including a homoallylamine trigger group attached to a detectable moiety are provided. Aspects of the probes include luminogenic or fluorogenic probes, such as a probe including a quencher in energy-receiving proximity to a fluroophore. Also provided are methods of using the probes for sensitive and bioorthogonal detection of FA in a sample. Aspects of the methods include selectively reacting the probe with the formaldehyde in the sample to a release (e.g., via a 2-aza-Cope rearrangement) a reporter group comprising a detectable moiety. Aspects of the methods detecting formaldehyde in a cell, tissue, organ or fluid in a subject. Also provided are compositions and kits including the subject probes that find use in practicing various embodiments of the subject methods.

Aspects of the present disclosure include a formaldehyde probe having the formula:

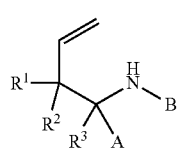

wherein: $R^1$, $R^2$, $R^3$, A and B are each independently selected from the group consisting of hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy and an amido; and wherein A comprises a detectable moiety; wherein B optionally comprises a quencher; and wherein A and B are optionally cyclically linked.

In some embodiments, the probe is luminogenic. In some embodiments, the probe is fluorogenic. In some embodiments, A comprises a fluorophore and B comprises a quencher that is in energy-receiving proximity to the fluorophore. In some embodiments, the probe has the formula:

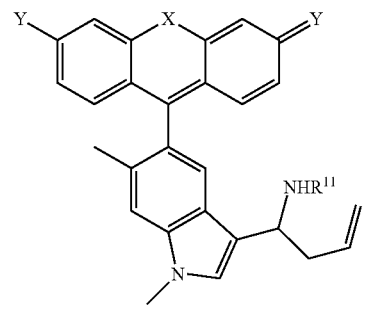

wherein: X is selected from the group consisting of O, $SiR_2$, $CR_2$, $SnR_2$, $BF_2$, S, Se, Te, $PO_2H$, $AsO_2H$, wherein each R is independently H or an alkyl (e.g., methyl); each Y is independently selected from =O, —OH, —$NH_2$, =NH, —NR'R", =$N^+$R'R", wherein R' and R" are independently an alkyl or a substituted alkyl, or R' and R" are cyclically linked to form, with the N to which they are attached, a five or six-membered heterocycle or substituted heterocycle; and $R^{11}$ is selected from the group consisting of hydrogen, alkyl, substituted alkyl, alkoxy, substituted alkoxy, aralkyl, substituted aralkyl, aryl, substituted aryl, heteroaryl and substituted heteroaryl, and wherein $R^{11}$ optionally comprises the quencher.

In some embodiments, each Y is independently selected from one of the following structures:

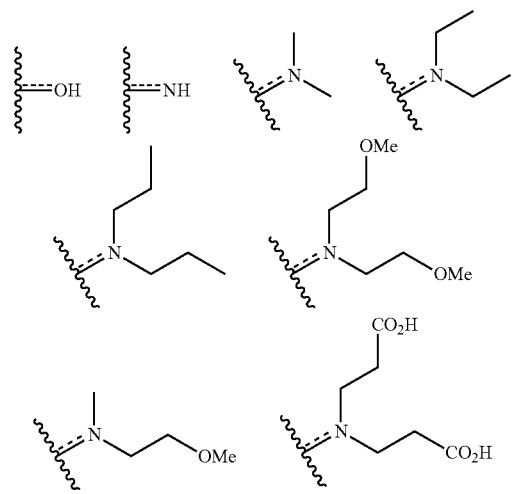

3

-continued

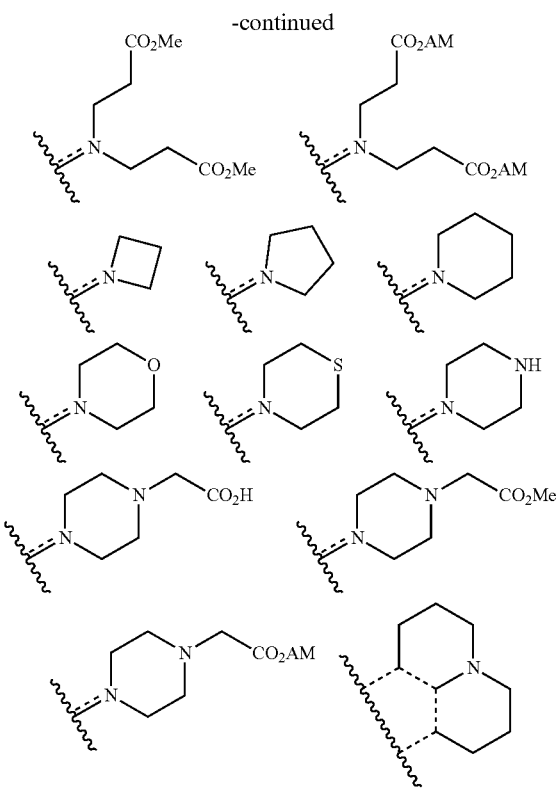

wherein when Y is connected to the probe via a double bond, it can be positively charged; and
R¹¹ is selected from one of the following structures:

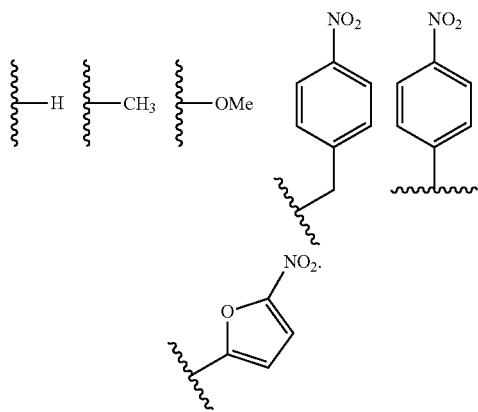

In some embodiments, the probe has the formula:

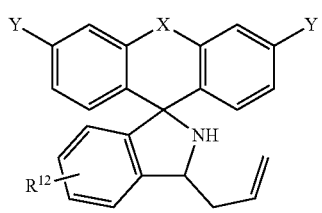

wherein: X is selected from the group consisting of O, SiR$_2$, CR$_2$, SnR$_2$, BF$_2$, S, Se, Te, PO$_2$H, AsO$_2$H, wherein each R is independently H or an alkyl; each Y is independently selected from =O, —OH, —NH$_2$, =NH, —NR'R", =N$^+$R'R", wherein R' and R" are independently an alkyl or a substituted alkyl, or R' and R" are cyclically linked to form, with the N to which they are attached, a five or six membered heterocycle or substituted heterocycle; and R¹² is hydrogen, carboxy, an ester, an amido, an alkyl-amido or a substituted alkyl-amido, wherein R¹² optionally comprises a chemoselective tag.

In some embodiments, each Y is independently selected from one of the following structures:

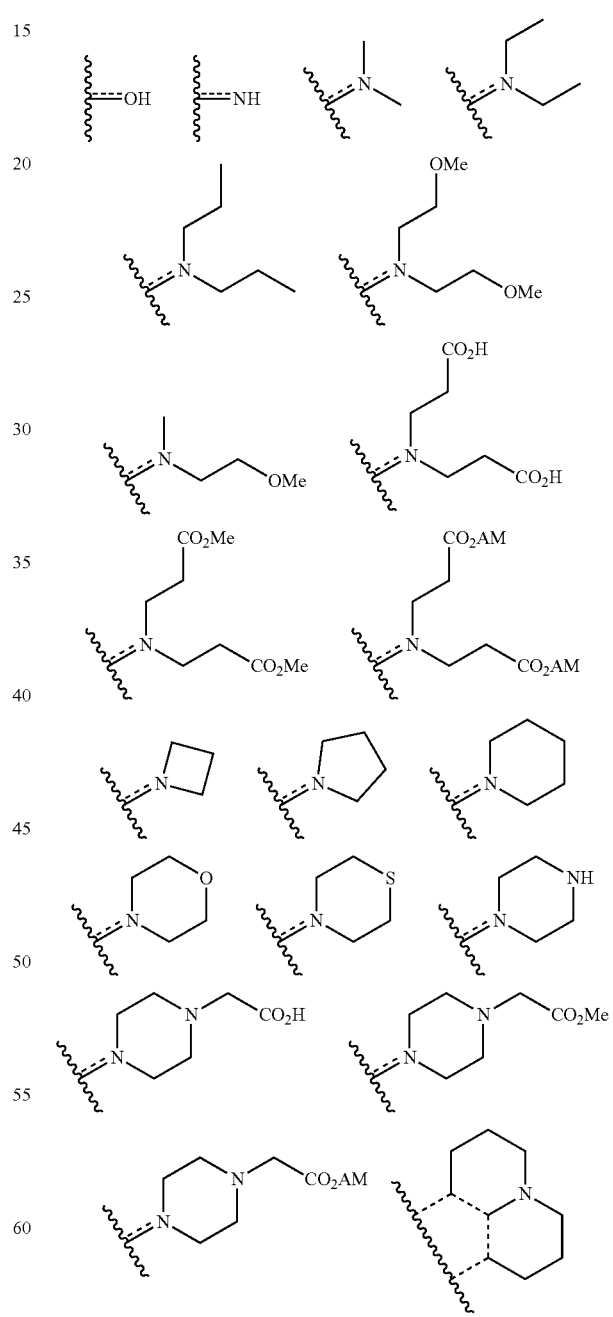

wherein when Y is connected to the probe via a double bond, it can be positively charged; and $R^{12}$ is selected from one of the following structures:

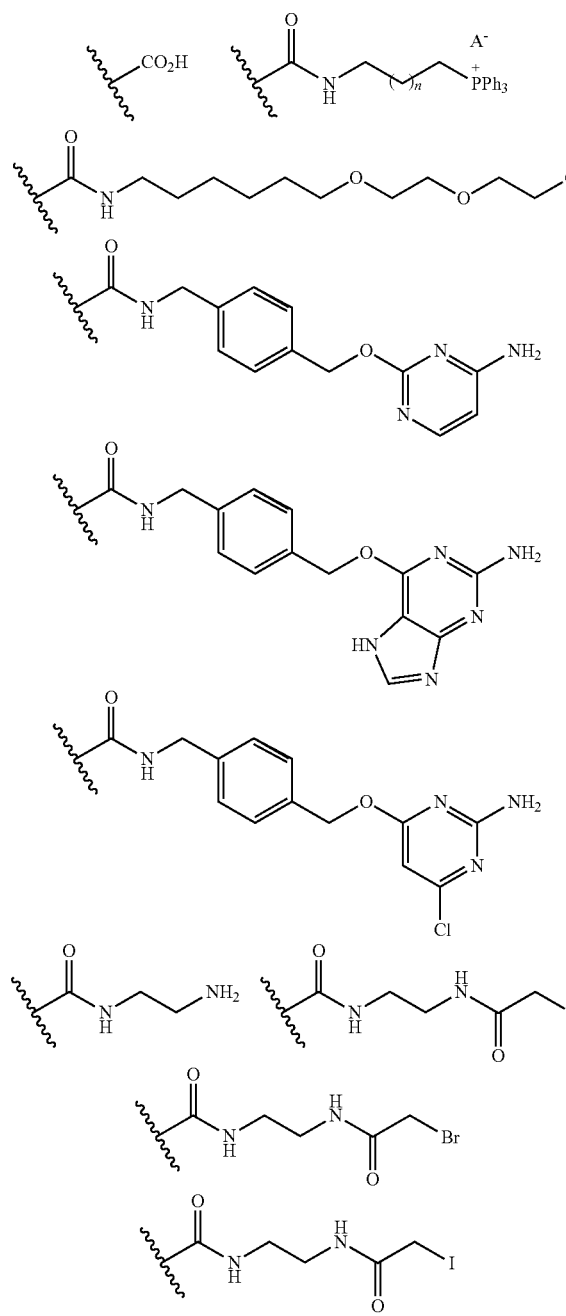

wherein n is 0, 1, 2, 3, 4, 5 or 6; and A is a counteranion.

In some embodiments, A has the formula:

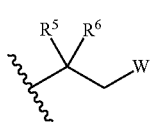

wherein W comprises a detectable moiety selected from the group consisting of luciferin, a substituted luciferin, an aminoluciferin, coelenterazine, a modified coelenterazine, a xanthene dye, a xanthene analog, a fluorescein dye, or a rhodamine dye; and $R^5$ and $R^6$ are independently selected from the group consisting of hydrogen, an alkyl, a substituted alkyl, an aryl, a substituted aryl, a heteroaryl, a substituted heteroaryl, a halogen, a cyano, an azido, an alkoxy, a substituted alkoxy, a hydroxyl, a carboxy and an amido.

In some embodiments, the probe has one of the following formulae:

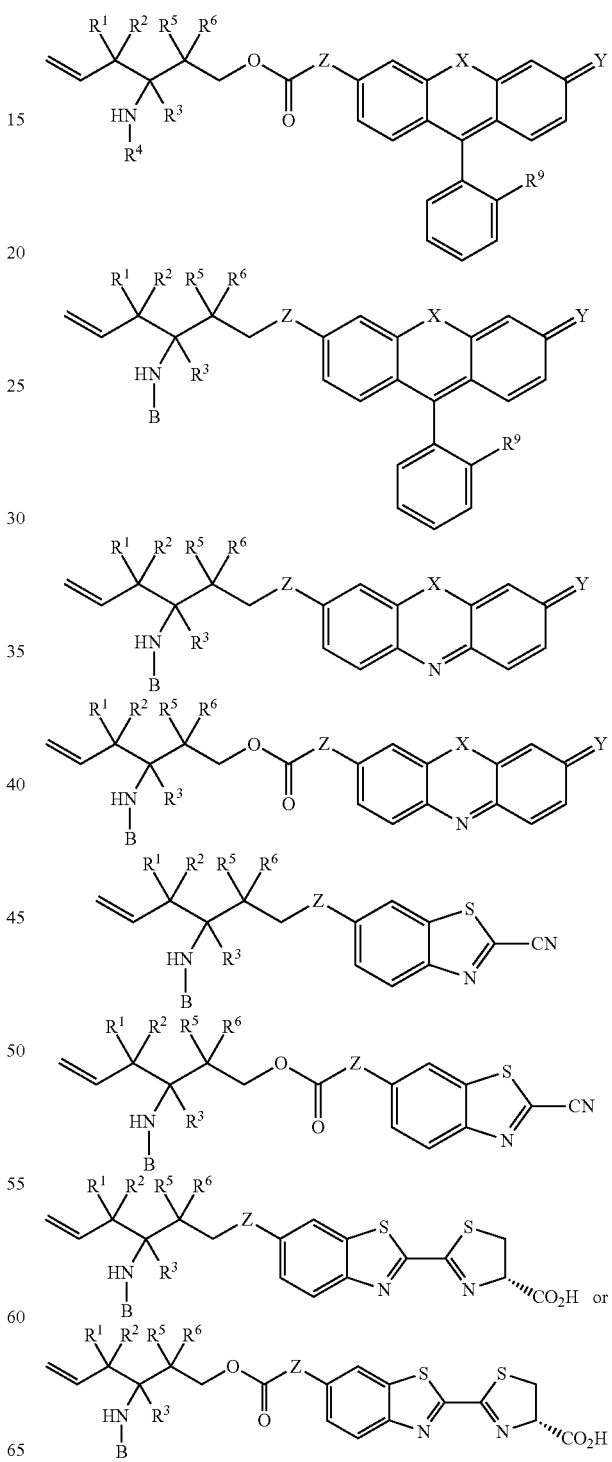

wherein: Z is O, S, NH or NR' wherein R' is an alkyl or substituted alkyl; $R^9$ is selected from the group consisting of hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy, a carboxy ester, and an amido; and X and Y are as defined above.

In some embodiments, A is the detectable moiety. In some embodiments, the probe has one of the following structures:

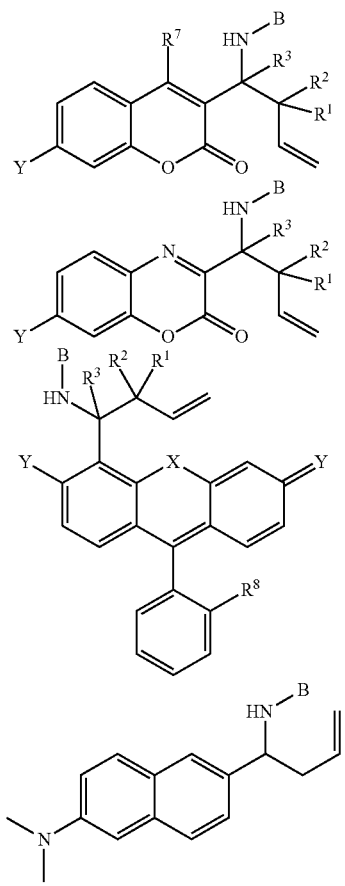

wherein: $R^1$-$R^3$ and Y are as defined above; $R^7$ and $R^8$ are independently selected from the group consisting of hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy, a carboxy ester and an amido; and B is selected from the group consisting of hydrogen, alkyl, substituted alkyl, hydroxy, alkoxy, substituted alkoxy, aryl, substituted aryl, aralkyl, substituted aralkyl, heterarylalkyl, and substituted heterarylalkyl.

In some embodiments, each Y is independently selected from one of the following structures:

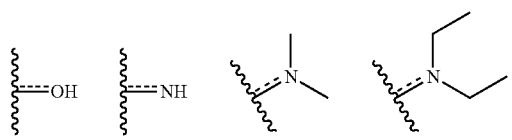

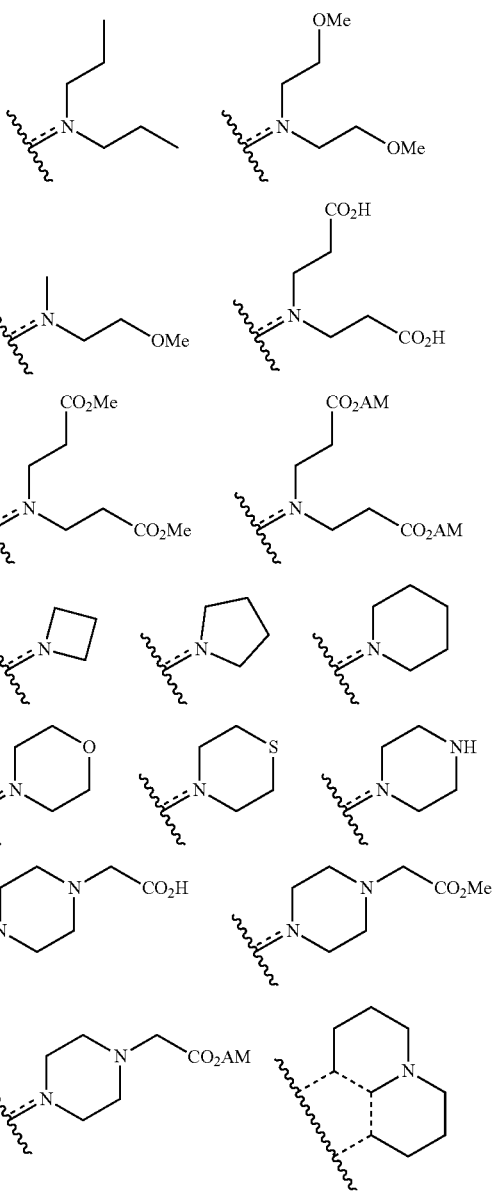

wherein when Y is connected to the probe via a double bond, it can be positively charged; B is selected from one of the following structures:

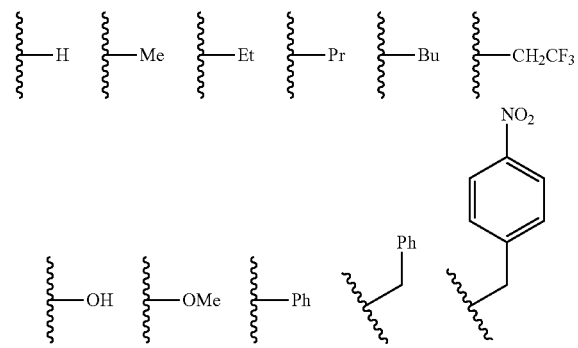

-continued

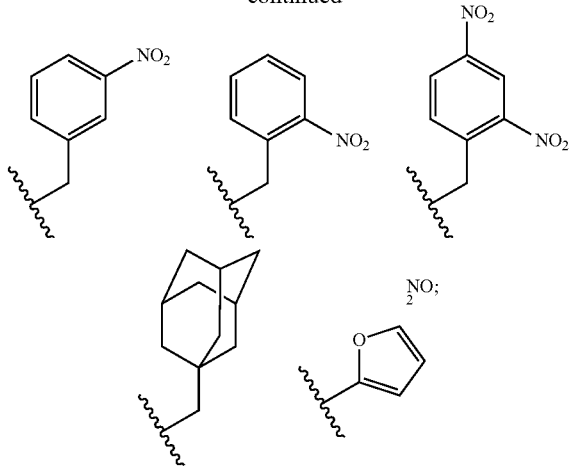

and $R^1$, $R^2$, $R^3$, $R^7$ and $R^8$ are independently selected from one of the following structures:

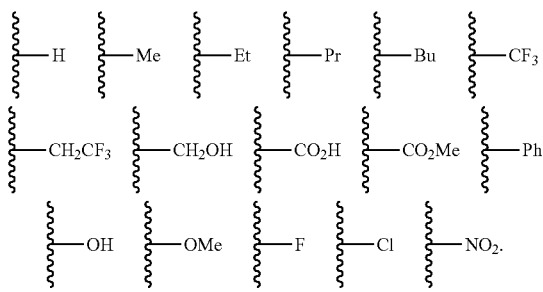

Aspects of the present disclosure include a method of detecting formaldehyde in a sample. In some embodiments, the method comprises: contacting a sample comprising formaldehyde with a probe of any one of claims 1-13 thereby selectively reacting the probe with the formaldehyde in the sample to a release a reporter group comprising a detectable moiety; and detecting the detectable moiety thereby providing for detection of the formaldehyde in the sample. In some embodiments, the selectively reacting comprises performing a 2-aza-Cope rearrangement on the contacted probe. In some embodiments, the reporter group has the formula:

wherein A comprises a fluorophore, a chromophore or a luminophore.

In some embodiments, A comprises a fluorophore. In some embodiments, the detecting comprises fluorescently imaging the sample. In some embodiments, the method further comprises analyzing the level of formaldehyde in the sample. In some embodiments, the method further comprises analyzing the activity of an enzyme endogenous to the sample. In some embodiments, the enzyme is lysine-specific demethylase 1 (LSD1) and the sample comprises breast cancer cells. In some embodiments, the sample is a biological sample comprising a cell, a cell lysate, a tissue, or a fluid. In some embodiments, the sample is a biological sample that is in vivo.

Aspects of the present disclosure include a method of detecting formaldehyde in a cell, tissue, organ or fluid in a living subject. In some embodiments, the method comprises: administering to the subject a probe of any one of claims 1-13 thereby selectively reacting the probe with the formaldehyde in the sample to a release a reporter group comprising a detectable moiety; and detecting the detectable moiety in the cell, tissue, organ or fluid, thereby providing for detection of the formaldehyde. In some embodiments, the subject is a human. In some embodiments, the cell, tissue, or organ is a diseased cell, tissue, or organ. In some embodiments, the cell is a cancer cell.

Aspects of the present disclosure include a composition, comprising: a probe (e.g., as described herein); and a reactive carbonyl species; contained in a biological sample. Aspects of the present disclosure include a kit comprising: a probe (e.g., as described herein); and one or more components selected from a reactive carbonyl species, a cell, an enzyme and instructions for use.

BRIEF DESCRIPTION OF THE DRAWINGS

FIG. 6A, fluorescence response of 1 µM FP1 to 5 mM FA in PBS buffer (pH 7.4) at 37° C. FP1 was excited at 633 nm and the emission was collected between 640 and 750 nm. Time points on graph are 0, 30, 60, 90, 120, 150, and 180 min. FIG. 6B, fluorescence response of 1 µM FP1 to biologically relevant aldehydes, reactive sulfur species, and hydrogen peroxide. Bars represent normalized fold-changes in response to treatment with each analyte listed at 1 mM for 3 hrs.

FIG. 8B, 1 mM; FIG. 8C, 2.5 mM; and FIG. 8D, 5 mM FA for 3 hrs at 37° C. with the 633 nm HeNe laser. Scale bar represents 20 µm. Pseudo-coloring represents intensity distribution from highest intensity indicated by white to the lowest intensity designated by black. FIG. 8E shows quantification of imaging data.

FIG. 11B, 1 mM; FIG. 11C, 2.5 mM; and FIG. 11D, 5 mM FA at 37° C. for 3 hrs with the 633 nm HeNe laser. Scale bar represents 20 µm. Pseudo-coloring represents intensity distribution from highest intensity indicated by white to the lowest intensity designated by black. FIG. 11E shows quantification of imaging data.

FIG. 14A, Flow cytometry analysis of HEK293TN cells. Cells were stained with a solution of 2 µM FP1 in DMEM for 8 min, rinsed with fresh DMEM and then treated with a) a DMEM vehicle control; b) 1 mM FA, 1 hr incubation; c) 1 mM FA, 2 hrs incubation; d) 1 mM FA, 3 hrs incubation; e) a DMEM vehicle control; f) 2.5 mM FA, 1 hr incubation; g) 2.5 mM FA, 2 hrs incubation; h) 2.5 mM FA, 3 hrs incubation; i) a DMEM vehicle control; j) 5 mM FA, 1 hr incubation; k) 5 mM FA, 2 hrs incubation; and l) 5 mM FA, 3 hrs incubation. FIG. 14B, Flow cytometry analysis of NS1 cells. Cells were stained with a solution of 2 µM FP1 in Ham's F-12K media for 8 min, rinsed with fresh media and then treated with a) a DMEM vehicle control; b) 1 mM FA, 1 hr incubation; c) 1 mM FA, 2 hrs incubation; d) 1 mM FA, 3 hrs incubation; e) a DMEM vehicle control; f) 2.5 mM FA, 1 hr incubation; g) 2.5 mM FA, 2 hrs incubation; h) 2.5 mM FA, 3 hrs incubation; i) a DMEM vehicle control; j) 5 mM FA, 1 hr incubation; k) 5 mM FA, 2 hrs incubation; and l) 5 mM FA, 3 hrs incubation.

FIG. 17A, Confocal microscopy images of co-localization experiments using HEK293TN cells. Cells were co-incubated for 5 min with 2 µM FPI and 1 µM of each tracker in serum-free DMEM, then washed with dye-free DMEM and imaged. Top row of images show fluorescent signal from FP1 obtained by irradiation with the 633 nm HeNe laser. Bottom row of images show fluorescent signal from ER-Tracker Green, LysoTracker, and MitoTracker Green FM obtained by irradiation with the 488 nm laser. Scale bar represents 20 µm. FIG. 17B, Same as above but for NS1 cells.

FIG. 24A depicts the fluorescence response of 10 μM FAP-1 to 100 μM FA. Data were acquired at 37° C. in 20 mM PBS (pH 7.4) with excitation at $\lambda_e$=645 nm. Emission was collected between 655 and 750 nm. Time points represent 0, 20, 45, 60, 90, and 120 (lighter colored trace) min after addition of 100 μM FA. FIG. 24B depicts the fluorescence response of 10 μM FAP-1 to biologically relevant RCS and related molecules. Bars represent relative emission from 655-700 nm at 0, 20, 45, 60, 90, and 120 (black) min after addition. Data shown are for 100 μM of all species unless otherwise denoted. Data were acquired in 20 mM PBS (pH 7.4) at 37° C. with excitation at $\lambda_e$=645 nm. Legend: (1) PBS; (2) FA; (3) acetaldehyde; (4) 4-hydroxynonenal; (5) dehydroascorbate; (6) glucose, 1 mM; (7) glucosone; (8) oxaloacetate; (9) pyruvate; (10) H$_2$O$_2$; (11) glutathione, 5 mM; (12) methylglyoxal; (13) methylglyoxal, 10 μM.

FIG. 28A-28B depict confocal microscopy images of: FIG. 28A, Confocal microscopy of FA detection in live HEK293T cells using FAP-1. Cells were treated with 10 μM FAP-1 in BSS for 30 min at 37° C., followed by an exchange into fresh BSS and addition of varying FA concentrations. Images are taken 30 min after addition of (a) vehicle, (b) 200 μM FA, (c) 500 μM FA, and (d) 1 mM FA. (e) Bright-field image of cells in (d) overlaid with image of 1 μM Hoechst 33342. Scale bar represents 50 μm in all images. (f) Mean fluorescence intensities of HEK293T cells treated with varying concentrations of FA for 30 min relative to mean fluorescence intensity before FA addition; error bars denote SEM, n=3. *P<0.005, **P<0.0005. FIG. 28B, Confocal microscopy of FAP-1 in TCP- and GSK-LSD1-treated MCF7 cells. Cells were pretreated with inhibitor (TCP or GSK-LSD1) for 20 h, followed by exchange into fresh BSS with 10 μM FAP-1 and incubation for 60 min at 37° C. Images are of cells treated with (a) vehicle, (b) 20 μM TCP, (c) 1 μM GSK-LSD1. (d) and (e) Bright-field images of cells in (b) and (c), respectively, overlaid with images of 1 μM Hoechst 33342. Scale bar represents 50 μm in all images. (f) Mean fluorescence intensities of MCF7 cells treated with (1) vehicle (2) 20 μM TCP, and (3) 1 μM GSK-LSD1. Error bars denote SEM, n=6. *P<0.005

FIG. 30A, HEK293T cells were incubated with indicated concentrations of FA in BSS at 37° C. for 30 min, then exchanged into PBS containing 3 μM PI and incubated for 10 min before flow cytometry. FIG. 30B, MCF7 cells were treated with indicated concentrations of inhibitor in DMEM supplemented with 10% FBS for 20 h at 37° C. in 5% CO$_2$, then exchanged into PBS containing 3 μM PI and incubated for 10 min before flow cytometry. Error bars denote SEM, n=3.

FIG. 32 depicts a table showing the quantification of colocalization studies. Pearson's coefficients were calculated using the JACoP plugin for ImageJ and averaged across 4 separate fields of cells. Error represents the standard deviation between different fields of cells.

DEFINITIONS

Figure 1:
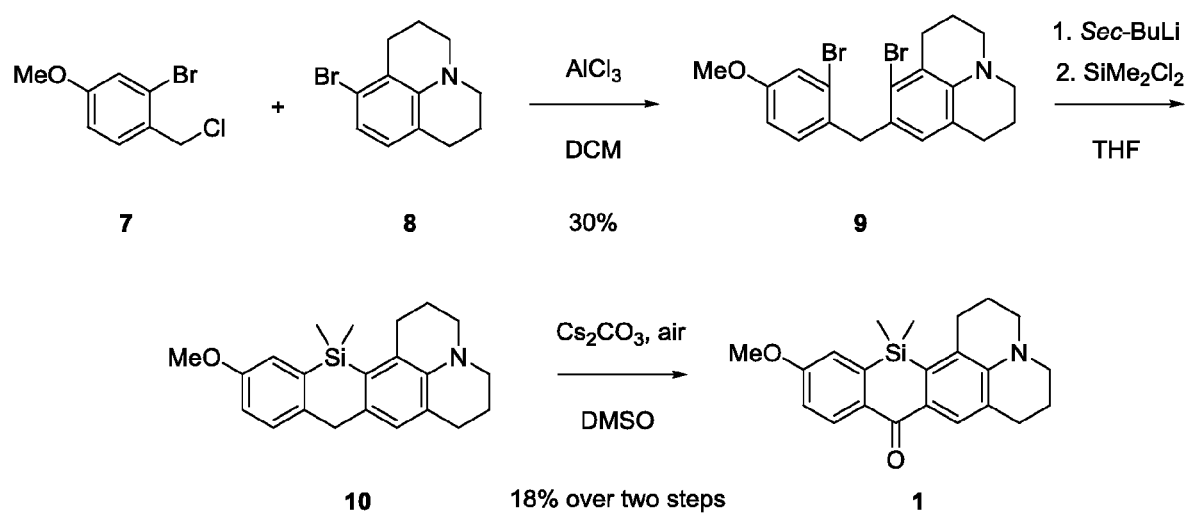
FIG. 1 depicts a schematic showing the synthesis of Si-xanthone.

The following terms have the following meanings unless otherwise indicated. Any undefined terms have their art recognized meanings.

"Alkyl" refers to monovalent saturated aliphatic hydrocarbyl groups having from 1 to 10 carbon atoms and such as 1 to 6 carbon atoms, or 1 to 5, or 1 to 4, or 1 to 3 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—).

The term "substituted alkyl" refers to an alkyl group as defined herein wherein one or more carbon atoms in the alkyl chain have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R is alkyl group as defined herein and R is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O-alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$— alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$— alkyl, —SO$_2$-substituted alkyl, —SO$_2$-aryl, and —SO$_2$-heteroaryl.

"Alkynyloxy" refers to the group O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, heteroaryl, heterocyclic, and substituted heterocyclic are as defined herein. For example, acyl includes the "acetyl" group $CH_3C(O)$—

"Acylamino" refers to the groups $NR^{20}C(O)$alkyl, —$NR^{20}C(O)$substituted alkyl, N $R^{20}C(O)$cycloalkyl, —$NR^{20}C(O)$substituted cycloalkyl, —$NR^{20}C(O)$cycloalkenyl, —$NR^{20}C(O)$substituted cycloalkenyl, —$NR^{20}C(O)$alkenyl, —$NR^{20}C(O)$substituted alkenyl, —$NR^{20}C(O)$alkynyl, —$NR^{20}C(O)$substituted alkynyl, —$NR^{20}C(O)$aryl, —$NR^{20}C(O)$substituted aryl, —$NR^{20}C(O)$heteroaryl, —$NR^{20}C(O)$substituted heteroaryl, —$NR^{20}C(O)$heterocyclic, and —$NR^{20}C(O)$substituted heterocyclic, wherein $R^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —$C(O)NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group $NR^{21}C(O)NR^{22}R^{23}$ where $R^{21}$, $R^{22}$, and $R^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group $SO_2NR^{21}R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where $R^{21}$ and $R^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group $NR^{21}SO_2R^{22}$, wherein $R^{21}$ and $R^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where $R^{21}$ and $R^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO—heteroaryl, —$SO_2$-alkyl, —$SO_2$-substituted alkyl, —$SO_2$-aryl, —$SO_2$-heteroaryl and trihalomethyl.

"Aryloxy" refers to the group O-aryl, wherein aryl is as defined herein, including, by way of example, phenoxy, naphthoxy, and the like, including optionally substituted aryl groups as also defined herein.

"Amino" refers to the group $NH_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group $N_3$.

"Carboxyl," "carboxy" or "carboxylate" refers to $CO_2H$ or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-cycloalkenyl, —O—C(O)O-substituted cycloalkenyl, —O—C(O)O— heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO— heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$— substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to O-cycloalkyl.

"Cycloalkenyloxy" refers to O-cycloalkenyl.

"Halo" or "halogen" refers to fluoro, chloro, bromo, and iodo.

"Hydroxy" or "hydroxyl" refers to the group OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO— alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or SO$_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and fused heterocycle.

"Heterocyclyloxy" refers to the group O-heterocyclyl.

The term "heterocyclylthio" refers to the group heterocyclic-S—.

The term "heterocyclene" refers to the diradical group formed from a heterocycle, as defined herein.

The term "hydroxyamino" refers to the group —NHOH.

"Nitro" refers to the group NO$_2$.

"Oxo" refers to the atom (=O).

"Sulfonyl" refers to the group SO$_2$-alkyl, SO$_2$-substituted alkyl, SO$_2$-alkenyl, SO$_2$-substituted alkenyl, SO$_2$-cycloalkyl, SO$_2$-substituted cycloalkyl, SO$_2$-cycloalkenyl, SO$_2$-substituted cylcoalkenyl, SO$_2$-aryl, SO$_2$-substituted aryl, SO$_2$-heteroaryl, SO$_2$-substituted heteroaryl, SO$_2$-heterocyclic, and SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-SO$_2$—, phenyl-SO$_2$—, and 4-methylphenyl-SO$_2$—.

"Sulfonyloxy" refers to the group OSO$_2$-alkyl, OSO$_2$-substituted alkyl, OSO$_2$-alkenyl, OSO$_2$-substituted alkenyl, OSO$_2$-cycloalkyl, OSO$_2$-substituted cycloalkyl, OSO$_2$-cycloalkenyl, OSO$_2$-substituted cylcoalkenyl, OSO$_2$-aryl, OSO$_2$-substituted aryl, OSO$_2$-heteroaryl, OSO$_2$-substituted heteroaryl, OSO$_2$-heterocyclic, and OSO$_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.

"Thioxo" or the term "thioketo" refers to the atom (=S).

"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —SO$_2$R$^{70}$, —SO$_2$O$^-$M$^+$, —SO$_2$OR$^{70}$, —OSO$_2$R$^{70}$, —OSO$_2$O$^-$M$^+$, —OSO$_2$OR$^{70}$, —P(O)(O$^-$)$_2$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, OC(O)O$^-$M$^+$, —OC(O)OR$^{70}$, —OC(S)OR$^{70}$, —NR$^{70}$C(O) R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$) R$^{70}$ and —NR$^{70}$C(NR$^{70}$)NR$^{80}$R$^{80}$ where R$^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or C$_1$-C$_3$ alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR$^{80}$R$^{80}$ is meant to include —NH$_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —S$^-$M$^+$, —NR$^{80}$R$^{80}$, trihalomethyl, —CF$_3$, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{2-}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —OC$_2$$^-$M$^+$, —CO$_2$R$^{70}$, —C(S) OR$^{70}$, —C(O)NR$^{80}$R$^{80}$, —C(NR$^{70}$)NR$^{80}$R$^{80}$, —OC(O)R$^{70}$, —OC(S)R$^{70}$, —OCO$_2$R$^{70}$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the groups disclosed with respect to the individual terms herein, substituent groups for hydrogens on nitrogen atoms in "substituted" heteroalkyl and cycloheteroalkyl groups are, unless otherwise specified, —R$^{60}$, —O$^-$M$^+$, —OR$^{70}$, —SR$^{70}$, —S$^-$M$^+$, —NR$^{80}$R$^{80}$, trihalomethyl, —CF$_3$, —CN, —NO, —NO$_2$, —S(O)$_2$R$^{70}$, —S(O)$_2$O$^-$M$^+$, —S(O)$_2$OR$^{70}$, —OS(O)$_2$R$^{70}$, —OS(O)$_2$O$^-$M$^+$, —OS(O)$_2$OR$^{70}$, —P(O)(O)$_2$(M$^+$)$_2$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)OR$^{70}$, —OC(S)OR$^{70}$, —NR$^{70}$C(O)R$^{70}$, —NR$^{70}$C(S)R$^{70}$, —NR$^{70}$C(O)OR$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$, where R$^{60}$, R$^{70}$, R$^{80}$ and M$^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N═C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient," "subject," and "individual" refer to human and non-human subjects, e.g., mammalian subjects. An individual is in some cases a human. In some cases, an individual is a non-human mammal. In some cases, an individual is a non-human primate. In some cases, an individual is a rodent (e.g., a mouse, a rat). In some cases, an individual is a lagomorph (e.g., a rabbit).

As used herein, the term "linker" or "linkage" refers to a linking moiety that connects two groups and, in some cases, has a backbone of 100 atoms or less in length. A linker or linkage may be a covalent bond that connects two groups or a chain of between 1 and 100 atoms in length, for example a chain of 1, 2, 3, 4, 5, 6, 8, 10, 12, 14, 16, 18, 20, 30, 40 or 50 carbon atoms or less in length, where the linker may be linear, branched, cyclic or a single atom. In certain cases, one, two, three, four or five or more carbon atoms of a linker backbone may be optionally substituted with a sulfur, nitrogen or oxygen heteroatom. The bonds between backbone atoms may be saturated or unsaturated, and in some cases not more than one, two, or three unsaturated bonds are present in a linker backbone. The linker may include one or more substituent groups, for example with an alkyl, aryl or alkenyl group. A linker may include, without limitations, polyethylene glycol (PEG), including modified PEG groups; ethers, thioethers, tertiary amines, alkyls, which may be straight or branched, e.g., methyl, ethyl, n-propyl, 1-methylethyl (iso-propyl), n-butyl, n-pentyl, 1,1-dimethylethyl (t-butyl), and the like. The linker backbone may include a cyclic group, for example, an aryl, a heterocycle or a cycloalkyl group, where 2 or more atoms, e.g., 2, 3 or 4 atoms, of the cyclic group are included in the backbone. A linker may be cleavable or non-cleavable.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a probe" includes a plurality of such probes and reference to "the probe" includes reference to one or more probes and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides probes and methods for using the same. Also provided are compositions and kits including the subject probes that find use in the subject methods. Embodiments of each are described in more detail in the sections below.

Probes

The present disclosure provides probes for reactive carbonyl species. By "probe" is meant a compound that interacts with an analyte of interest to provide a measurable or detectable change in a property of interest. The measurable or detectable change may be a fluorogenic, colorimetric or bioluminescent response to interaction with the analyte (e.g., the reactive carbonyl species). As used herein, "reactive carbonyl species" refers to a naturally occurring molecule that includes a ketone or aldehyde functional group which is capable of reaction with a subject probe. Reactive carbonyl species of interest include, but are not limited to, formaldehyde, 4-hydroxynonenal, dehydroascorbate, glucosone, oxaloacetate, methylglyoxal, acetaldehyde, pyruvate, and glucose. In certain embodiments, the reactive carbonyl species is formaldehyde and the subject probe is selective for formaldehyde over other reactive carbonyl species that may be present in a sample of interest.

The subject probes include a homoallylamine trigger group which is configured for selective reaction in a sample with a reactive carbonyl species of interest. As used herein, a "homoallylamine trigger group" refers to a chemical group including a substituted homoallylamine (e.g., a group having the general formula $CH_2$=CH—$CR_2$—$CR_2$—NHR, where each R is independently H or any convenient substituent group, e.g., as described herein). In some embodiments, the probes include a homoallylamine trigger group that selectively reacts with formaldehyde to produce a Schiff base adduct that undergoes further rearrangement and/or reaction to release two products, e.g., an amino product and a keto or aldehyde product (see e.g., Scheme 1). The subject probes take advantage of the resulting rearrangement and cleavage of the homoallylamine trigger group to produce a detectable change in a property of the probe via its conversion to reaction products. In some cases, selective reaction of the probe with formaldehyde proceeds according to the exemplary reaction set forth in scheme 1.

Scheme 1

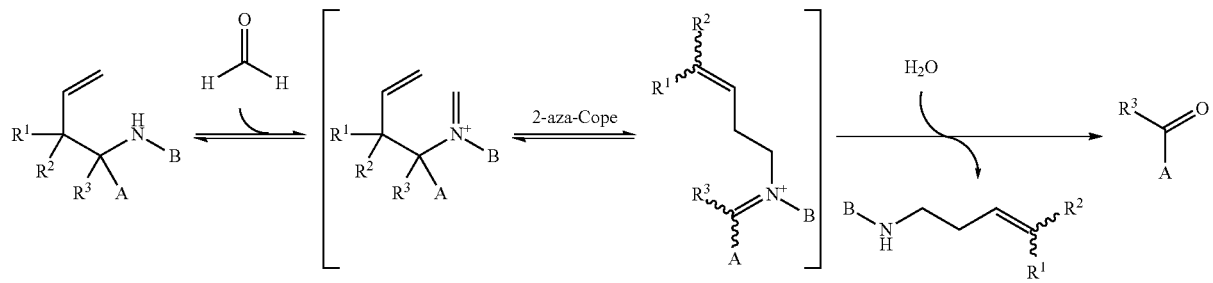

where $R^1$-$R^3$, A and B are any convenient substituent groups, where at least one of A and B includes a detectable moiety, such as a fluorophore, a chromophore, a luminophore, a quencher or a bioluminescent group.

It is understood that other configurations of the probes described herein are possible that can also provide for a desirable and detectable change of a property of the probe in response to reaction of a homoallylamine trigger group with formaldehyde.

In some embodiments, the probe has the formula (I):

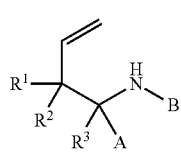

(I)

wherein: $R^1$, $R^2$, $R^3$, A and B are each independently selected from the group consisting of hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy and an amido; and wherein A comprises a detectable moiety. (e.g., a fluorophore, a chromophore or a luminophore); wherein B optionally comprises a quencher; and wherein A and B are optionally cyclically linked.

A detectable moiety refers to any group or molecule that can be detected directly (e.g., via emission or absorption of light) or indirectly (e.g., via a secondary enzymatic reaction). Any convenient detectable moieties may be used in the subject probes. In some cases, the detectable moiety is an optically detectable label (e.g., a fluorescence or another type of light emitting or light absorbing label). In some cases, the detectable moiety is a fluorophore. "Fluorophore" refers to a molecule that, when excited with light having a selected wavelength, emits light of a different wavelength, which may emit light immediately or with a delay after excitation. In some cases, the detectable moiety is a fluorogenic group in the context of the probe, such as a profluorophore that is chemically transformed by the subject reaction of the probe with formaldehyde into a fluorophore. Fluorophores of interest that may be adapted for use in the subject probes, include but are not limited to, xanthene dyes, fluorescein dyes, rhodamine dyes, rhodol dyes, cyanine dyes, and the like.

Fluorescent dye moieties of interest that may be adapted for use in the subject probes include, but are not limited to, fluorescent dyes such as fluorescein, 6-FAM, rhodamine, Texas Red, tetramethylrhodamine, carboxyrhodamine, carboxyrhodamine 6G, carboxyrhodol, carboxyrhodamine 110, Cascade Blue, Cascade Yellow, coumarin, Cy2, Cy3, Cy3.5, Cy5, Cy5.5, Cy-Chrome, phycoerythrin, PerCP (peridinin chlorophyll-a Protein), PerCP-Cy5.5, JOE (6-carboxy-4',5'-dichloro-2',7'-dimethoxyfluorescein), NED, ROX (5-(and -6)-carboxy-X-rhodamine), HEX, Lucifer Yellow, Marina Blue, Oregon Green 488, Oregon Green 500, Oregon Green 514, Alexa Fluor 350, Alexa Fluor 430, Alexa Fluor 488, Alexa Fluor 532, Alexa Fluor 546, Alexa Fluor 568, Alexa Fluor 594, Alexa Fluor 633, Alexa Fluor 647, Alexa Fluor 660, Alexa Fluor 680, Alexa Fluor 700, 7-amino-4-methylcoumarin-3-acetic acid, BODIPY FL, BODIPY FL-Br.sub.2, BODIPY 530/550, BODIPY 558/568, BODIPY 564/570, BODIPY 576/589, BODIPY 581/591, BODIPY 630/650, BODIPY 650/665, BODIPY R6G, BODIPY TMR, BODIPY TR, rose bengal, acridine orange, methylene blue, erythrosine, conjugates thereof, polymeric dyes and combinations thereof. Lanthanide chelates of interest include, but are not limited to, europium chelates, terbium chelates and samarium chelates.

In some cases, the detectable moiety is a chromophore. In certain instances, the detectable moiety is a protected fluorophore, chromophore or luminophore.

In some cases, the detectable moiety is a luminophore. In some cases, the detectable moiety is a luminogenic group in the context of the probe, such as a proluminophore group that is chemically transformed by the subject reaction of the probe with formaldehyde into a luminophore. A "luminescent probe" or "luminophore" refers to a molecule that, when it undergoes a chemical reaction, can convert chemical energy to produce a light emission. A chemiluminescent reaction may include, for example, a chemical or enzymatic reaction. Luminescent probes include, without limitation, a luciferin (e.g., a firefly luciferin); an aminoluciferin; coelenterazine; a coelenterazine analog, a membrane permeant coelenterazine analog, dihydroluciferin; luciferin 6' methylether; luciferin 6' chloroethylether, a red-shifted thermostable luciferase, and a 1,2-dioxetane containing compound.

In some embodiments, a luminophore that has been adapted for incorporation into the subject probes is a luminophore such as a luciferin (e.g., a firefly luciferin); an aminoluciferin; coelenterazine; a modified coelenterazine as described in U.S. Pat. No. 7,537,912; a coelenterazine analog as described in U.S. Patent Publication No. 2009/0081129 (e.g., a membrane permeant coelenterazine analog as described in U.S. Patent Publication No. 2009/0081129, e.g., one of Structures II, III, IV, V, and VI of U.S. Patent Publication No. 2009/0081129); aminoluciferin; dihydroluciferin; luciferin 6' methylether; or luciferin 6' chloroethylether. See, e.g., Branchini, B. R. et al. *Anal. Biochem.* 2010, 396, 290-296; and Mezzanotte, L. et al., In vivo bioluminescence imaging of murine xenograft cancer models with a red-shifted thermostable luciferase. *Mol. Imaging Biol.* (2009, Nov. 9, online; PubMed ID: 19937390).

In some cases, organic dyes that may be adapted for use as a luminophore, chromophore or fluorophore in the subject probes may selected from the group consisting of coumarins, pyrene, cyanines, benzenes, N-methylcarbazole, erythrosin B, N-acetyl-L-tryptophanamide, 2,5-diphenyloxazole, rubrene, and N-(3-sulfopropyl)acridinium. Specific examples of preferred coumarins include 7-aminocoumarin, 7-dialkylamino coumarin, and coumarin 153. Examples of preferred benzenes include 1,4-bis(5-phenyloxazol-2-yl) benzene and 1,4-diphenylbenzene. Examples of preferred cyanines include oxacyanines, thiacyanines, indocyanins, merocyanines, and carbocyanines. Other exemplary cyanines include ECL Plus, ECF, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, CypHer5, Dye-33, Cy7, Cy5, Cy5.5, Cy3Cy5 ET, Cy3B, Cy3, Cy3.5, Cy2, CBQCA, NIR1, NIR2, NIR3, NIR4, NIR820, SNIR1, SNIR2, SNIR4, Merocyanine 540, Pinacyanol-Iodide, 1,1-Diethyl-4,4-carbocyanine iodide, Stains All, Dye-1041, or Dye-304.

The term coelenterazine is defined as a molecule with an imidazopyrazine structure, characterized by its ability to luminesce when contacted with a given luminogenic protein in solution. Coelenterazines are known to luminesce when acted upon by a wide variety of luminogenic proteins, specifically marine luciferases. Examples of marine luciferases include Renilla luciferase, aequorin, Gaussia luciferase, Oplophorus luciferase, and Cypridina luciferase.

In some embodiments of formula (I), A comprises a fluorophore and B comprises a quencher that is in energy-receiving proximity to the fluorophore. Energy-receiving proximity refers to the configuration required for fluorescence resonance energy-transfer (FRET) to occur between two light sensitive donor and acceptor groups. In some cases, the energy-transfer may be referred to as a donor-excited photoinduced electron transfer (d-PeT) process. In one embodiment, the subject probes provide for generation of a fluorescent signal upon reaction with formaldehyde by release of the quencher from the fluorophore.

In some embodiments, the probe has the formula (II):

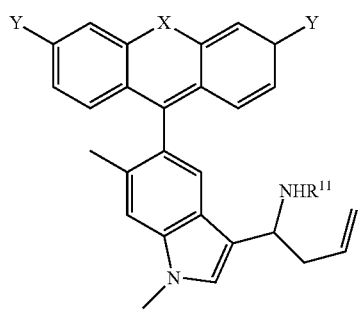

wherein:

X is selected from the group consisting of O, SiR$_2$, CR$_2$, SnR$_2$, BF$_2$, S, Se, Te, PO$_2$H, AsO$_2$H, wherein each R is independently H or an alkyl (e.g., methyl);

each Y is independently selected from =O, —OH, —NH$_2$, =NH, —NR'R", =N$^+$R'R", wherein R' and R" are independently an alkyl or a substituted alkyl, or R' and R" are cyclically linked to form, with the N to which they are attached, a five or six-membered heterocycle or substituted heterocycle; and R$^{11}$ is selected from the group consisting of hydrogen, alkyl, substituted alkyl, alkoxy, substituted alkoxy, aralkyl, substituted aralkyl, aryl, substituted aryl, heteroaryl and substituted heteroaryl, and wherein R$^{11}$ optionally comprises the quencher.

In certain embodiments of formula (II), X is O. In certain embodiments of formula (II), X is SiMe$_2$. In certain embodiments of formula (II), X is CMe$_2$. In certain embodiments of formula (II), X is SnMe$_2$. In certain embodiments of formula (II), X is BF$_2$. In certain embodiments of formula (II), X is S. In certain embodiments of formula (II), X is Se. In certain embodiments of formula (II), X is Te. In certain embodiments of formula (II), X is PO$_2$H. In certain embodiments of formula (II), X is AsO$_2$H.

In certain embodiments of formula (II), each Y is independently selected from one of the following structures:

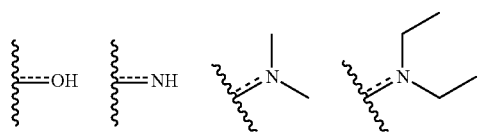

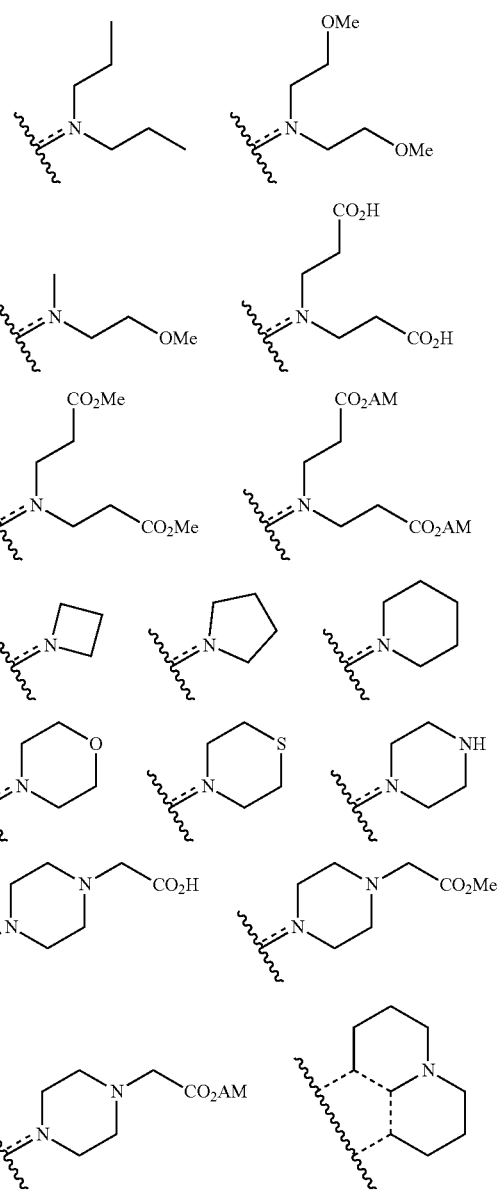

wherein when Y is connected to the probe via a double bond, it can be positively charged. In certain embodiments of formula (II), each Y is —OH or =O. In certain embodiments of formula (II), each Y is NH$_2$ or =NH.

In certain embodiments of formula (II), R$^{11}$ is selected from one of the following structures:

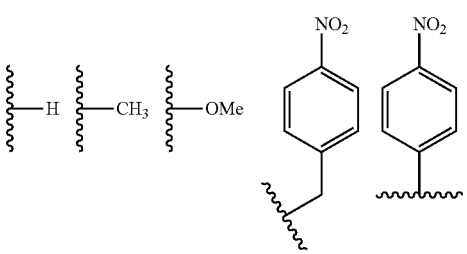

-continued

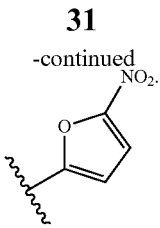

In certain embodiments of formula (II), $R^{11}$ is H. In certain embodiments of formula (II), $R^{11}$ is Me. In certain embodiments of formula (II), $R^{11}$ is OMe. In certain embodiments of formula (II), $R^{11}$ is $CH_2Ph$-$NO_2$. In certain embodiments of formula (II), $R^{11}$ is Ph-$NO_2$. In certain embodiments of formula (II), $R^{11}$ is 5-nitrofuranyl.

In some cases, the probe is a fluorogenic and is configured to be chemically transformed by the subject reaction of the probe with formaldehyde into a fluorophore. In certain cases, the transformation results in a detectable change in fluorescence. In some embodiments, the probe has the formula (III):

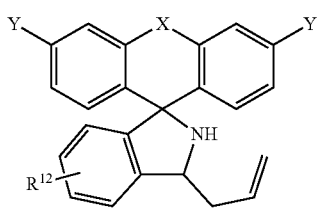

wherein:

X is selected from the group consisting of O, $SiR_2$, $CR_2$, $SnR_2$, $BF_2$, S, Se, Te, $PO_2H$, $AsO_2H$, wherein each R is independently H or an alkyl (e.g., methyl);

each Y is independently selected from =O, —OH, —$NH_2$, =NH, —NR'R", =$N^+$R'R", wherein R' and R" are independently an alkyl or a substituted alkyl, or R' and R" are cyclically linked to form, with the N to which they are attached, a five or six membered heterocycle or substituted heterocycle; and $R^{12}$ is hydrogen, carboxy, an ester, an amido, an alkyl-amido or a substituted alkyl-amido, wherein $R^{12}$ optionally comprises a chemoselective tag.

In certain embodiments of formula (III), X is O. In certain embodiments of formula (III), X is $SiMe_2$. In certain embodiments of formula (III), X is $CMe_2$. In certain embodiments of formula (III), X is $SnMe_2$. In certain embodiments of formula (III), X is $BF_2$. In certain embodiments of formula (III), X is S. In certain embodiments of formula (III), X is Se. In certain embodiments of formula (III), X is Te. In certain embodiments of formula (III), X is $PO_2H$. In certain embodiments of formula (III), X is $AsO_2H$.

In certain embodiments of formula (III), each Y is independently selected from one of the following structures:

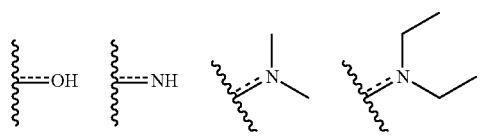

-continued

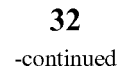

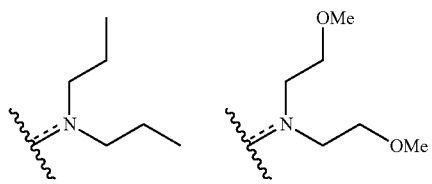

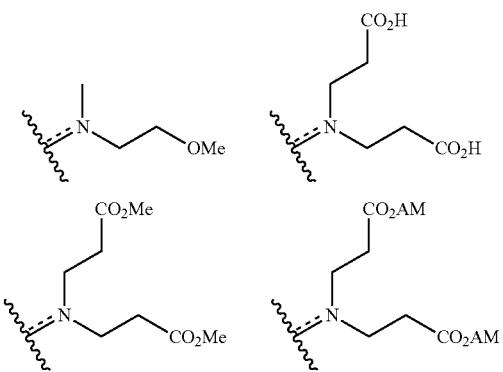

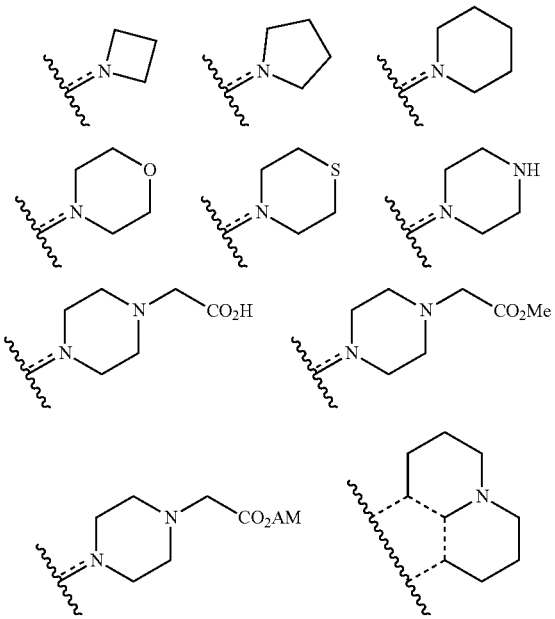

wherein when Y is connected to the probe via a double bond, it can be positively charged. In certain embodiments of formula (II), each Y is —OH or =O. In certain embodiments of formula (II), each Y is $NH_2$ or =NH.

In certain embodiments of formula (III), $R^{12}$ is selected from one of the following structures:

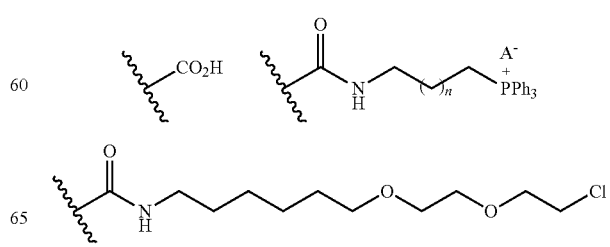

-continued

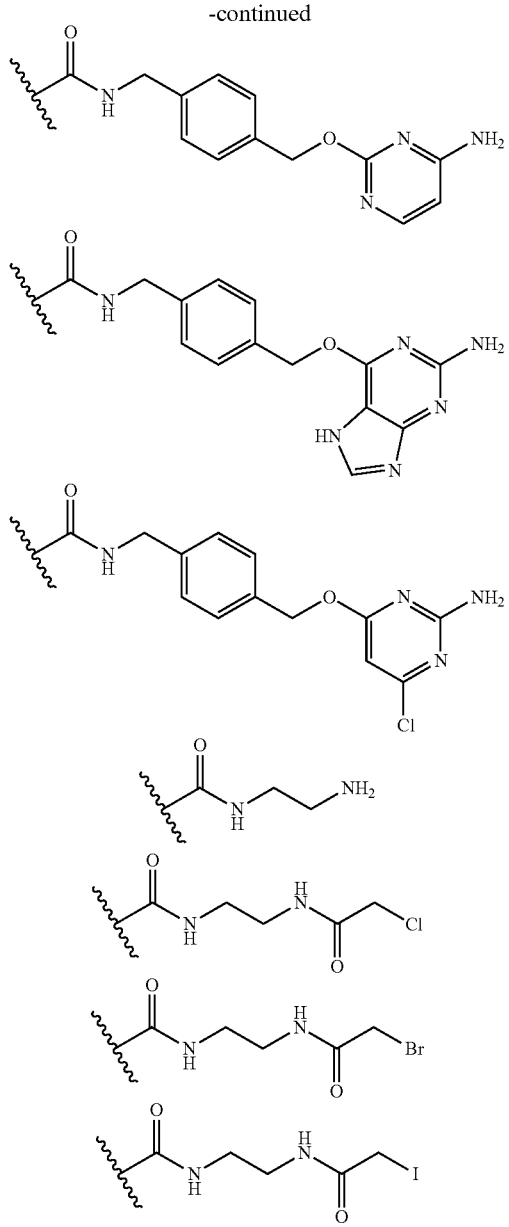

wherein n is 0, 1, 2, 3, 4, 5 or 6; and A is a counteranion (e.g., Cl⁻, Br⁻, I⁻, HCOO⁻ or F₃CCOO⁻). In certain embodiments of formula (III), $R^{12}$ is $CO_2H$. In certain embodiments of formula (III), $R^{12}$ comprises a chemoselective group. In certain embodiments of formula (III), $R^{12}$ comprises an active ester (e.g., an NHS ester). "Chemoselective group" refers to a functional group that is orthogonal to the homoallylamine group, e.g., does not react with the homoallylamine group, but is capable of reaction with a compatible functional group to form a covalent bond.

In some instances, $R^{12}$ comprises or is terminated with a functional group selected from amine, carbamate, carboxylate, carboxylic acid, maleimide, activated esters, N-hydroxysuccinimidyl, hydrazines, hydrazids, hydrazones, azide, alkyne, aldehydes, thiols, and protected groups thereof for use in conjugation to another substrate, molecule or biomolecule.

In some embodiments of formula (I), A has the formula (IV):

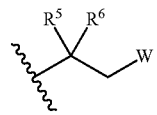

wherein $R^5$ and $R^6$ are independently selected from the group consisting of hydrogen, an alkyl, a substituted alkyl, an aryl, a substituted aryl, a heteroaryl, a substituted heteroaryl, a halogen, a cyano, an azido, an alkoxy, a substituted alkoxy, a hydroxyl, a carboxy and an amido; and W comprises a detectable moiety. Any convenient luminophore, fluorophore or chromophore may be adapted for use as the W detectable moiety. In some instances, W is selected from the group consisting of a luciferin, a substituted luciferin, an aminoluciferin, a coelenterazine, a modified coelenterazine, a coumarin dye, a xanthene dye, a xanthene analog, a fluorescein dye, a rhodamine dye, a cyanine dye, a polymethine, a pyrene, a dipyrromethene a borondifluoride and a naphthalimide.

In certain embodiments of formula (I) and (IV), the probe has the formula (V)

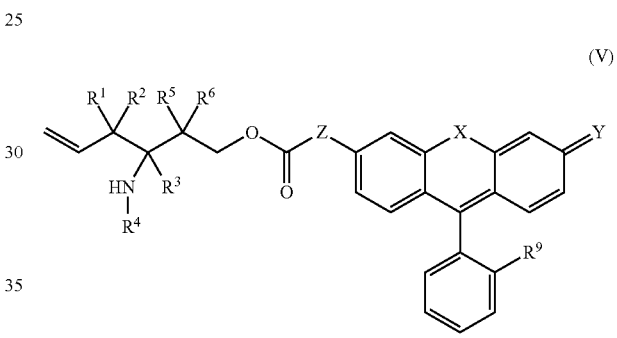

wherein Z is O, S, NH or NR' wherein R' is an alkyl or substituted alkyl (e.g., methyl); $R^9$ is selected from the group consisting of hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy, a carboxy ester and an amido; and X and Y are as defined in Formulae (II) and (III) above.

In certain embodiments of formula (I) and (IV), the probe has the formula (VI)

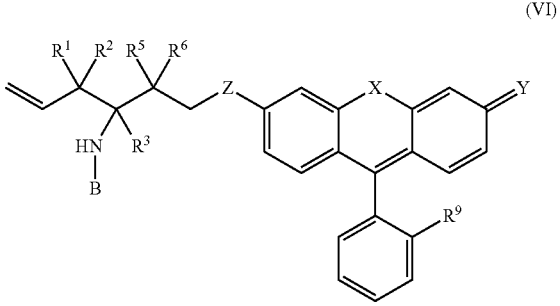

wherein Z is O, S, NH or NR' wherein R' is an alkyl or substituted alkyl (e.g., methyl); $R^9$ is selected from the group consisting of hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy, a carboxy ester and an amido; and X and Y are as defined in Formulae (II) and (III) above.

In certain embodiments of formula (I) and (IV), the probe has the formula (VII)

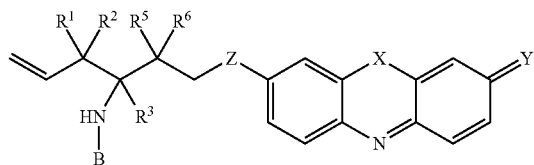

(VII)

wherein Z is O, S, NH or NR' wherein R' is an alkyl or substituted alkyl (e.g., methyl);
and X and Y are as defined in Formulae (II) and (III) above.

In certain embodiments of formula (I) and (IV), the probe has the formula (VIII)

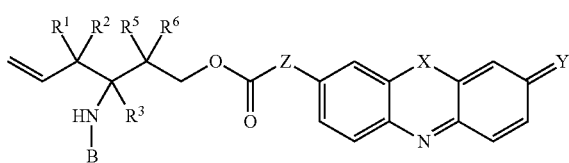

(VIII)

wherein Z is O, S, NH or NR' wherein R' is an alkyl or substituted alkyl (e.g., methyl);
and X and Y are as defined in Formulae (II) and (III) above.

In certain embodiments of formula (I) and (IV), the probe has the formula (IX)

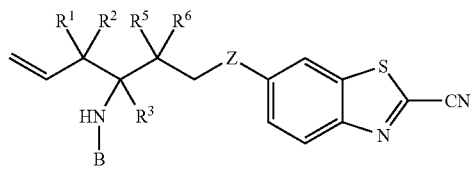

(IX)

wherein Z is O, S, NH or NR' wherein R' is an alkyl or substituted alkyl (e.g., methyl).

In certain embodiments of formula (I) and (IV), the probe has the formula (X)

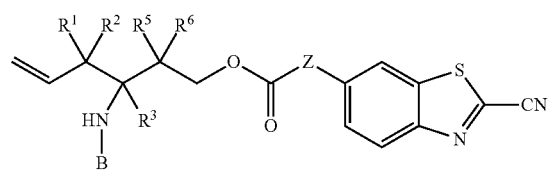

(X)

wherein Z is O, S, NH or NR' wherein R' is an alkyl or substituted alkyl (e.g., methyl).

In certain embodiments of formula (I) and (IV), the probe has the formula (XI)

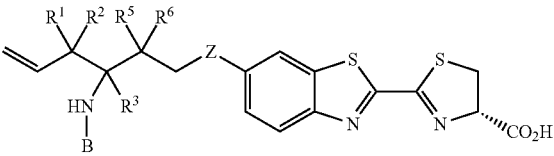

(XI)

wherein Z is O, S, NH or NR' wherein R' is an alkyl or substituted alkyl (e.g., methyl).

In certain embodiments of formula (I) and (IV), the probe has the formula (XII)

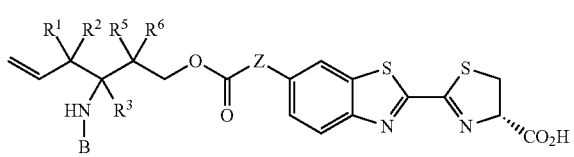

(XII)

wherein Z is O, S, NH or NR' wherein R' is an alkyl or substituted alkyl (e.g., methyl).

In some instances of formula (I), A is the detectable moiety (e.g., a chromophore or fluorophore). In such cases, reaction of the probe with formaldehyde produces a product where the optical properties of the detectable moiety are different as compared to the starting probe. In some embodiments, the probe has the formula (XIII):

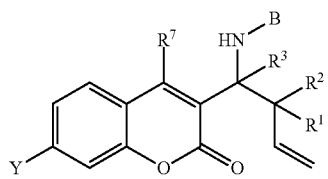

(XIII)

wherein $R^1$-$R^3$ and Y are as defined above in formula (I)-(III); $R^7$ is selected from the group consisting of hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy, a carboxy ester and an amido; and B is selected from the group consisting of hydrogen, alkyl, substituted alkyl, hydroxy, alkoxy, substituted alkoxy, aryl, substituted aryl, aralkyl, substituted aralkyl, heterarylalkyl, and substituted heterarylalkyl.

In some embodiments, the probe has the formula (XIV):

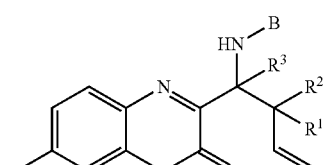

(XIV)

wherein $R^1$-$R^3$ and Y are as defined above in formula (I)-(III); and B is selected from the group consisting of hydrogen, alkyl, substituted alkyl, hydroxy, alkoxy, substituted alkoxy, aryl, substituted aryl, aralkyl, substituted aralkyl, heterarylalkyl, and substituted heterarylalkyl.

In some embodiments, the probe has the formula (XV):

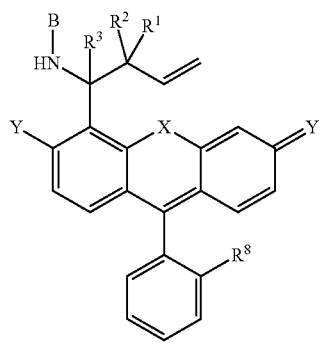

(XV)

wherein $R^1$-$R^3$, X and each Y are as defined above in formula (I)-(III); $R^8$ is selected from the group consisting of hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy, a carboxy ester and an amido; and B is selected from the group consisting of hydrogen, alkyl, substituted alkyl, hydroxy, alkoxy, substituted alkoxy, aryl, substituted aryl, aralkyl, substituted aralkyl, heterarylalkyl, and substituted heterarylalkyl.

In some embodiments, the probe has the formula (XVI):

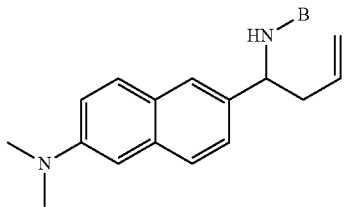

(XVI)

wherein B is selected from the group consisting of hydrogen, alkyl, substituted alkyl, hydroxy, alkoxy, substituted alkoxy, aryl, substituted aryl, aralkyl, substituted aralkyl, heterarylalkyl, and substituted heterarylalkyl.

In certain embodiments of formulae (V)-(XVI), each Y is independently selected from one of the following structures:

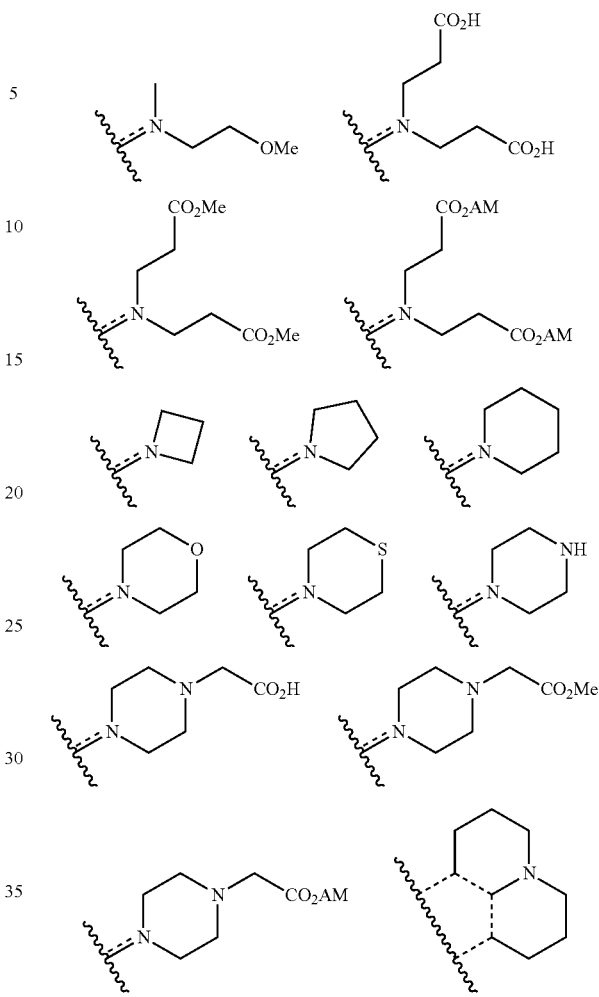

wherein when Y is connected to the probe via a double bond, it can be positively charged.

In certain embodiments of formulae (V)-(XVI), B is a substituted aralkyl (e.g., a substituted benzyl, such as a nitro-substituted benzyl). In certain embodiments of formulae (V)-(XVI), B is a substituted heteroaryl or a substituted aryl (e.g., a nitro-substituted heteroaryl, such as a nitro-substituted furanyl). In certain embodiments of formulae (V)-(XVI), B is selected from one of the following structures:

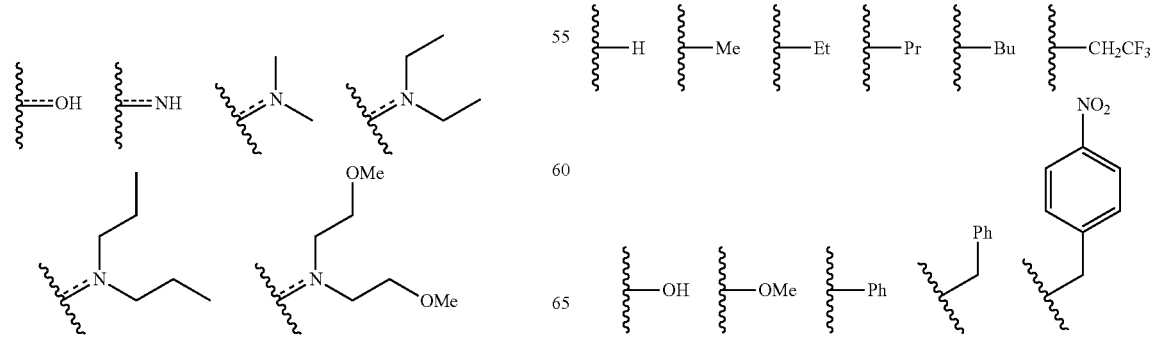

-continued

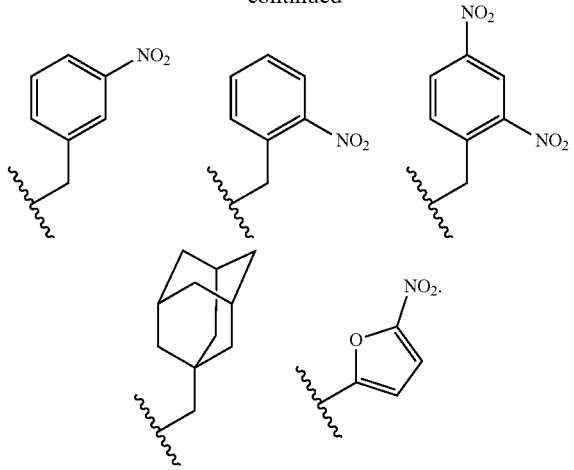

In certain embodiments of formulae (V)-(XVI), $R^1$, $R^2$, $R^3$, $R^7$, $R^8$ and $R^9$ are independently selected from one of the following structures:

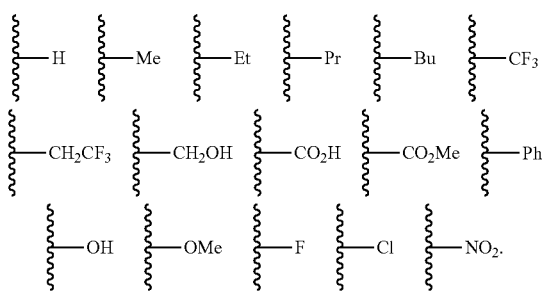

Methods

As summarized above, aspects of the present disclosure include methods of detecting formaldehyde in a sample. The method may include contacting the sample of interest with a subject probe (e.g., as described herein). Any convenient method may be used to contact the sample with a probe that selectively reacts with the reactive carbonyl species of interest (e.g., formaldehyde) to release a reporter group comprising a detectable moiety. In some instances, the sample is contacted with the probe under conditions in which probe selectively reacts with formaldehyde, if present. As described above, the selectively reacting may comprise performing a 2-aza-Cope rearrangement on the contacted probe to release the reporter group. In some embodiments, the reporter group has the formula:

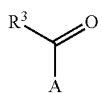

wherein A comprises a fluorophore, a chromophore or a luminophore and $R^3$ is as described for Formula (I). In certain cases, A comprises a fluorophore. In certain cases, A comprises a luminophore. In certain cases, A comprises a chromophore.

The formaldehyde may be present in the sample at physiologically relevant concentrations, such as a concentration of about 100 μM or more, such as 200 μM or more or 400 μM or more. In some cases, for selective reaction of the probe with formaldehyde, an appropriate solution may be used that maintains the integrity of the probe and any other analytes of interest (e.g., biomolecules) in the sample. The solution may be a balanced salt solution, e.g., normal saline, phosphate buffered saline (PBS), Hank's balanced salt solution, etc., conveniently supplemented with fetal calf serum, human platelet lysate or other factors, in conjunction with an acceptable buffer at low concentration, such as from 5-25 mM. Convenient buffers include HEPES, phosphate buffers, lactate buffers, etc. Various media are commercially available and may be used according to the nature of the target cells, including dMEM, HBSS, dPBS, RPMI, Iscove's medium, etc., frequently supplemented with fetal calf serum or human platelet lysate. The final components of the solution may be selected depending on the components of the sample which are included.

The temperature at which selective reaction of the probe and the reactive carbonyl species (e.g., formaldehyde) takes place may vary, and in some instances may range from 5° C. to 50° C., such as from 10° C. to 40° C., 15° C. to 40° C., 20° C. to 40° C., e.g., 20° C., 25° C., 30° C., 35° C. or 37° C. (e.g., as described above). In some instances, the temperature at which specific binding takes place is selected to be compatible with the viability of a cell sample and/or the biological activity of an analyte of interest. In certain instances, the temperature is 25° C., 30° C., 35° C. or 37° C. In certain cases, the temperature at which the probe reaction takes place is room temperature (e.g., 25° C.), 30° C., 35° C. or 37° C. Any convenient incubation time for the probe reaction may be selected to allow for the formation of a desirable amount of reporter group product, and in some instances, may be 1 minute (min) or more, such as 2 min or more, 10 min or more, 30 min or more, 1 hour or more, 2 hours or more, or even 6 hours or more.

The subject methods may be performed in a variety of biological samples. As used herein, the term "a biological sample" refers to a whole organism or a subset of its tissues, cells or component parts (e.g. body fluids, including, but not limited to, blood, serum, plasma, bronchoalveolar lavage, mucus, lymphatic fluid, synovial fluid, saliva, cerebrospinal fluid, amniotic fluid, amniotic cord blood, urine, vaginal fluid, and semen). A "biological sample" can also refer to a homogenate, lysate or extract prepared from a whole organism or a subset of its tissues, cells or component parts, or a fraction or portion thereof, including but not limited to, plasma, serum, spinal fluid, lymph fluid, the external sections of the skin, respiratory, intestinal, and genitourinary tracts, tears, saliva, milk, blood cells, tumors and organs. In certain embodiments, the sample has been removed from an animal or plant. Biological samples may include cells. The term "cells" is used in its conventional sense to refer to the basic structural unit of living organisms. In certain embodiments, cells include prokaryotic cells, such as from bacteria. In other embodiments, cells include eukaryotic cells, such as cells obtained from biological samples from animals, plants, or fungi. The sample may include a heterogeneous cell population from which target cells are isolated. In some instances, the sample includes peripheral whole blood, peripheral whole blood in which erythrocytes have been lysed prior to cell isolation, cord blood, bone marrow, density gradient-purified peripheral blood mononuclear cells or homogenized tissue.

In some embodiments, the biological sample includes a cell. A variety of cells may be used in conjunction with the subject methods. Target cells of interest include, but are not limited to, stem cells, e.g., pluripotent stem cells, hematopoietic stem cells, T cells, T regulator cells, dendritic cells, B Cells, e.g., memory B cells, antigen specific B cells, granulocytes, leukemia cells, lymphoma cells, virus-infected cells (e.g., HIV-infected cells), natural killer (NK) cells, macrophages, monocytes, fibroblasts, epithelial cells, endothelial cells, and erythroid cells. Target cells of interest include cells that have a convenient cell surface marker or antigen that may be captured by a convenient specific binding member or conjugates thereof. Target cells include cells that are abnormal, e.g., diseased cells. Target cells include, e.g., cancer cells, virus-infected cells, and the like.

Aspects of the subject methods include detecting the detectable moiety of the reporter group thereby providing for detection of the formaldehyde in the sample. In some embodiments, the detecting comprises fluorescently imaging the sample. Detection methods of interest include, but are not limited to, fluorescence microscopy, fluorescence spectroscopy, flow cytometry, absorbance spectroscopy. Detection may be achieved directly via a reporter molecule, or indirectly by a secondary detection system. The latter may be based on any one or a combination of several different principles including but not limited to, antibody labelled anti-species antibody and other forms of immunological or non-immunological bridging and signal amplification systems (e.g., biotin-streptavidin technology, protein-A and protein-G mediated technology, or nucleic acid probe/anti-nucleic acid probes, and the like). The label used for direct or indirect detection may be any detectable reported molecule. Suitable reporter molecules may be those known in the field of immunocytochemistry, molecular biology, light, fluorescence, and electron microscopy, cell immunophenotyping, cell sorting, flow cytometry, cell visualization, detection, enumeration, and/or signal output quantification. Labels of interest include, but are not limited to fluorophores, luminescent labels, metal complexes, radioisotopes, biotin, streptavidin, enzymes, or other detection labels and combination of labels such as enzymes and a luminogenic substrate. Enzymes of interest and their substrates include alkaline phosphatase, horseradish peroxidase, beta-galactosidase, and luciferase, and the like. More than one antibody of specific and/or non-specific nature might be labeled and used simultaneously or sequentially to enhance target detection, identification, and/or analysis. Labels of interest include, but are not limited to FITC (fluorescein isothiocyanate) AMCA (7-amino-4-methylcoumarin-3-acetic acid), Alexa Fluor 488, Alexa Fluor 594, Alexa Fluor 350, DyLight350, phycoerythrin, allophycocyanin and stains for detecting nuclei such as Hoechst 33342, LDS751, TO-PRO and DAPI.

In some instances, the detecting includes detecting a cell in a flow cytometer. Such a step may include exciting a fluorescent dye with one or more lasers at an interrogation point of the flow cytometer, and subsequently detecting fluorescence emission from the dye using one or more optical detectors. It may be desirable, in addition to detecting the particle (e.g., cell), to determine the number of particles (e.g., cells) separated, or utilizing one or components of the methods for the purpose of sorting the particles. Accordingly, in some embodiments, the methods further include counting, sorting, or counting and sorting the labeled particle (e.g., target cell).

In some embodiments, the method further comprises analyzing the level of formaldehyde in the sample. Any convenient methods may be used to analyze the level of formaldehyde in the sample.

In certain embodiments of the present disclosure, the probes may be used as assay reagents. Assays using detectable moieties such as fluorophores, chromophores and luminophores are well known in the art. Such assays may be adapted for use in the subject methods for analyzing biological mechanisms for interest. In some cases, a sample of interest (e.g., cells) are contacted with a subject probe, then a change in an optical property is detected. The presence of a reactive carbonyl species (e.g., formaldehyde) in the sample is determined by the addition of the probe reagent.

In some instances, the subject methods are bioorthogonal such that the subject probe can selectively react with formaldehyde in the presence of the endogenous components of any convenient biological sample. In some instances, the FA that is detected according to the subject methods is produced endogenously in a sample by a demethylase and/or oxidase enzymes, e.g., a lysine-specific demethylase 1 (LSD1), a JmjC domain-containing protein, or a semi-carbazide-sensitive amine oxidase. In certain embodiments, the method further comprises analyzing the activity of an enzyme endogenous to the sample, e.g., by correlating the levels of FA present in a sample to the activity of an enzyme of interest. The enzyme activity may be analyzed over any convenient time period and under any convenient conditions.

As such, the probes of the present disclosure are useful in in situ methods of analyzing cells. Methods of performing in situ analysis of cells using detectable moieties such as fluorophores, chromophores and luminophores are known in the art and may be adapted for use in the subject methods.

Any convenient concentration of probe in the sample may be achieved in the subject methods. In some instances, the concentration of probe may be between 0.1 mM and 100 mM, such as between 0.5 mM and 10 mM, between 0.5 mM and 5 mM or between 5 mM and 10 mM. In certain cases, the solution is an aqueous solution. In certain instances, the concentration of indole agent in the aqueous solution is 0.1 mM or more, such as 0.2 mM or more, 0.3 mM or more, 0.4 mM or more, 0.5 mM or more, 1.0 mM or more, 2 mM or more, 3 mM or more, 4 mM or more, 5 mM or more, 6 mM or more, 7 mM or more, 8 mM or more, 9 mM or more, 10 mM or more, or even more.

As summarized above, aspects of the present disclosure include methods of detecting formaldehyde in a cell, tissue, organ or fluid in a subject. The method may comprise administering the probe (e.g., as described herein) to the subject thereby selectively reacting the probe with the formaldehyde in the sample to a release a reporter group comprising a detectable moiety.

Aspects of the method include detecting the detectable moiety in the cell, tissue, organ or fluid, thereby providing for detection of the formaldehyde. Any convenient methods of detecting (e.g., as described herein) may be utilized in the subject methods to detect the reporter group in vivo, or in vitro in a sample taken from the subject. In some cases, the subject is human. In some cases, the subject is a mammal. In some cases, the subject is a non-human animal, such as a mouse, rat, cat, dog, monkey, etc.

Administration of the subject probes may be systemic or local. In certain embodiments administration to a subject will result in systemic release of a compound of the invention (for example, into the bloodstream). Methods of administration may include enteral routes, such as oral, buccal, sublingual, and rectal; topical administration, such as transdermal and intradermal; and parenteral administration. Suitable parenteral routes include injection via a hypodermic needle or catheter, for example, intravenous, intramuscular, subcutaneous, intradermal, intraperitoneal, intraarterial, intraventricular, intrathecal, and intracameral injection and non-injection routes, such as intravaginal rectal, or nasal administration. For example, the probes can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Compositions and Kits

Aspects of the present disclosure further include kits and compositions including the subject probes (e.g., as described herein) for use in practicing the subject methods. The probes and compositions of the present disclosure can be included as reagents in kits either as starting materials or provided for use in, for example, the methodologies described above.

A composition may include a probe (e.g., as described herein) and a reactive carbonyl species (e.g., as described herein, such as formaldehyde). The composition may be contained in a biological sample.

A kit may include a probe (e.g., as described herein); and one or more components selected from a reactive carbonyl species (e.g., as described herein, such as formaldehyde), an enzyme (e.g., a demethylase), a fluorescent dye, a fluorescently labelled conjugate, a cell, a support, a biocompatible aqueous buffer, and instructions for use. One or more of the components of the kit may find use as control reagent for an assay of interest. The one or more additional components may be provided in separate containers (e.g., separate tubes, bottles, or wells in a multi-well strip or plate).

In certain aspects, the kit may further include reagents for performing a flow cytometric assay. Examples of said reagents include buffers for at least one of reconstitution and dilution of the first and second detectable molecules, buffers for contacting a cell sample with one or both of the first and second detectable molecules, wash buffers, control cells, control beads, fluorescent beads for flow cytometer calibration and combinations thereof. The kit may also include one or more cell fixing reagents such as paraformaldehyde, glutaraldehyde, methanol, acetone, formalin, or any combinations or buffers thereof. Further, the kit may include a cell permeabilizing reagent, such as methanol, acetone or a detergent (e.g., triton, NP-40, saponin, tween 20, digitonin, leucoperm, or any combinations or buffers thereof. Other protein transport inhibitors, cell fixing reagents and cell permeabilizing reagents familiar to the skilled artisan are within the scope of the subject kits.

The probes and compositions may be provided in a liquid composition, such as any suitable buffer. Alternatively, the probes and compositions may be provided in a dry composition (e.g., may be lyophilized), and the kit may optionally include one or more buffers for reconstituting the dry composition. In certain aspects, the kit may include aliquots of the probes and compositions provided in separate containers (e.g., separate tubes, bottles, or wells in a multi-well strip or plate).

In addition, one or more components may be combined into a single container, e.g., a glass or plastic vial, tube or bottle. In certain instances, the kit may further include a container (e.g., such as a box, a bag, an insulated container, a bottle, tube, etc.) in which all of the components (and their separate containers) are present. The kit may further include packaging that is separate from or attached to the kit container and upon which is printed information about the kit, the components of the and/or instructions for use of the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, DVD, portable flash drive, etc., on which the information has been recorded. Yet another means that may be present is a website address which may be used via the Internet to access the information at a removed site. Any convenient means may be present in the kits.

Utility

The subject methods and probes find use in a variety of applications, including research applications and diagnostic applications. Research applications of interest include any application where the investigation, manipulation, tracking of a reactive carbonyl species (e.g., formaldehyde) in a sample is of interest, including application where the species directly or indirectly interacts with a biomolecule of interest, such as in an enzymatic system.

Diagnostic applications of interest include any application where formaldehyde is implicated in a disease pathology, including various cancers, neurodegenerative diseases, diabetes, and chronic liver and heart disorders.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

The following materials and methods were used in the Example described below.

General Materials and Methods

Thin-layer chromatography (TLC) was performed on glass-backed TLC plates precoated with silica gel containing an $UV_{254}$ fluorescent indicator (Macherey-Nagel). Compounds were visualized with a 254/365 nm, handheld UV lamp (UVP). Flash chromatography was performed using 230-400 mesh silica gel P60 (SiliCycle Inc). Solvents used for anhydrous reactions were dried over 3 Å molecular sieves activated via heating under vacuum at 300° C. All glassware used in anhydrous reactions were flame-dried or heated overnight in an oven at 160° C. and cooled immediately prior to use. 3-Bromoaniline, 3-bromoanisole, 4-bromo-3-methylaniline, 4-nitrobenzaldehyde, N-iodosuccinimide, potassium allyltrifluoroborate, sodium triacetoxyborohydride, tetrakis(triphenylphosphine)palladium(0), trifluoromethanesulfonic acid, and trimethylacetylene were purchased from Oakwood Products and used as received.

1-Bromo-3-chloropropane, aluminum trichloride, boron tribromide, copper iodide, dichlorodimethylsilane, formaldehyde solution, methyl chloroformate, phosphorous oxychloride, sec-butyllithium solution, and tert-butyllithium solution were purchased from Sigma-Aldrich and used without purification. Deuterated solvents were purchased from Cambridge Isotope Laboratories. ER-Tracker™ Green, LysoTracker® Green DND-26, MitoTracker® Green FM, DAPI, Trypan Blue solution were purchased from Life Technologies.

All buffers used for pH titrations were prepared in deionized water and brought to the appropriate pH with aqueous HCl or NaOH. The buffers used were 50 mM glycine (pH range 2.00-3.50), 50 mM NaOAc (pH range 4.00-5.60), 50 mM MES (pH range 5.60-6.80), 50 mM HEPES (pH range 6.80-8.20), 50 mM Tris (pH range 8.20-9.50) and 50 mM glycine (pH range 9.50-10.40). A 10 mM stock solution of formaldehyde for in vitro titration experiments was prepared by heating a suspension of paraformaldehyde (>88% w/w, 17.6 mg, 0.50 mmol, TCI, lot # NXR2B) in phosphate buffered saline (PBS) buffered to pH 7.4 (50 mL) at 88° C. for 1 hr. The solution was cooled to room temperature and filtered through a 0.22 μm syringe filter (Millex).

Spectroscopic Methods

Nuclear magnetic resonance (NMR) spectra were recorded on Varian 400 or 500 MHz spectrometers at 25° C. Chemical shifts are reported in ppm (δ) and are referenced to residual protic peaks. The following abbreviations are used to describe coupling constants: singlet (s), doublet (d), triplet (t), quartet (q), doublet doublet (dd), doublet triplet (dt), doublet quartet (dq), doublet doublet triplet (ddt), multiplet (m), and broad singlet (bs). IR spectra were recorded with a PerkinElmer Spectrum Two infrared (IR) spectrometer. High-resolution mass spectra were acquired with a Waters Q-TOF Ultima ESI mass spectrometer and a Waters Synapt G2-Si ESI/LC-MS mass spectrometer. UV-visible spectra were recorded on a Cary 60 spectrometer. Fluorescence spectra were acquired on a QuantaMaster-400 scanning spectrofluorometer with micro fluorescence quartz cuvettes (Science Outlet). Flow cytometry was performed on a BD Biosciences LSR II (San Jose, Calif., USA), and the data were analyzed as described using FACSDiva software.

Cell Culture and Imaging Materials and Methods

HEK293TN cells were obtained from Prof. Paul Hergenrother (UIUC, Chemistry) and cultured in phenol-red free Dulbecco's modified eagle medium (DMEM, Corning) supplemented with 10% fetal bovine serum (FBS, Sigma Aldrich), and 1% penicillin/streptomycin (Corning). Neuroscreen-1 cells were obtained from Prof. Kai Zhang (UIUC, Biochemistry) and cultured in Ham's F-12K medium (Sigma Aldrich) supplemented with 15% horse serum (Hyclone), 2.5% fetal bovine serum (FBS, Sigma Aldrich), and 1% penicillin/streptomycin (Corning). Cells were incubated at 37° C. and 5% $CO_2$. One day before imaging, cells were passed and plated on 8-well chambered coverglasses (Lab-Tek) at a density of 40,000 cells per mL (or 20,000 cells per well). Cells would reach 70-80% confluency before imaging. Immediately before the experiments, cells were washed with serum-free DMEM, incubated with FP1 in serum-free DMEM, rinsed with fresh media and imaged. Samples of HEK293TN and NS1 cells for flow cytometry were prepared by passaging and seeding each well of a 6-well cluster culture dish (Cyto-One) with 300,000 cells one day before experiments. Cells had reached 70% confluency before staining with 2 μM FP1 for 8 mins. Stained cells were aspirated and serum-free DMEM added. Subsequently, a 10× concentrated FA solution was added to give a final concentration of 1.0 mM. 2.5 mM and 5 mM. After incubation cells with FA, the media was removed and replaced with serum-free DMEM. Finally, cells were trypsinized, pelleted via centrifugation, resuspended in phosphate-buffered saline (PBS) for flow cytometric analysis.

Synthesis of Si-Xanthone

2-Bromo-4-methoxybenzyl Chloride

2-Bromo-4-methoxybenzyl chloride (FIG. 1, compound 7) was synthesized as follows. A two-neck round-bottom flask was charged with 3-bromoanisole (35.0 mL, 276.5 mmol, 1.0 eq.) and formaldehyde (37 wt % in $H_2O$, 38.0 mL, 1.38 mol, 5.0 eq.). Hydrogen chloride gas, generated from conc. hydrochloric acid and conc. sulfuric acid, was bubbled through the reaction mixture which was stirred at 50° C. for 6 hrs. Upon cooling to room temperature, the reaction was diluted with $H_2O$ (50 mL) and extracted with $CH_2Cl_2$ (3×50 mL). The combined organic fractions were washed with brine (100 mL), dried ($Na_2SO_4$), filtered and concentrated under reduced pressure. The crude residue was purified by fractional distillation to afford the title compound as a colorless oil (43.1 g, 183.1 mmol, 66.3% yield). $^1$H NMR (500 MHz, $CDCl_3$) δ 7.36 (d, J=8.5 Hz, 1H), 7.13 (d, J=2.6 Hz, 1H), 6.85 (dd, J=8.5, 2.6 Hz, 1H), 4.68 (s, 2H), 3.79 (s, 3H). $^{13}$C NMR (125 MHz, $CDCl_3$) δ 160.5, 132.0, 129.0, 125.0, 118.6, 114.0, 55.8, 46.5. IR (neat): 3008, 2966, 2937, 1602, 1492, 1263, 1242, 1028, 865, 843, 729, 661 $cm^{-1}$. HR-MS calculated for $C_8H_8BrClO$ $[M-HCl]^+$ m/z 198.9753. found 198.9759.

8-Bromo-1,2,3,5,6,7-hexahydropyrido[3,2,1-ij]quinoline

8-Bromo-1,2,3,5,6,7-hexahydropyrido[3,2,1-ij]quinolone (FIG. 1, compound 8) was synthesized as follows. A round-bottom flask was charged with 3-bromoaniline (8.0 mL, 73.1 mmol, 1.0 eq.), 1-bromo-3-chloropropane (58.5 mL, 584.6 mmol, 8.0 eq.), and $Na_2CO_3$ (31.0 g, 292.3 mmol, 4.0 eq.). After stirring at 140° C. for 48 hrs, the reaction cooled to room temperature, transferred to a separatory funnel, and extracted with $CH_2Cl_2$ (3×100 mL). The combined organic fractions were dried ($Na_2SO_4$), filtered, and concentrated under reduced pressure. Residual 1-bromo-3chloropropane was removed at 60° C., 1 Torr. The crude dialkylated intermediate was dissolved in DMF (15.0 mL) and stirred at 160° C. for 24 hrs. After cooling to room temperature, the solution was concentrated under reduced pressure, washed with $H_2O$ (200 mL), and extracted with $CH_2Cl_2$ (3×100 mL). The combined organic fractions were dried ($Na_2SO_4$), filtered, and concentrated under reduced pressure. The crude residue was purified via flash chromatography on a silica column (1:99 v/v EtOAc:Hexanes) to afford the title compound as a light yellow oil (12.0 g, 47.6 mmol, 65.1% yield). $^1$H NMR (400 MHz, $CDCl_3$) δ 6.78 (d, J=8.0 Hz, 1H), 6.66 (d, J=8.0 Hz, 1H), 3.14 (dt, J=12.5, 5.7 Hz, 4H), 2.80 (t, J=6.7 Hz, 2H), 2.72 (t, J=6.5 Hz, 2H), 2.07-1.87 (m, 4H). $^{13}$C NMR (100 MHz, $CDCl_3$) δ 144.8, 128.0, 123.2, 120.9, 120.8, 119.6, 50.2, 49.9, 28.8, 27.8, 22.2, 22.1. IR (neat): 3009, 2935, 1583, 1488, 1456, 1440, 1388, 1327, 1207, 1186, 1067, 1038, 792, 755, 578, 463 $cm^{-1}$. HR-MS calculated for $C_{12}H_{14}BrN$ $[M+H]^+$ m/z 252.0388. found 252.0393.

8-Bromo-9-(2-bromo-4-methoxybenzyl)-2,3,6,7-tetrahydro-1H,5H-pyrido[3,2,1-ij]quinoline 8-Bromo-9-(2-bromo-4-methoxybenzyl)-2,3,6,7-tetrahydro-1H,5H-pyrido[3,2,1-ij]quinolone (FIG. 1, compound 9) was synthesized as follows. A flame-dried round-bottom flask was charged with compound 8 (5.0 g, 19.8 mmol, 1.0 eq., FIG. 1) and anhydrous $CH_2Cl_2$ (200 mL). $AlCl_3$ (3.17 g, 23.8 mmol, 1.2 eq.) was added to the reaction in one portion. The resultant mixture was sonicated under a nitrogen atmosphere for 30 min. A solution of compound 8 (6.07 g, 25.8 mmol, 1.4 eq., FIG. 1) in anhydrous $CH_2Cl_2$ (7.0 mL) was transferred to the reaction via dropwise syringe addition. After overnight stirring at room temperature, the reaction was quenched by slow addition of sat. $NaHCO_3$ (~200 mL) and filtered through a bed of celite which was washed with $CH_2Cl_2$ (100 mL). The aqueous phase was separated and extracted with $CH_2Cl_2$ (3×100 mL). The combined organic fractions were washed with brine (100 mL), dried ($Na_2SO_4$), filtered, and concentrated under reduced pressure. The crude product was purified via flash chromatography on a silica column (4:96 v/v EtOAc:Hexanes) to afford the title compound as a brown oil. (2.71 g, 6.0 mmol, 30.0% yield). Unreacted compound 8 (FIG. 1) was recovered via flash chromatography on a silica column. $^1H$ NMR (500 MHz, $CDCl_3$) δ 7.18 (d, J=2.6 Hz, 1H), 6.93 (d, J=8.5 Hz, 1H), 6.79 (dd, J=8.5, 2.6 Hz, 1H), 6.51 (s, 1H), 4.04 (s, 2H), 3.80 (s, 3H), 3.22-3.13 (m, 2H), 3.13-3.08 (m, 2H), 2.86 (t, J=6.7 Hz, 2H), 2.67 (t, J=6.6 Hz, 2H), 2.07-2.00 (m, 2H), 2.00-1.94 (m, 2H). $^{13}C$ NMR (125 MHz, $CDCl_3$) δ 158.6, 143.4, 132.3, 131.1, 128.9, 126.5, 125.9, 125.2, 121.6, 121.0, 118.0, 113.7, 55.7, 50.3, 49.8, 41.4, 29.7, 27.8, 22.5, 22.2. IR (neat): 3006, 2938, 2834, 1488, 1458, 1441, 1331, 1305, 1283, 1233, 1205, 1183, 1037, 858, 751, 725, 667, 547, 463 $cm^{-1}$. HR-MS calculated for $C_{20}H_{21}Br_2NO$ $[M+H]^+$ m/z 450.0068. found 450.0055.

12-methoxy-14,14-dimethyl-2,3,6,7,9,14-hexahydro-1H,5H-benzo[5,6]silino[2,3-f]pyrido[3,2,1-ij]quinoline 12-methoxy-14,14-dimethyl-2,3,6,7,9,14-hexahydro-1H,5H-benzo[5,6]silino[2,3-f]pyrido[3,2,1-ij]quinolone (FIG. 1, compound 10) was synthesized as follows. A flame-dried round-bottom flask was charged with compound 9 (2.71 g, 6.0 mmol, 1.0 eq., FIG. 1) and anhydrous THF (100 mL). An oven-dried addition funnel was attached to the flask and the system was flushed with nitrogen. The reaction was cooled to −78° C. and treated with 1.4 M sec-butyllithium in cyclohexane (12.9 mL, 18.0 mmol, 3.0 eq.) via funnel addition over 30 min. After stirring at the same temperature for 10 min, a solution of $SiMe_2Cl_2$ (1.36 mL, 11.5 mmol, 1.9 eq.) in anhydrous THF (11.5 mL) was added dropwise over 20 min. The reaction was warmed to room temperature and stirred overnight. The volatiles were removed under reduced pressure to obtain the crude product which was washed with sat. $NaHCO_3$ (100 mL) and extracted with $CH_2Cl_2$ (3×50 mL). The combined organic fractions were washed with brine (100 mL), dried ($Na_2SO_4$), filtered, and concentrated under reduced pressure to afford the title compound as a brown oil which was sufficiently pure to use without further purification. $^1H$ NMR (400 MHz, $CDCl_3$) δ 7.23 (d, J=8.3 Hz, 1H), 7.17 (d, J=2.7 Hz, 1H), 6.88 (dd, J=8.3, 2.7 Hz, 1H), 6.85 (s, 1H), 4.00 (s, 2H), 3.86 (s, 3H), 3.16 (s, 2H), 2.99 (s, 2H), 2.81 (s, 1H), 2.20-1.96 (m, 4H), 0.56 (d, T=1.3 Hz, 4H). $^{13}C$ NMR (100 MHz, $CDCl_3$) δ 157.5, 141.4, 138.6, 137.4, 134.2, 131.3, 128.6, 127.9, 127.7, 123.9, 118.6, 114.3, 55.5, 50.8, 50.2, 40.3, 29.9, 28.2, 22.9, 22.4, −0.4. IR (neat): 2933, 2833, 1682, 1596, 1548, 1304, 1246, 1039, 820, 768, 649, 453 $cm^{-1}$. HR-MS calculated for $C_{22}H_{27}NOSi$ $[M+H]^+$ m/z 350.1940. found 350.1940.

12-Methoxy-14,14-dimethyl-2,3,5,6,7,14-hexahydro-1H,9H-benzo[5,6]silino[2,3-f]pyrido[3,2,1-ij]quinolin-9-one 12-Methoxy-14,14-dimethyl-2,3,5,6,7,14-hexahydro-1H,9H-benzo[5,6]silino[2,3-f]pyrido[3,2,1-ij]quinolin-9-one (FIG. 1, compound 1) was synthesized as follows. A round-bottom flask was charged with compound 10 (2.1 g, 6.0 mmol, 1.0 eq., FIG. 1), $Cs_2CO_3$ (5.9 g, 18.0 mmol, 3.0 eq.), and DMSO (20 mL). The reaction mixture was heated at 90° C. with the flask open to the atmosphere for 3 days. After cooling to room temperature, the reaction was diluted with $CH_2Cl_2$ (50 mL) and filtered through a bed of celite. The filtrate was diluted with brine (150 mL) and extracted with $CH_2Cl_2$ (3×100 mL). The combined organic fractions were washed with brine (100 mL), dried ($Na_2SO_4$), filtered, and concentrated under reduced pressure. The crude product was purified via flash chromatography on a silica column to afford the title compound as a yellow powder (412 mg, 1.1 mmol, 18.3% yield over two-steps beginning from compound 3, FIG. 1). $^1H$ NMR (400 MHz, $CDCl_3$) δ 8.43 (d, J=8.9 Hz, 1H), 8.09 (s, 1H), 7.08 (d, J=2.8 Hz, 1H), 7.02 (dd, J=8.9, 2.8 Hz, 1H), 3.90 (s, 3H), 3.30 (m, 4H), 2.93 (t, J=6.3 Hz, 2H), 2.83 (t, J=6.4 Hz, 2H), 2.13-1.88 (m, 4H), 0.53 (s, 6H). $^{13}C$ NMR (100 MHz, $CDCl_3$) δ 185.7, 170.6, 161.8, 145.7, 142.2, 135.4, 134.2, 131.9, 130.6, 128.6, 124.8, 123.1, 117.6, 115.1, 55.5, 50.6, 50.1, 29.1, 28.4, 22.0, 21.7, −0.1. m.p.=130° C. (decomp). IR (neat): 3012, 2972, 1739, 1585, 1366, 1231, 834, 765 $cm^{-1}$. HR-MS calculated for $C_{22}H_{25}NO_2Si$ $[M+H]^+$ m/z 364.1733. found 364.1740.

Synthesis of 5-Bromo-1,6-dimethyl-1H-indole

Methyl (4-bromo-3-methylphenyl)carbamate

Figure 2:
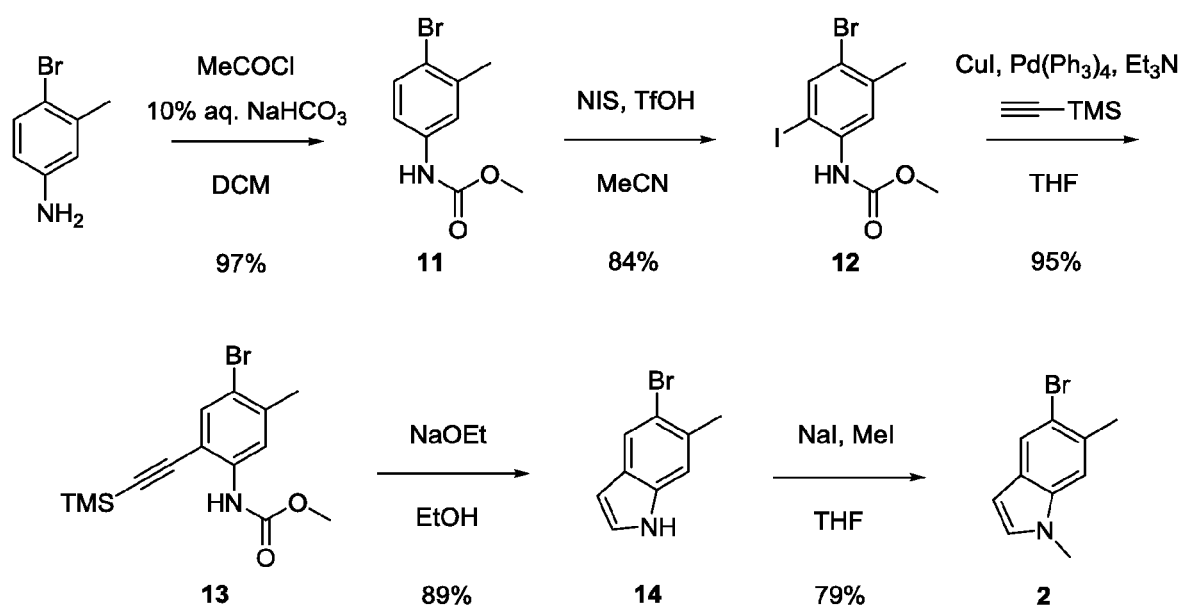
FIG. 2 depicts a schematic showing the synthesis of 5-Bromo-1,6-dimethyl-1H-indole.

Methyl (4-bromo-3-methylphenyl)carbamate (FIG. 2, compound 11) was synthesized as follows. A solution of 4-bromo-3-methylaniline (5.25 g, 28.2 mmol, 1.0 eq.), $CH_2Cl_2$ (50 mL), and 10% aq. $NaHCO_3$ (40 mL) was cooled in an ice-bath. Methyl chloroformate (4.0 mL, 51.8 mmol, 1.8 eq.) was added dropwise to the rapidly stirred solution. The reaction was subsequently warmed to room temperature and stirred for 2 hrs. The reaction was then diluted with $CH_2Cl_2$ (50 mL) and sequentially washed with sat. $NH_4Cl$ (50 mL), sat. $NaHCO_3$ (50 mL) and brine (50 mL). The organic fraction was dried ($Na_2SO_4$), filtered and concentrated to afford the crude residue as a brown solid which was purified via flash chromatography on a silica column (1:1 v/v EtOAc:Hexanes) to afford the title compound as a white solid (6.65 g, 27.3 mmol, 96.6% yield). $^1H$ NMR (500 MHz, $CDCl_3$) δ 7.39 (d, J=8.6 Hz, 1H), 7.28 (s, 1H), 7.18 (s, 1H), 7.12 (d, J=8.6 Hz, 1H), 3.75 (s, 3H), 2.31 (s, 3H). $^{13}C$ NMR (125 MHz, $CDCl_3$) δ 154.5, 138.7, 137.4, 132.8, 121.3, 118.8, 118.1, 77.7, 77.4, 77.2, 52.7, 23.2. m.p.=71-72° C. IR (neat): 3328, 1705, 1584, 1275, 1233, 1071, 1023, 826, 765, 679, 653 $cm^{-1}$. HR-MS calculated for $C_9H_{10}BrNO_2$ $[M+1]^+$ m/z 243.9973. found 243.9977.

Methyl (4-bromo-2-iodo-5-methylphenyl)carbamate

Methyl (4-bromo-2-iodo-5-methylphenyl)carbamate (FIG. 2, compound 12) was synthesized as follows. A solution of compound 11 (32.0 g, 131.1 mmol, 1.0 eq., FIG. 2) in MeCN (150 mL) was cooled to 0° C. in an ice-bath.

N-iodosuccinimide (30.1 g, 137.6 mmol, 1.05 eq.) was added in one portion to the stirred solution. Trifluoromethanesulfonic acid (1.2 mL, 13.1 mmol, 0.1 eq.) was then added dropwise. The reaction was subsequently warmed to room temperature and stirred overnight. After overnight stirring, the resulting white solid was filtered, washed with cold MeCN, and dried under reduced pressure (42.2 g, 110.1 mmol, 84.0% yield). The compound was used in the next step without further purification. $^1$H NMR (500 MHz, CDCl$_3$) δ 7.94 (s, 1H), 7.85 (s, 1H), 6.87 (s, 1H), 3.80 (s, 3H), 2.35 (s, 3H). $^{13}$C NMR (125 MHz, CDCl$_3$) δ 153.9, 141.0, 139.5, 137.8, 121.9, 119.5, 85.5, 52.9, 23.3. m.p. 130-131° C. IR (neat): 3276, 2939, 1690, 1603, 1491, 1275, 1241, 1042, 873, 863, 772, 606 cm$^{-1}$. HR-MS calculated for C$_9$H$_{10}$BrINO$_2$ [M+H]$^+$ m/z 369.8940. found 369.8945.

Methyl (4-bromo-5-methyl-2-((trimethylsilyl)ethynyl)phenyl)carbamate

Methyl (4-bromo-5-methyl-2-((trimethylsilyl)ethynyl) phenyl)carbamate (FIG. 2, compound 13) was synthesized as follows. A flame-dried round-bottom flask was charged with compound 12 (5.38 g, 14.5 mmol, 1.0 eq., FIG. 2), CuI (0.28 g, 1.5 mmol, 0.1 eq.), and Pd(PPh$_3$)$_4$ (0.84 g, 0.7 mmol, 0.05 eq.) and then dried under vacuum for 30 min. The solids were then dissolved in anhydrous THF (35 mL) and treated sequentially with trimethylsilylacetylene (2.3 mL, 16.0 mmol, 1.1 eq.) and anhydrous triethylamine (8.1 mL, 58.2 mmol, 4.0 eq.). The reaction was stirred at room temperature for 1 hr. All volatiles were removed under reduced pressure and the resultant residue was dissolved in EtOAc (50 mL) and washed with brine (3×50 mL). The organic fraction was dried (Na$_2$SO$_4$), filtered and concentrated to afford the crude product as a dark brown solid which was purified via flash chromatography on a silica column (3:97 v/v EtOAc:Hexanes) to afford the title compound as an orange solid (4.72 g, 13.9 mmol, 95.4% yield). $^1$H NMR (500 MHz, CDCl$_3$) δ 7.94 (s, 1H), 7.39 (s, 1H), 7.24 (s, 1H), 3.71 (s, 3H), 2.28 (s, 3H), 0.24 (s, 9H). $^{13}$C NMR (125 MHz, CDCl$_3$) δ 153.4, 140.0, 138.7, 134.6, 119.4, 117.0, 110.6, 102.6, 99.0, 52.5, 23.6, 0.1. m.p.=73-74° C. IR (neat): 3394, 2959, 2150, 1740, 1509, 1220, 1070, 863, 839, 762, 574 cm$^{-1}$. HR-MS calculated for C$_{14}$H$_{18}$BrNO$_2$Si [M+Na]$^+$ m/z 362.0182. found 362.0193.

5-Bromo-6-methyl-1H-indole

5-Bromo-6-methyl-/H-indole (FIG. 2, compound 14) was synthesized as follows. To a freshly prepared, 0.7 M sodium ethoxide solution (150 mL, 8.0 eq.) was added compound 13 (4.5 g, 13.3 mmol, 1.0 eq., FIG. 2) The reaction was stirred at 80° C. until all starting material was consumed and then the solvent was removed under reduced pressure. The residue was dissolved in CH$_2$Cl$_2$ (50 mL) and washed with brine (3×50 mL). The organic fraction was dried (Na$_2$SO$_4$), filtered and concentrated to afford the crude residue as a dark brown solid which was purified via flash chromatography on a silica column (3:17 v/v EtOAc:Hexanes) to afford the title compound as a yellow solid (2.48 g, 11.8 mmol, 88.8% yield). $^1$H NMR (500 MHz, CDCl$_3$) δ 8.03 (bs, NH), 7.88 (s, 1H), 7.26 (s, 1H), 7.16 (t, 1H), 6.52-6.48 (m, 1H), 2.54 (s, 3H). $^{13}$C NMR (125 MHz, CDCl$_3$) δ 135.5, 131.0, 128.0, 125.0, 124.0, 116.7, 112.7, 102.1, 23.8. m.p.=85-86° C. IR (neat): 2916, 1738, 1614, 1577, 1506, 1467, 1415, 1315, 1270, 1241, 1202, 964, 881, 842, 761, 730, 692 cm$^{-1}$. HR-MS calculated for C$_9$H$_8$BrN [M+H]$^+$ m/z 209.9918, found 209.9915.

5-Bromo-1,6-dimethyl-1H-indole

5-Bromo-1,6-dimethyl-1H-indole (FIG. 2, compound 2) was synthesized as follows. A flame-dried round-bottom flask was charged with compound 14 (5.41 g, 25.8 mmol, 1.0 eq., FIG. 2) and anhydrous THF (50 mL). The solution was cooled in an ice-bath and treated with NaH as a 60% dispersion in mineral oil (1.24 g, 30.9 mmol, 1.2 eq.) and methyl iodide (3.2 mL, 51.5 mmol, 2.0 eq.). After stirring at 0° C. for 2 hrs, the volatiles were removed under reduced pressure. The residue was dissolved with CH$_2$Cl$_2$ (100 mL) and washed with brine (50 mL). The organic fraction was (Na$_2$SO$_4$), filtered and concentrated to afford the crude product which was purified via flash chromatography on a silica column (7:193 v/v EtOAc:Hexanes) to afford the title compound as a yellow solid (4.56 g, 20.3 mmol, 79.1% yield). $^1$H NMR (500 MHz, Acetone-d$_6$) δ 10.27 (bs, NH), 7.82 (s, 1H), 7.41 (s, 1H), 7.31 (dd, J=3.2, 2.4 Hz, 1H), 6.45 (td, J=2.1, 1.0 Hz, 1H), 2.48 (d, J=0.8 Hz, 3H). $^{13}$C NMR (125 MHz, Acetone-d$_6$) δ 136.1, 129.7, 128.5, 126.0, 123.5, 115.6, 113.2, 101.1, 23.1. m.p.=90-91° C. IR (neat): 33143118, 3095, 1467, 1338 1753, 1705, 1614, 1507, 1468, 1270, 993, 881, 842, 730, 693, 606 cm'. HR-MS calculated for C$_{10}$H$_{10}$BrN [1\4+H]$^+$ m/z 224.0075. found 224.0079.

Synthesis of FP1

Figure 3:
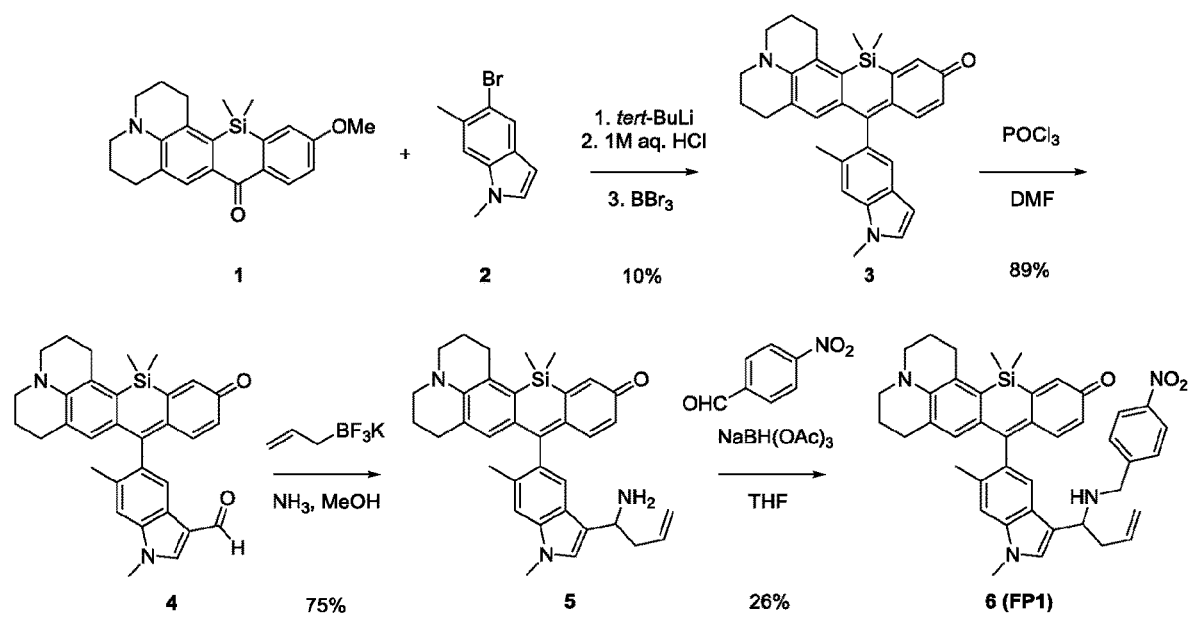
FIG. 3 depicts a schematic showing the synthesis of Formaldehyde Probe 1 (FP1).

9-(1,6-dimethyl-1H-indol-5-yl)-14,14-dimethyl-2,3,5,6,7,14-hexahydro-1H, 12H-benzo[5,6]silino [2,3-f]pyrido [3,2,1-ij]quinolin-12-one 9-(1,6-dimethyl-1H-indol-5-yl)-14,14-dimethyl-2,3,5,6,7,14-hexahydro-1H,12H-benzo[5,6]silino[2,3-f]pyrido[3,2,1-ij]quinolin-12-one (FIG. 3, compound 3) was synthesized as follows. A solution of compound 2 (2.77 g, 12.4 mmol, 8.0 eq., FIG. 3) in 25 mL anhydrous THF was cooled to −78° C. and treated with a solution of tert-butyllithium in pentane (7.27 mL, 12.4 mmol, 8.0 eq.) which was added dropwise. The reaction was stirred at the same temperature for 8 min and then treated with a solution of compound 1 (556 mg, 1.5 mmol, 1.0 eq., FIG. 3) in anhydrous THF (15 mL). The reaction was warmed to room temperature and stirred for 3 hrs. The reaction was quenched by the addition of 10% aq. HCl (10 mL) and stirred at room temperature for 1 hr. The reaction was poured into sat. NaHCO$_3$ (25 mL) and extracted with CH$_2$Cl$_2$ (3×50 mL). The combined organic fractions were dried (Na$_2$SO$_4$), filtered, and concentrated under reduced pressure. The crude residue was eluted through a silica plug and concentrated to afford a blue film which was used without further purification. A solution of this intermediate in 20 mL anhydrous CH$_2$Cl$_2$ was cooled to 0° C. and treated with a solution of 1 M BBr$_3$ in CH$_2$Cl$_2$ (2.6 mL, 2.6 mmol, 6.0 eq.) which was added dropwise. The reaction was warmed to room temperature, stirred for 2 hrs, and then quenched by addition of sat. NaHCO$_3$ (100 mL) and extracted with CH$_2$Cl$_2$ (3×50 mL). The combined organic fractions were dried (Na$_2$SO$_4$), filtered, and concentrated under reduced pressure. The crude residue was purified by flash chromatography on a silica column (8:92 v/v MeOH/CH$_2$Cl$_2$) to afford the title compound as a blue film (45 mg, 0.1 mmol, 10% yield over two-steps beginning from compound 2 (FIG. 3). $^1$H NMR (500 MHz, CDCl$_3$) δ 7.30 (s, 1H), 7.23 (s, 1H), 7.08 (d, J=3.1 Hz, 1H), 6.88 (d, J=2.3 Hz, 1H), 6.84 (d, J=9.9 Hz, 1H), 6.57 (s, 1H), 6.44 (d, J=3.1 Hz, 1H), 6.20 (dd, J=9.9, 2.3 Hz, 1H), 3.85 (s, 3H), 3.35 (t, J=5.9 Hz, 2H), 3.30 (dt, J=5.7, 2.9 Hz, 2H), 2.94 (t, J=6.3 Hz, 2H), 2.41 (t, J=6.2 Hz, 2H), 2.18 (s, 3H), 2.05 (q, J=5.5 Hz, 2H), 1.84 (q, J=6.1 Hz, 2H), 0.56 (d, J=5.7 Hz, 6H). $^{13}$C NMR (125 MHz, CDCl$_3$) δ 183.4, 162.3, 148.1, 145.5, 142.2, 136.9, 136.7, 136.1, 133.9, 132.3, 130.1, 129.2, 129.2, 128.7, 127.3, 126.2, 125.6, 122.0, 121.6, 109.9, 109.9, 100.8, 50.9, 50.3, 33.1, 29.9, 29.2, 28.1, 21.7, 21.2, 20.4, 0.0. IR (neat): 2924, 1612, 1578, 1509, 1228, 1210, 833, 765, 677, 556, 469 cm$^{-1}$. HR-MS calculated for C$_{31}$H$_{33}$N$_2$OSi [M+H]$^+$ m/z 477.2362. found 477.2365.

5-(14,14-dimethyl-12-oxo-2,3,6,7,12,14-hexahydro-1H,5H-benzo[5,6]silino[2,3-f]pyrido[3,2,1-ij]quinolin-9-yl)-1,6-dimethyl-1H-indole-3-carbaldehyde 5-(14,14-dimethyl-12-oxo-2,3,6,7,12,14-hexahydro-1H,5H-benzo [5,6]silino [2,3-f]pyrido[3,2,1-ij]quinolin-9-yl)-1,6-dimethyl-1H-indole-3-carbaldehyde (FIG. 3, compound 4) was synthesized as follows. Anhydrous DMF (3.0 mL) was cooled in an ice-bath and treated with dropwise addition of POCl$_3$ (10 uL, 0.11 mmol, 1.5 eq.). After 30 min, a solution of compound 3 (32 mg, 0.07 mmol, 1.0 eq., FIG. 3) in anhydrous DMF (2.0 mL) was added. The reaction was stirred 0° C. for 1 hr. The reaction was then syringed into a second reaction vessel where anhydrous DMF (3.0 mL) was cooled in an ice-bath and treated with dropwise addition of POCl$_3$ (10 uL, 0.11 mmol, 1.5 eq.). After 30 min, reaction was treated with additional POCl$_3$ (10 uL, 0.11 mmol, 1.5 eq.) and stirred for 3 hrs. The reaction was poured in NaHCO$_3$ (50 mL) and extracted with EtOAc (4×30 mL). The combined organic fractions were dried (Na$_2$SO$_4$), filtered and concentrated under reduced pressure. The crude residue was purified by flash chromatography on a silica column (1:33 v/v MeOH/CH$_2$Cl$_2$) to afford the title compound as a dark blue film (30 mg, 0.06 mmol, 89.0% yield). $^1$H NMR (500 MHz, CDCl$_3$) δ 9.96 (s, 1H), 7.99 (s, 1H), 7.73 (s, 1H), 7.28 (s, 1H), 6.86 (d, J=2.3 Hz, 1H), 6.72 (dd, J=9.9, 0.8 Hz, 1H), 6.43 (s, 1H), 6.17 (dd, J=10.0, 2.3 Hz, 1H), 3.94 (s, 3H), 3.31 (dt, J=27.4, 5.9 Hz, 4H), 2.93 (dd, J=7.4, 5.1 Hz, 2H), 2.39 (dd, J=7.3, 5.2 Hz, 2H), 2.21 (s, 3H), 2.10-2.01 (m, 2H), 1.83 (p, J=6.2 Hz, 2H), 0.55 (s, 6H). $^{13}$C NMR (125 MHz, CDCl$_3$) δ 184.5, 183.8, 183.3, 147.9, 145.3, 141.6, 139.6, 138.0, 136.2, 135.6, 134.4, 132.9, 128.6, 128.2, 126.9, 126.0, 123.2, 122.6, 121.9, 118.2, 110.7, 50.8, 50.2, 34.0, 29.9, 29.2, 28.1, 21.7, 21.2, 20.5, 0.1, −0.1. IR (neat): 2927, 1737, 1574, 1353, 1301, 1203 cm$^{-1}$. HR-MS calculated for C$_{32}$H$_{32}$N$_2$O$_2$Si [M+H]$^+$ m/z 505.2311. found 505.2319.

9-(3-(1-aminobut-3-en-1-yl)-1,6-dimethyl-1H-indol-5-yl)-14,14-dimethyl-2,3,5,6,7,14-hexahydro-1H,12H-benzo[5,6]silino[2,3-f]pyrido[3,2,1-ij]quinolin-12-one 9-(3-(1-aminobut-3-en-1-yl)-1,6-dimethyl-1H-indol-5-yl)-14,14-dimethyl-2,3,5,6,7,14-hexahydro-1H,12H-benzo[5,6]silino[2,3-f]pyrido[3,2,1-ij]quinolin-12-one (FIG. 3, compound 5) was synthesized as follows. Potassium allyltrifluoroborate (17.6 mg, 0.12 mmol, 2.0 eq.) was dissolved in a 7N solution of NH$_3$ in MeOH (3.0 mL) and stirred at room temperature for 15 min. A solution of compound 4 (9 mg, 0.016 mmol, 1 eq., FIG. 3) in 7N solution of NH$_3$ in MeOH (2.0 mL) and H$_2$O (10 μL) were added sequentially to the reaction which was stirred for 16 hrs. The reaction was poured into sat. NaHCO$_3$ (50 mL) and extracted with EtOAc (4×30 mL). The combined organic fractions were dried (Na$_2$SO$_4$), filtered, and concentrated under reduced pressure. The crude residue was purified by flash chromatography on a silica column (1:19 v/v MeOH/CH$_2$Cl$_2$) to afford the title compound as a dark blue film (24 mg, 0.014 mmol, 74.5% yield). $^1$H NMR (500 MHz, MeOD/CDCl$_3$) δ 7.24 (dd, J=11.3, 8.6 Hz, 2H), 7.19 (s, 1H), 6.85-6.80 (m, 2H), 6.55 (d, J=3.6 Hz, 1H), 6.15 (ddd, J=10.1, 8.0, 2.4 Hz, 1H), 5.75-5.63 (m, 1H), 5.17-4.99 (m, 2H), 4.38 (td, J=7.0, 4.7 Hz, 1H), 3.83 (s, 3H), 3.40 (t, J=5.9 Hz, 2H), 3.35 (t, J=6.1 Hz, 2H), 2.94 (t, J=6.2 Hz, 2H), 2.74-2.66 (m, 1H), 2.61 (dd, J=14.2, 7.2 Hz, 1H), 2.43-2.31 (m, 2H), 2.14 (s, 3H), 2.09-1.98 (m, 2H), 1.88-1.78 (m, 2H), 0.55 (s, 6H). $^{13}$C NMR (125 MHz, CDCl$_3$) δ 184.4, 147.9, 144.8, 142.0, 137.4, 136.1, 136.0, 135.5, 134.7, 132.0, 131.1, 130.4, 129.0, 128.4, 127.2, 126.2, 125.7, 121.9, 119.9, 117.7, 110.0, 50.7, 50.2, 48.0, 43.7, 43.5, 33.0, 29.9, 29.2, 28.2, 21.8, 21.3, 20.4, 0.2, 0.0. IR (neat): 3012, 2972, 1739, 1585, 1366, 1231, 834, 765 cm$^{-1}$. HR-MS calculated for C$_{35}$H$_{39}$N$_3$OSi [M+H]$^+$ m/z 546.2941. found 546.2947.

FP1

FP1 (FIG. 3, compound 6) was synthesized as follows. A solution of compound 5 (120.0 mg, 0.22 mmol, 1.0 eq., FIG. 3) in anhydrous THF (10.0 mL) was cooled in an ice-bath. To the solution, 4-nitrobenzaldehyde (100 mg, 0.66 mmol, 3.0 eq.), glacial AcOH (100 μL, 1.6 mmol, 10 eq.), and sodium triacetoxyborohydride (186 mg, 0.88 mmol, 4.0 eq.) were added sequentially. The reaction was warmed to room temperature and stirred for 16 hrs. Upon completion, the reaction was poured into sat. NaHCO$_3$ (50 mL) and extracted with EtOAc (4×30 mL). The combined organic fractions were dried (Na$_2$SO$_4$), filtered, and concentrated under reduced pressure. The crude residue was purified by flash chromatography on a silica column (1:33 MeOH/CH$_2$Cl$_2$) to afford the title compound as a dark blue film. (32.0 mg, 0.057 mmol, 26.0% yield). $^1$H NMR (500 MHz, CDCl$_3$) δ 8.40 (d, J=7.8 Hz, 1H), 8.20 (d, J=8.7 Hz, 2H), 7.87 (dd, J=8.6, 6.1 Hz, 2H), 7.38 (d, J=51.2 Hz, 1H), 7.22 (s, 1H), 7.14 (d, J=23.1 Hz, 1H), 6.88 (dd, J=4.7, 2.3 Hz, 1H), 6.83 (dd, J=22.0, 10.0 Hz, 1H), 6.53 (d, J=50.1 Hz, 1H), 6.18 (ddd, J=26.9, 9.9, 2.3 Hz, 1H), 5.79 (dddt, J=17.3, 10.1, 7.1, 4.5 Hz, 1H), 5.11-4.96 (m, 2H), 4.77 (td, J=8.3, 5.5 Hz, 1H), 3.84 (d, J=5.3 Hz, 3H), 3.43-3.33 (m, 2H), 3.3-3.21 (m, 2H), 2.96 (dt, J=12.4, 5.9 Hz, 2H), 2.90-2.77 (m, 2H), 2.47-2.30 (m, 2H), 2.18 (d, J=4.6 Hz, 3H), 2.14-2.02 (m, 2H), 1.91-1.71 (m, 2H), 0.59 (d, J=7.1 Hz, 3H), 0.56 (d, J=1.8 Hz, 3H). $^{13}$C NMR (125 MHz, CDCl$_3$) δ 183.9, 157.8, 157.7, 149.0, 148.0, 145.1, 142.1, 142.0, 137.3, 136.3, 135.8, 135.74, 135.70, 135.6, 134.4, 132.3, 132.2, 130.6, 129.1, 128.6, 128.5, 127.2, 126.6, 126.5, 126.0, 125.9, 124.5, 124.2, 123.97, 123.93, 121.9, 121.8, 120.5, 120.1, 117.7, 117.5, 116.6, 116.1, 110.25, 110.21, 68.1, 67.7, 50.8, 50.7, 50.29, 50.25, 42.2, 41.6, 33.16, 33.13, 29.9, 29.2, 29.2, 28.18, 28.10, 21.7, 21.28, 21.21, 20.5, 20.4, 0.15, 0.13, 0.06, 0.04. IR: 2925, 1737, 1571, 1347, 1301, 1204 cm$^{-1}$. HR-MS calculated for C$_{42}$H$_{44}$N$_4$O$_3$Si [M+H]$^+$ m/z 681.3261. found 681.3272.

Figure 4:
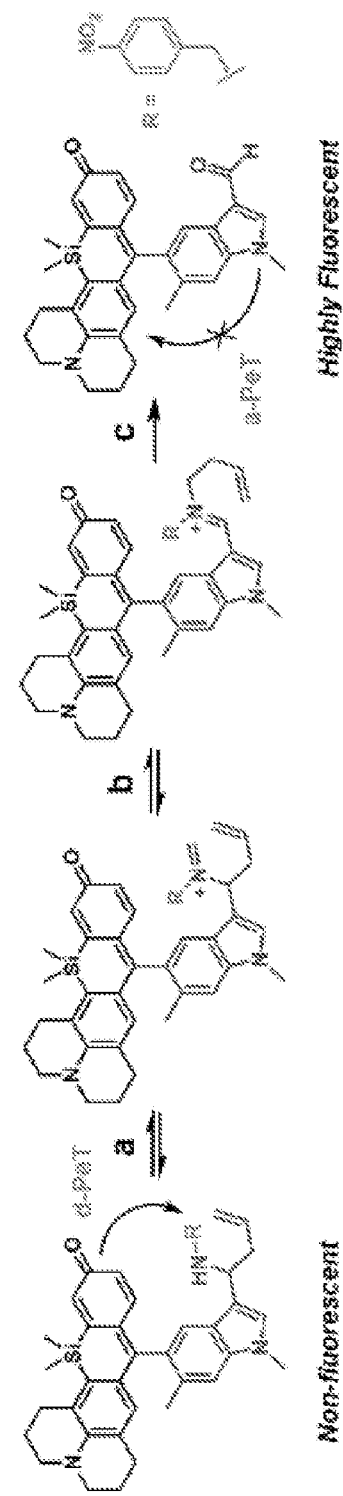
FIG. 4 illustrates use of an exemplary fluorogenic probe FP1 and a formaldehyde detection strategy based on the 2-aza-Cope sigmatropic rearrangement. The R group in red designates the 4-nitrobenzyl dark quencher moiety. Labels a, b, and c represent condensation with formaldehyde, rearrangement, and hydrolysis steps, respectively.

Example 1: A Reaction-Based Fluorescent Probe for Imaging of Formaldehyde in Living Cells The detection of formaldehyde (FA) in live cells was approached through the development of Formaldehyde Probe 1 (FP1), a FA-responsive fluorescent indicator comprised of three discrete elements; a fluorescent core (FIG. 4, in black), a FA reactive moiety (FIG. 4, in blue), and a dark quencher (FIG. 4, in red).

As such, a new julolidine-based silicon rhodol fluorescent scaffold was developed for the construction of FP1. This fluorophore exhibited an absorption maximum centered at 633 nm, which lies precisely on the 633 nm HeNe laser line commonly found in many confocal microscopes and flow cytometers. Such red-shifted fluorophores are desirable because of low autofluorescence, minimal phototoxicity, and negligible interference from biomolecules when employed in live cell imaging. FIG. 3 shows a schematic of the synthesis of FP1. In order to optimize the detection sensitivity, the design involved minimizing the background fluorescence of FP1 by appending a 4-nitrobenzyl group known to abolish fluorescence through a donor-excited PeT (d-PeT) process (Ueno et al., *J. Am. Chem. Soc.* 2006, 128:10640). Indeed, installation of this dark quencher moiety reduced the quantum efficiency ($\Phi_F$) from 0.02 for precursor 5 to undetectable levels for FP1 (Table 1). In the presence of FA, a reversible condensation event yielded an iminium intermediate which can undergo a charge-promoted [3,3]-sigmatropic rearrangement-hydrolysis sequence to expel the aryl nitro group and afford a highly fluorescent indole-3-carboxaldehyde product ($\Phi_F$=0.11) (Table 1). Of note, the aldehyde is strategically positioned at C3 such that after the reaction cascade, the N1 lone pair electrons can delocalize into the π-system rather than quench fluorescence via an acceptor-excited PeT (a-PeT) pathway. In this regard, silicon rhodol 3, without the carboxaldehyde, is non-fluorescent (Table 1).

TABLE 1 fluorescence properties of compounds 3, 4, 5 and FP1 (as denoted in FIG. 3).

| Compound | Φ | ε ($M^{-1} \cdot cm^{-1}$) | $\lambda_{abs}$ (nm) | $\lambda_{em}$ (nm) |
|---|---|---|---|---|
| 3 | ND | $8.6 \times 10^4$ | 633 | 649 |
| 4 | 0.13 | $10.6 \times 10^4$ | 633 | 649 |
| 5 | 0.02 | $10.0 \times 10^4$ | 633 | 649 |
| FP1 | ND | $2.9 \times 10^4$ | 620 | 649 |

ND means not determinable

To this end, FP1 was synthesized (FIG. 3) beginning with the reaction between indole 2 and tert-butyllithium to afford a lithium-adduct which could subsequently react with silicon xanthone 1. Silicon rhodol 3 was obtained after sequential acid-mediated dehydration and BBr3 demethylation reactions. The indole moiety was subjected to Vilsmeier-Haack formylation conditions to furnish carboxaldehyde 4 which was transformed to the homoallylic amine 5 with potassium allyltrifluoroborate in methanolic ammonia. Lastly, reductive amination with 4-nitrobenzaldehyde and triacetoxyborohydride yielded FP1.

Figure 5:
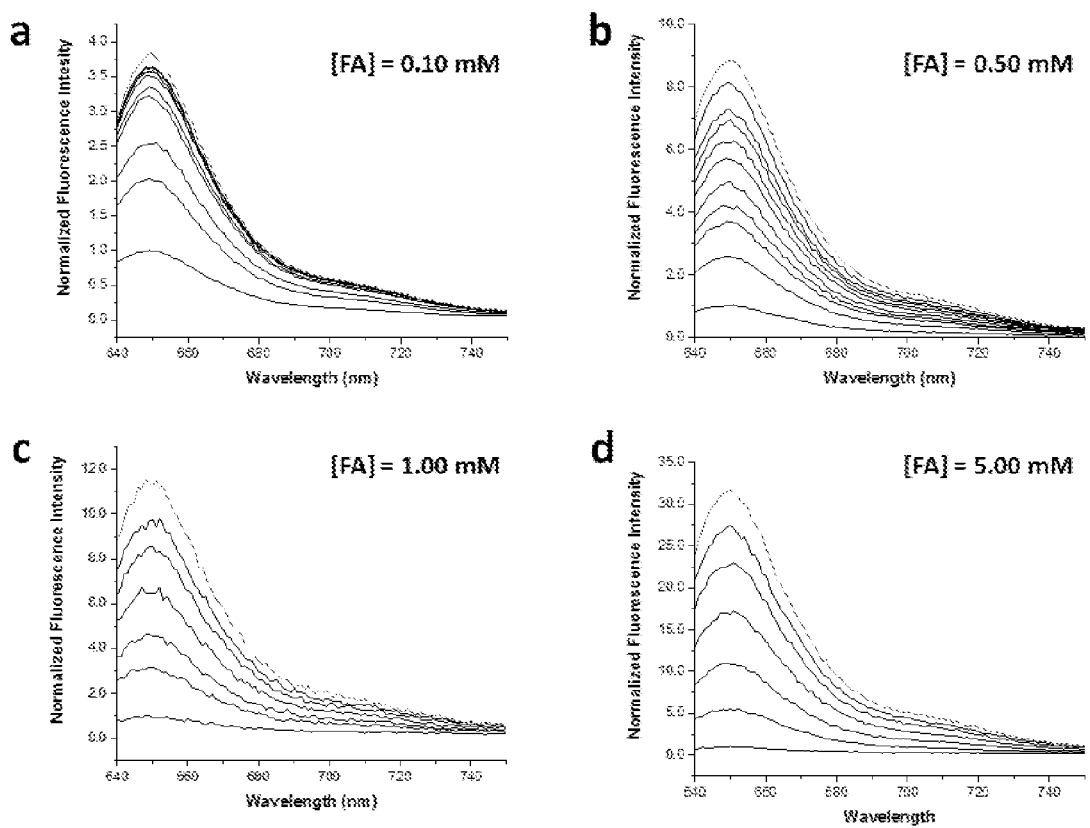
FIG. 5 depicts graphs showing normalized fluorescence emission of 1 µM FP1 in PBS (pH7.4) reacted with a) 0.1 mM, b) 0.5 mM, c) 1 mM, and d) 5 mM FA. FP1 was excited at 633 nm and the emission was collect between 640 and 750 nm. All experiments were performed at 37° C. for 3 h. Time points on graphs a-b are recorded every 15 min. The time points for graphs c-d represent every 30 min. A concentration dependent increase in fluorescence intensity was observed with a fold increase of 3.9, 8.5, 11.6, and 33.5 for 0.1 mM, 0.5 mM, 1 mM, and 5 mM FA, respectively.
Figure 6:
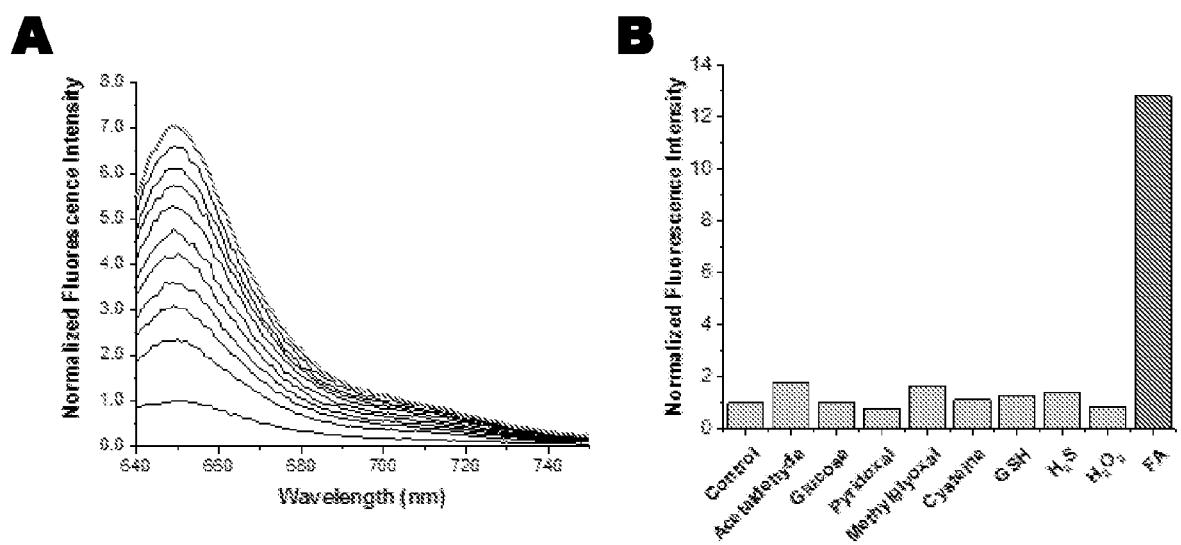
FIG. 6 depicts graphs showing.
Figure 7:
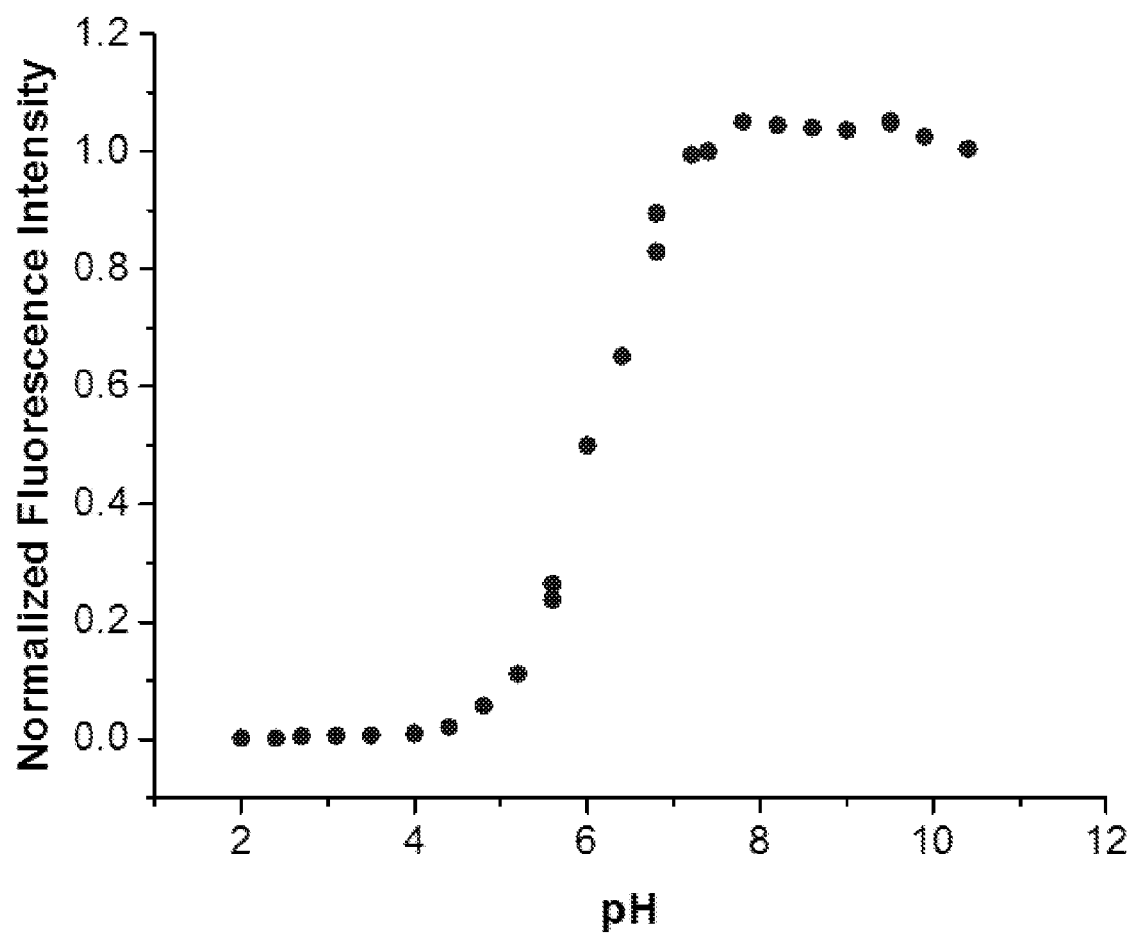
FIG. 7 depicts the pH-Fluorescence profile of compound 4 (as denoted in FIG. 3). Fluorescence intensity was measured at 25° C. for the following pH values and indicated buffers: 50 mM Glycine (2.0, 2.4, 2.7, 3.1, 3.5), 50 mM sodium acetate (4.0, 4.4, 4.8, 5.2, 5.6), 50 mM MES (5.6, 6.0, 6.4, 6.8), 50 mM HEPES (6.8, 7.2, 7.4, 7.8, 8.2), 50 mM Tris (8.2, 8.6, 9.0, 9.5) and 50 mM glycine (9.5, 9.9, 10.4). Compound 4 was excited at 633 nm and the emission was collect between 640 and 750 nm.

The fluorescence properties of FP1 in PBS buffer (pH 7.4) in response to FA was evaluated. Prior to FA treatment, a 1 μM solution of FP1 was almost non-fluorescent; however, upon addition of FA, a dose-dependent fluorescence increase was observed (FIG. 5). For example, upon treatment with 0.25 mM FA, within reported physiological levels in the brain, a ca. 7.0-fold fluorescence increase was observed after 3 hrs at 37° C. (FIG. 6A), whereas 5 mM FA triggered a larger ca. 33.5-fold enhancement (FIG. 5). Additionally, the lower limit of detection of FP1 after 3 hrs incubation at 37° C. was determined to be 0.01 mM FA using standard protocols (Little, *Biopharm. Int.* 2015, 28:48). Given the highly reactive nature of the aldehyde functionality, whether biologically relevant aldehyde containing species such as acetaldehyde, glucose, methylglyoxal, and pyridoxal would cross-react with FP1 to give false positive results, was examined. When 1 μM FP1 was reacted with 1 mM of the various analytes, only minimal cross-reactivity was observed. In the case of acetaldehyde, a 1.9-fold fluorescence increase was detected after 3 hrs (FIG. 6B). In contrast, treatment with FA at the same concentration resulted in a 12.8-fold signal enhancement. Moreover, because FP1 contains an aryl nitro group which may be reduced by thiols such as cysteine, glutathione, and hydrogen sulfide (Montoya and Pluth, *Chem. Commun.* 2012, 48:4767) to the corresponding aniline product, the chemical stability of FP1 in the presence of these intracellular reductants was examined and observed to exhibit no aberrant reactivity (FIG. 6B). In addition to its ability to crosslink biomolecules, FA is cytotoxic through the induction of oxidative stress (Zararsiz et al., *Cell Biochem. Fund.* 2007, 25:413). Thus, FP1 was reacted with 1 mM hydrogen peroxide, a common reactive oxygen species, to mimic oxidative stress in cells but found no significant change in fluorescence (FIG. 6B). The emission spectra of FP1 were recorded at a variety of pH values ranging from 2.0 to 10.4; however, owing to its weak emission, a reliable pH-fluorescence trace could not be obtained. As such, the corresponding pH-profile for carboxaldehyde 4 was constructed and noted that the high fluorescence intensity was maintained under physiological conditions (FIG. 7).

Figure 8:
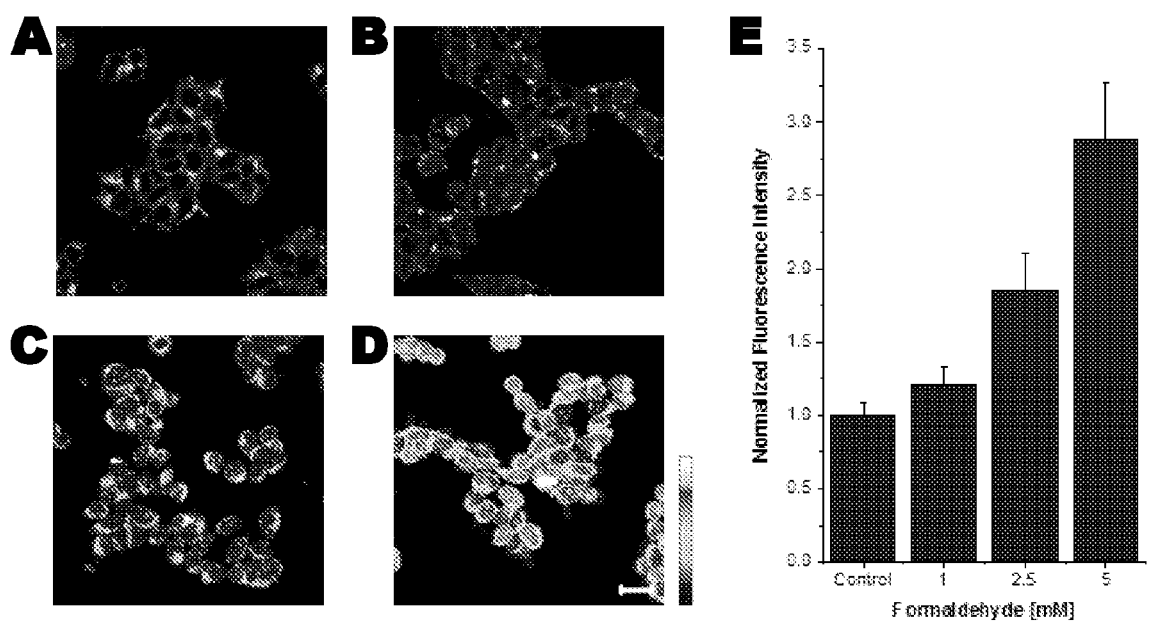
FIG. 8 depict confocal microscopy images acquired by irradiation of HEK293TN cells treated with FIG. 8A, a DMEM vehicle control.
Figure 9:
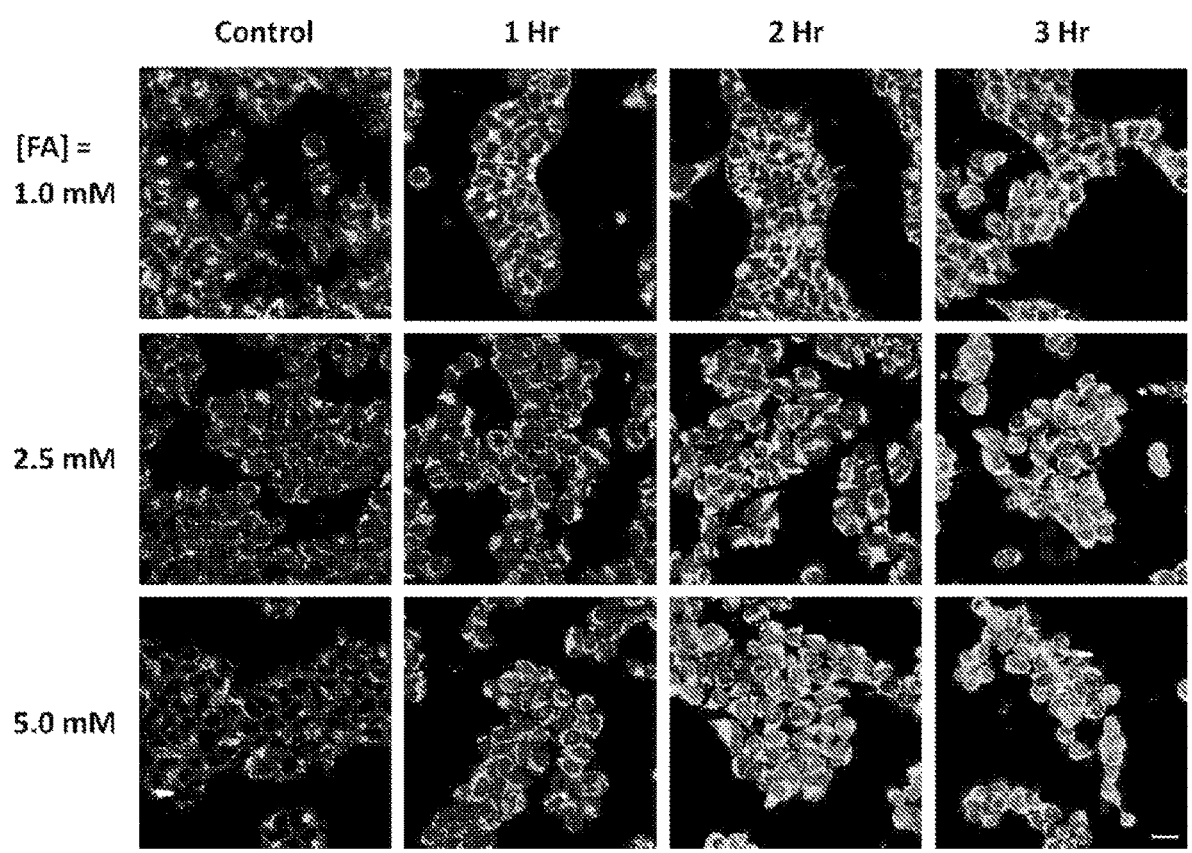
FIG. 9 depicts live-cell imaging of HEK293TN cells. Cells were stained with a solution of 2 µM FP$_1$ in serum-free DMEM for 8 min, washed with fresh DMEM to remove excess dye and then incubated with 1, 2.5, or 5 mM FA at 37° C. for 1, 2, and 3 h. Cells were irradiated with the 633 nm HeNe laser set at 3% power with a pinhole size of 1 airy unit. The emission was collected between 645 and 800 nm. Scale bar represents 20 µm. Pseudo-coloring represents intensity distribution from highest intensity indicated by white to the lowest intensity designated by black.
Figure 10:
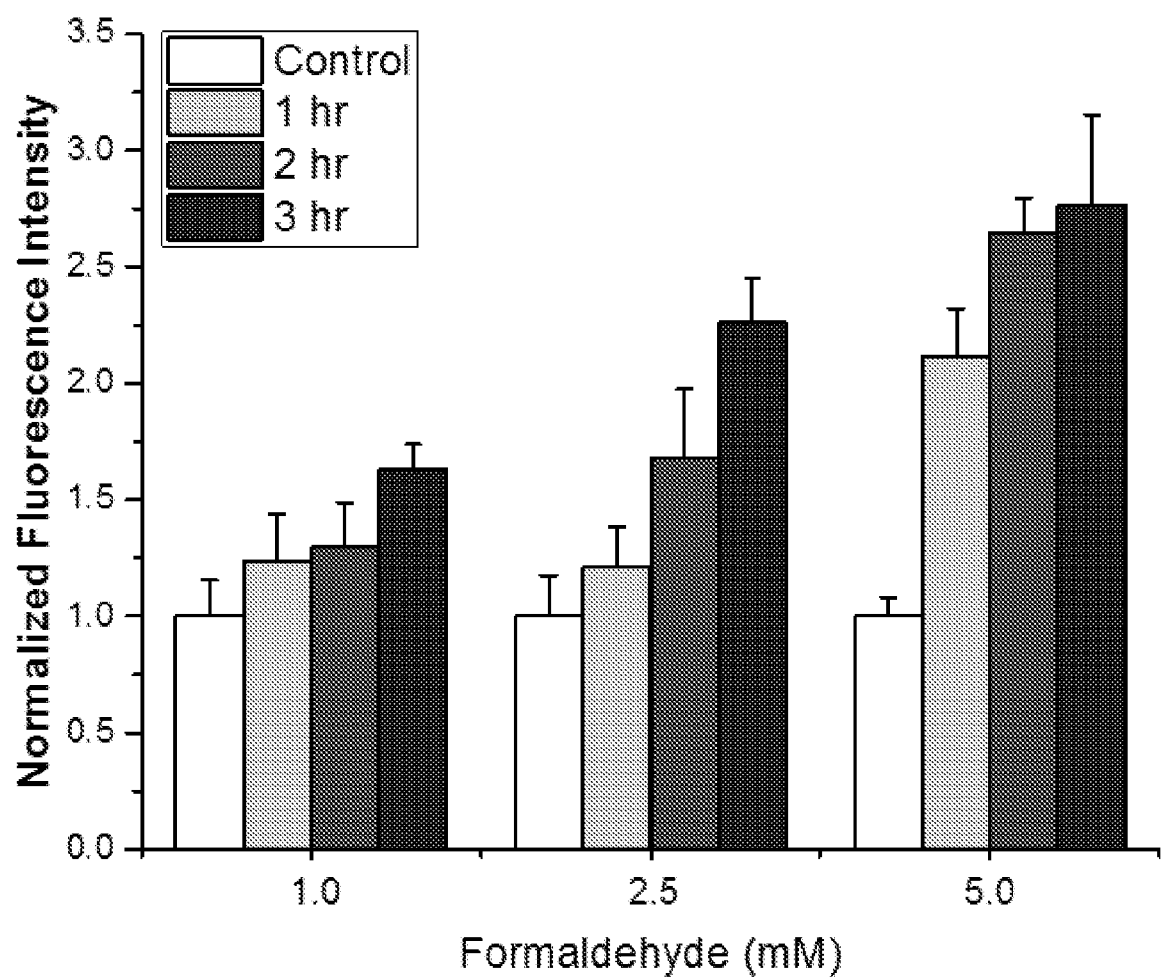
FIG. 10 depicts the quantification of observed fluorescence intensity by confocal imaging in HEK293TN cells after incubation with 1 mM, 2.5 mM or 5 mM FA for 1 (light grey bars), 2 (dark grey bars) and 3 hrs (black bars). A DMEM vehicle was added to control cells which was normalized to 1 (white bars). Cells incubated with 1 mM FA for 1, 2 and 3 hrs exhibited a 1.2-, 1.3-, and 1.6-fold increase in fluorescence intensity, respectively. Cells incubated with 2.5 mM FA for 1, 2 and 3 hrs resulted in a 1.2-, 1.7-, and 2.2-fold increase in fluorescence intensity, respectively. Cells incubated with 5 mM FA for 1, 2 and 3 hrs resulted in a 2.1-, 2.6-, and 2.8-fold increase in fluorescence intensity, respectively. For each condition, a minimum of 5 images were averaged (n>5). Errors represent standard deviation.
Figure 11:
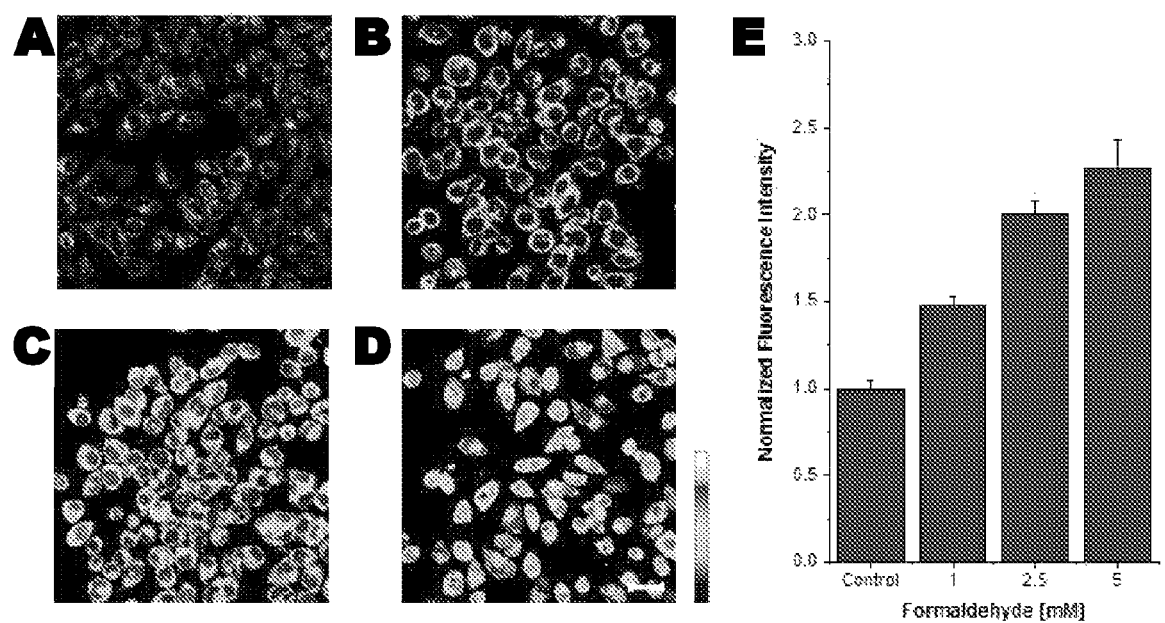
FIG. 11 depicts confocal microscopy images acquired by irradiation of NS1 cells treated with FIG. 11A, a vehicle control.
Figure 12:
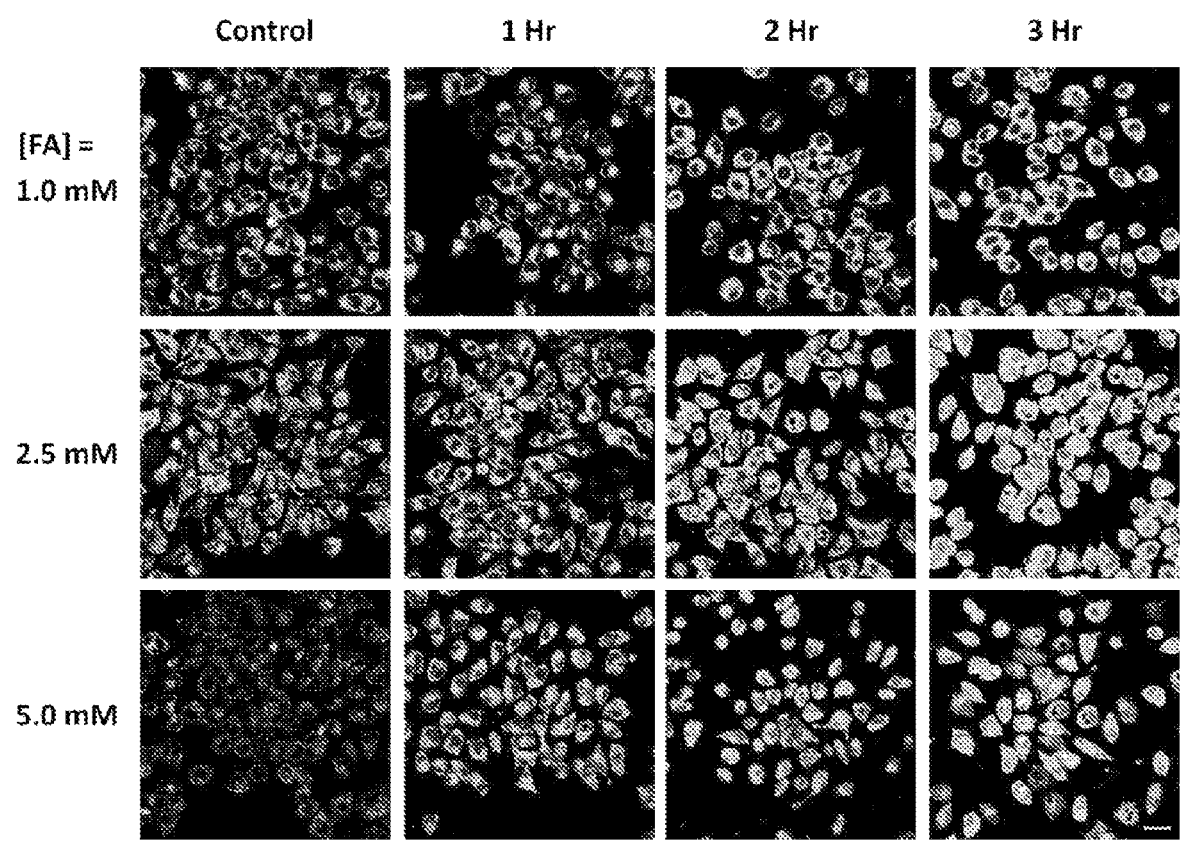
FIG. 12 depicts live-cell imaging of NS1 cells. Cells were stained with a solution of 2 µM FP$_1$ in Ham's F-12K serum-free media for 8 min, washed with fresh media to remove excess dye and then incubated with 1, 2.5, or 5 mM FA at 37° C. for 1, 2, and 3 hrs. Cells were irradiated with the 633 nm HeNe laser set at 3% power with a pinhole size of 1 airy unit. The emission was collected between 645 and 800 nm. Scale bar represents 20 µm. Pseudo-coloring represents intensity distribution from highest intensity indicated by white to the lowest intensity designated by black.
Figure 13:
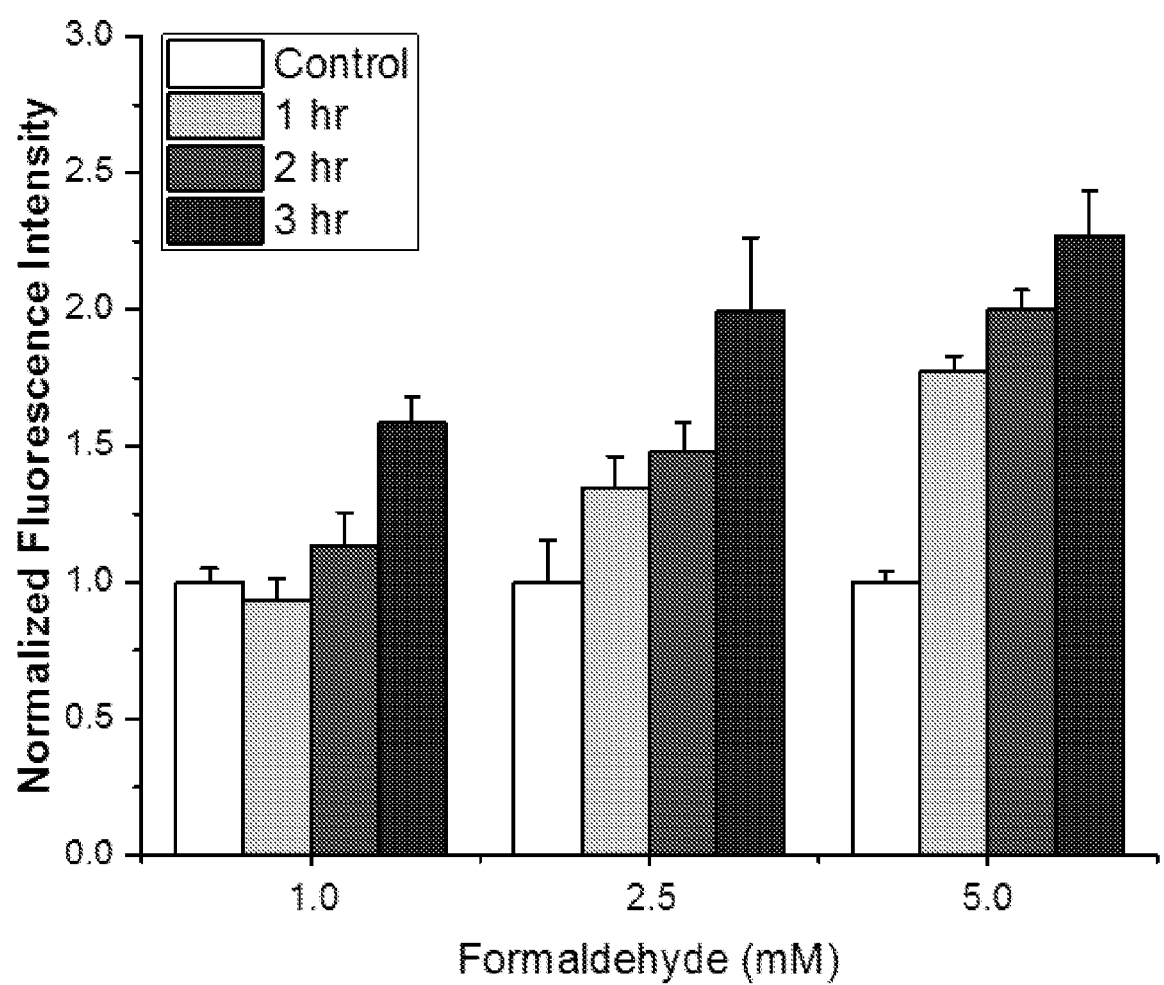
FIG. 13 depicts quantification of observed fluorescence intensity by confocal imaging in NS1 cells after incubation with 1 mM, 2.5 mM or 5 mM FA for 1 (light grey bars), 2 (dark grey bars) and 3 h (black bars). A Ham's F-12K vehicle was added to control cells which was normalized to 1 (white bars). Cells incubated with 1 mM FA for 1, 2 and 3 hrs exhibited a 0-, 1.1-, and 1.6-fold increase in fluorescence intensity, respectively. Cells incubated with 2.5 mM FA for 1, 2 and 3 hrs resulted in a 1.3-, 1.5-, and 2.0-fold increase in fluorescence intensity, respectively. Cells incubated with 5 mM FA for 1, 2 and 3 hrs resulted in a 1.8-, 2.0-, and 2.3-fold increase in fluorescence intensity, respectively. For each condition, a minimum of 5 images were averaged (n>5). Errors represent standard deviation.
Figure 14A:
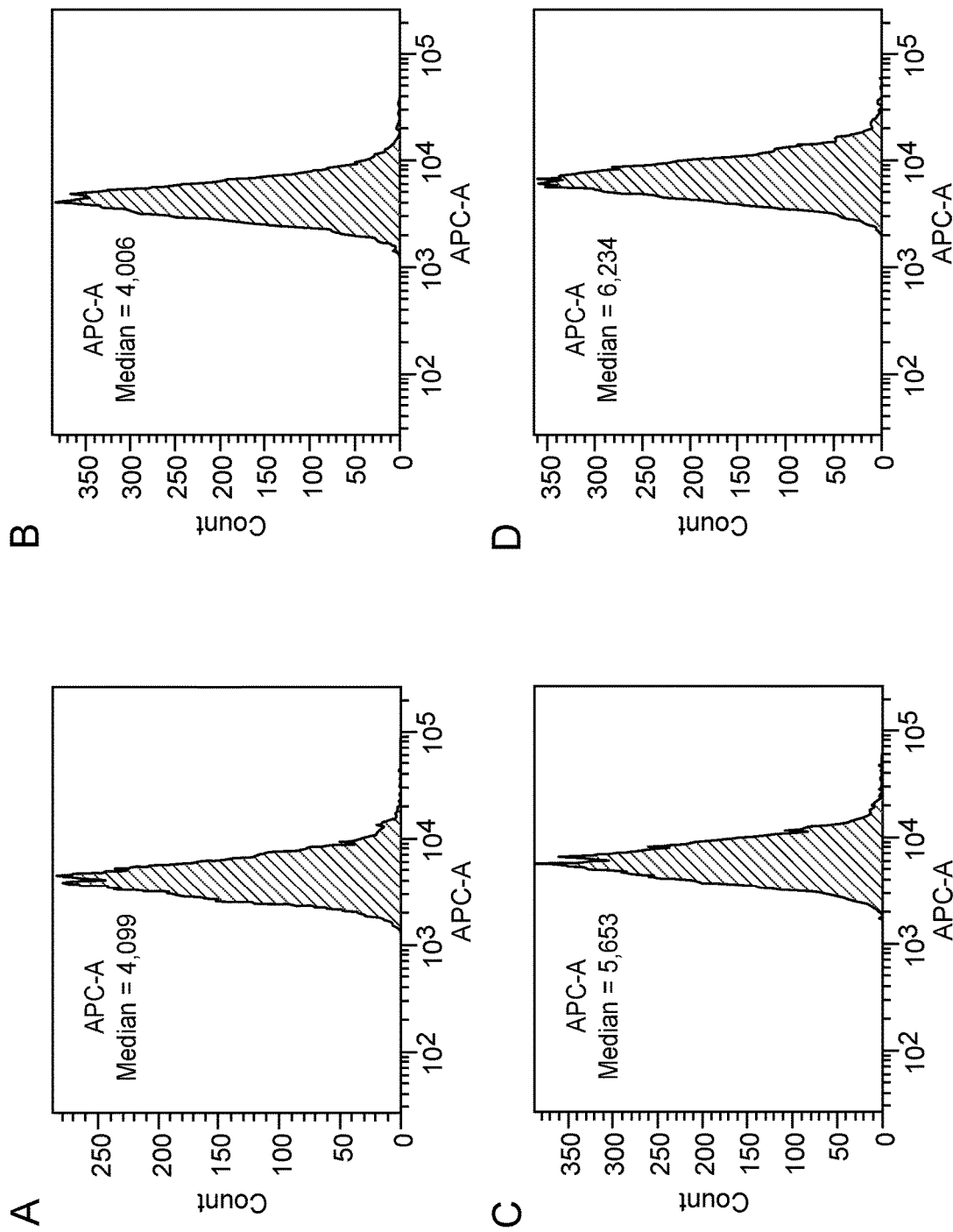
FIG. 14A-14B depict flow cytometry analyses.
Figure 14A:
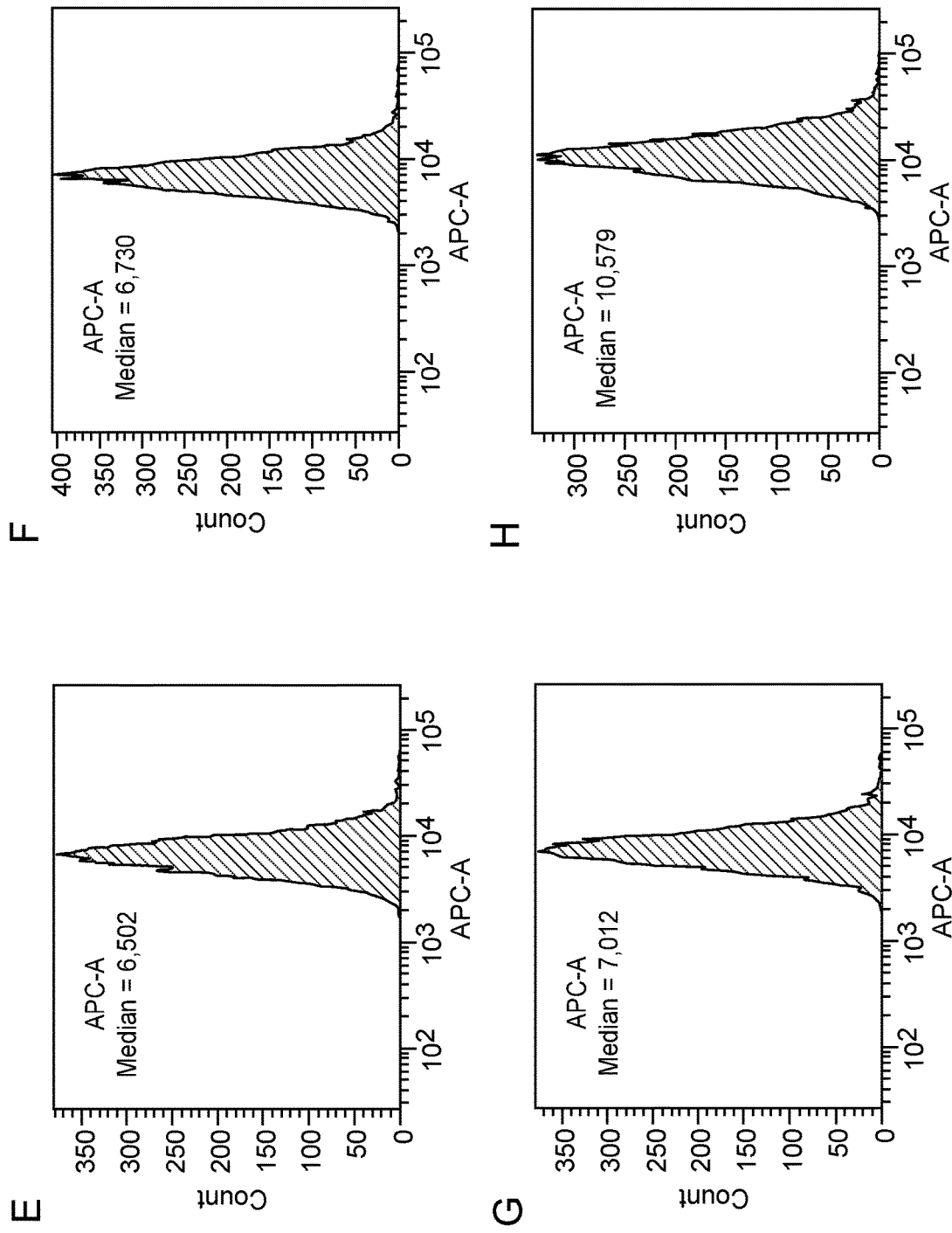
Figure 14A:
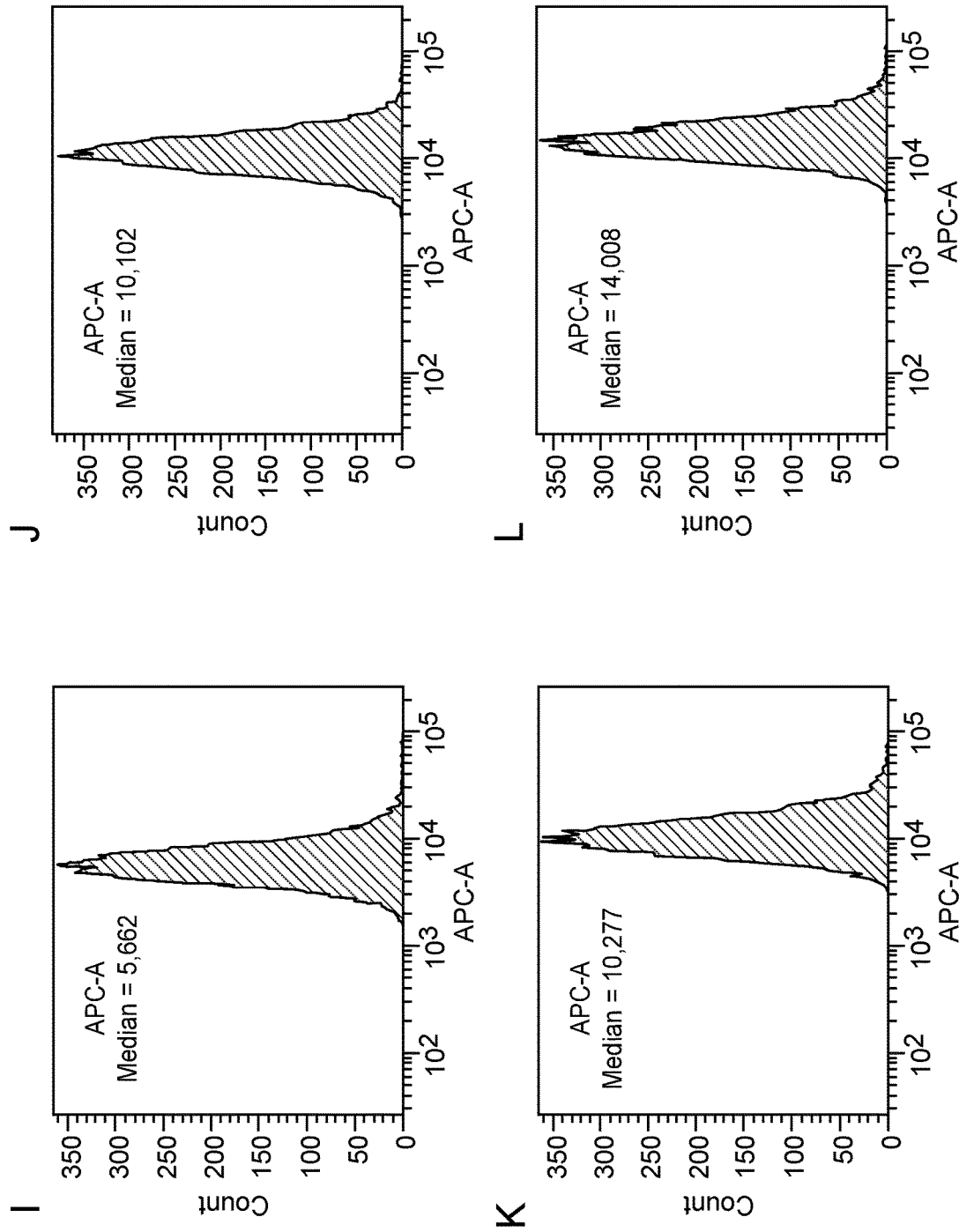
Figure 14B:
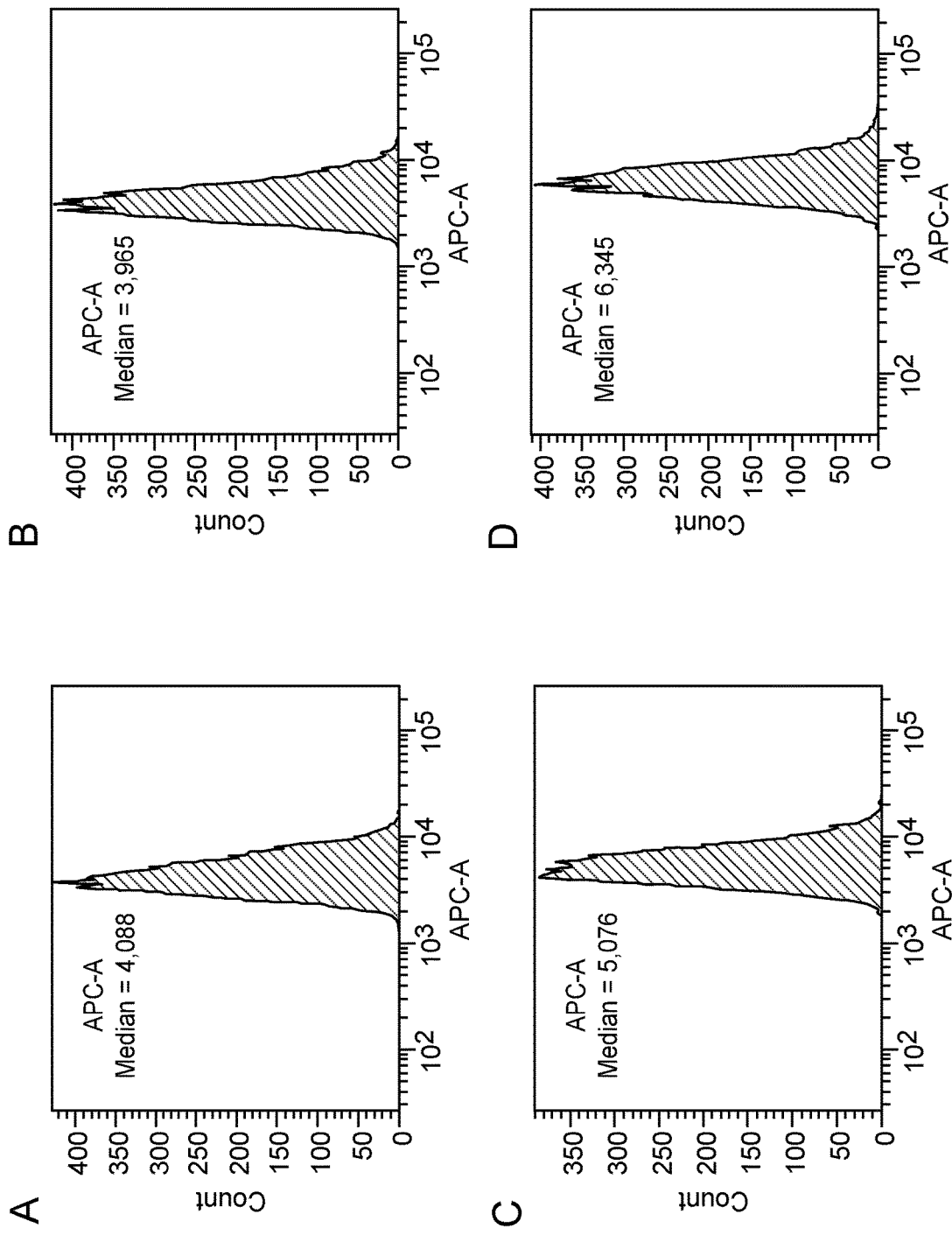
Figure 14B:
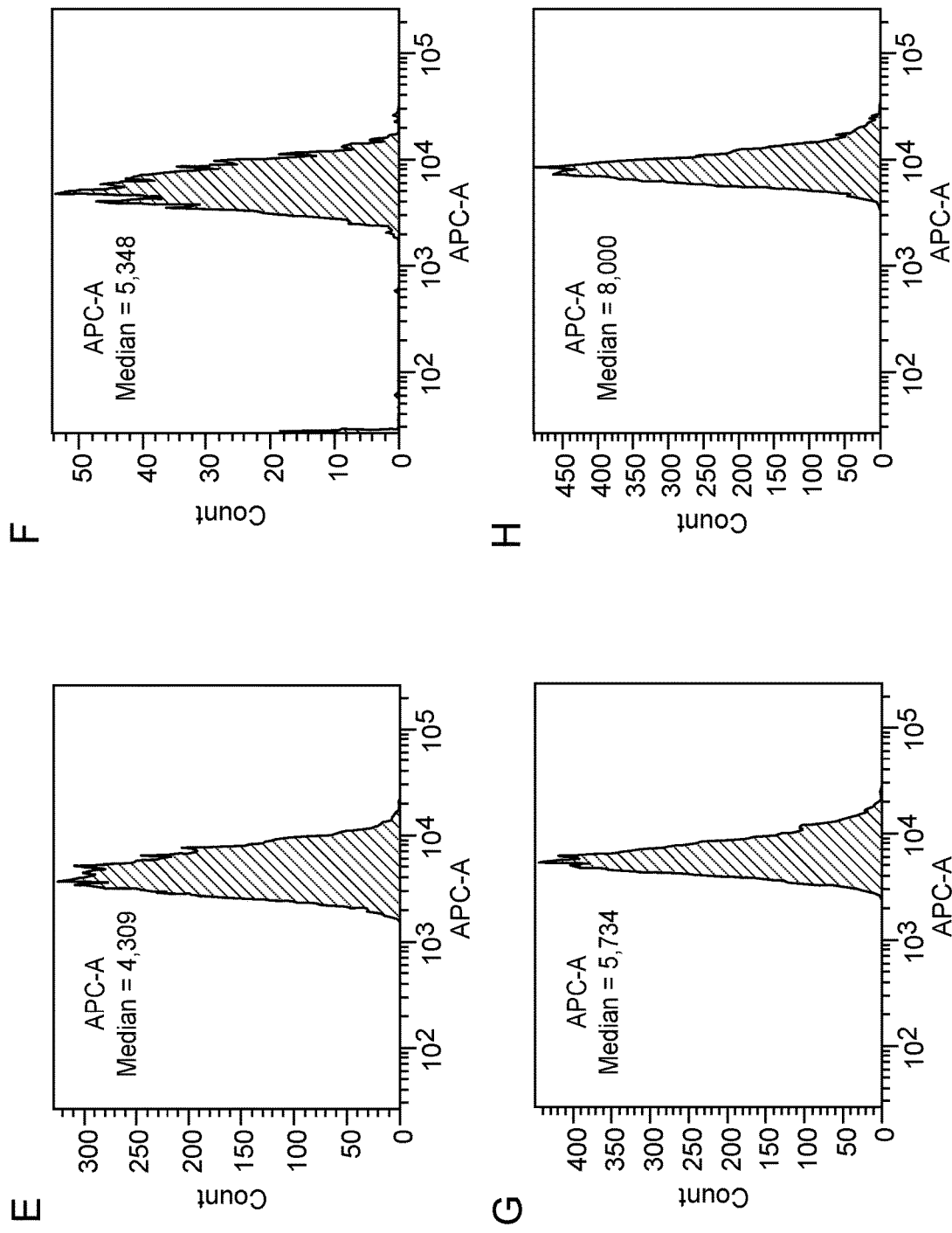
Figure 14B:
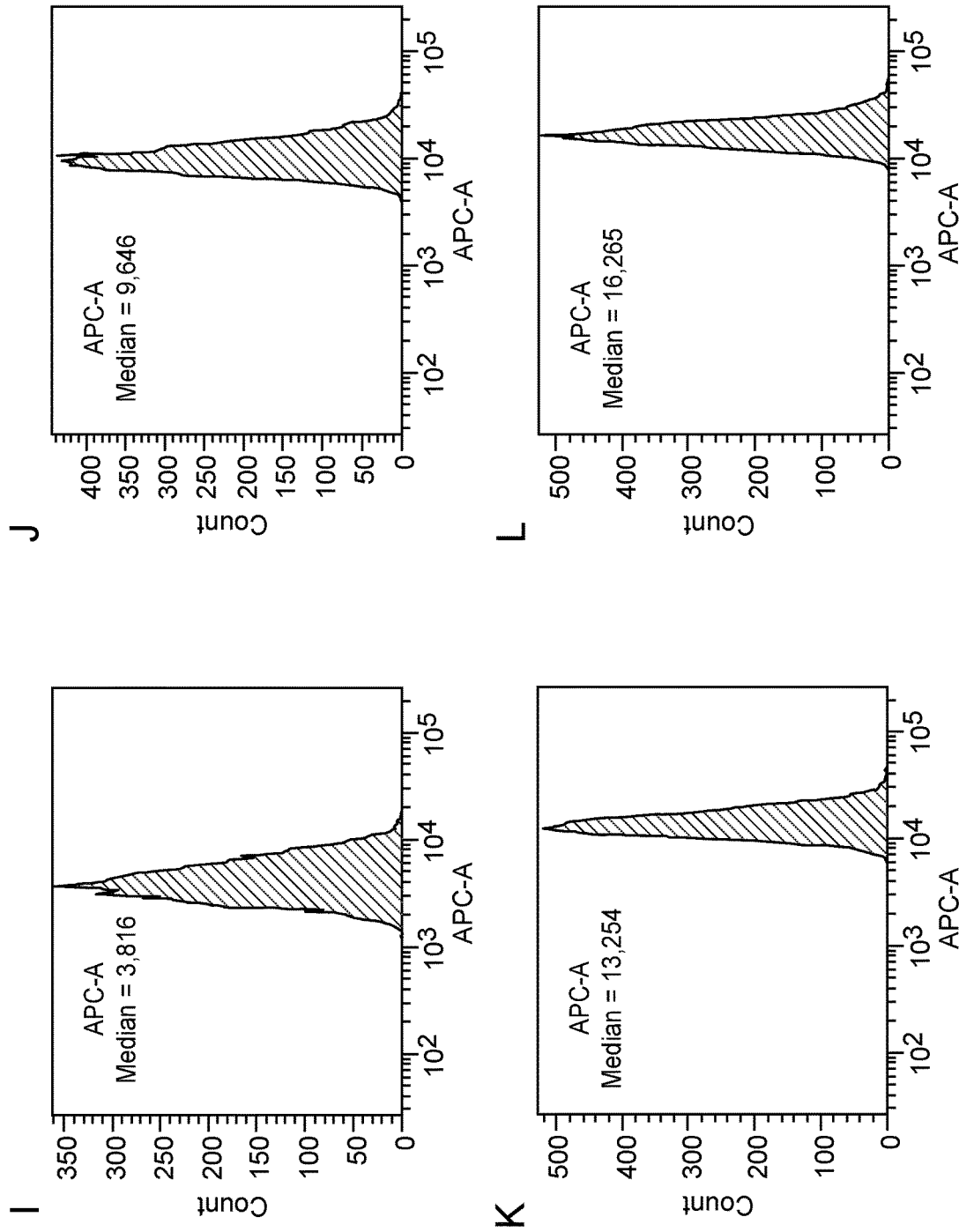
Figure 15:
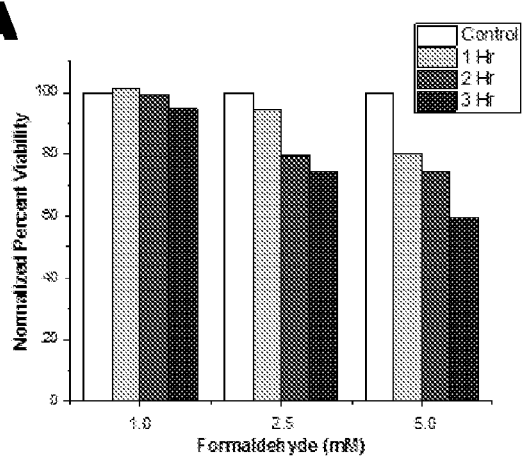
FIG. 15 depicts a Trypan blue dye exclusion assay to determine cell viability of FIG. 15A, HEK293TN cells and FIG. 15B, NS-1 cells treated with FA. Both cell lines were treated 1 mM, 2.5 mM and 5 mM FA for 1, 2 and 3 hrs. For each condition, a 10 µL sample of cells was mixed with 10 µL of a 2× trypan blue solution. Live and dead cells were counted at each of the four 4×4 quadrants of a hemocytometer using a light microscope equipped with a 10× objective. Control samples treated with a vehicle control were normalized to 100% viability.
Figure 15:
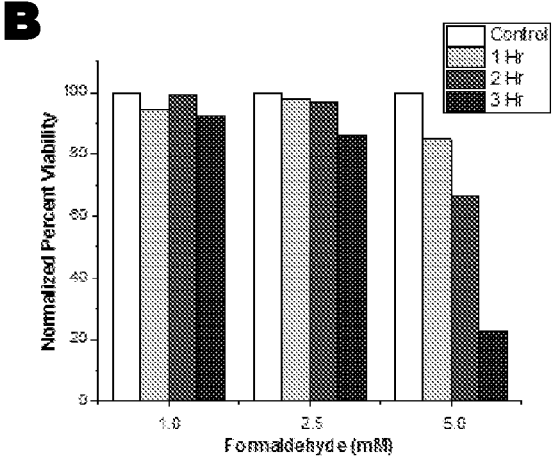
Figure 16:
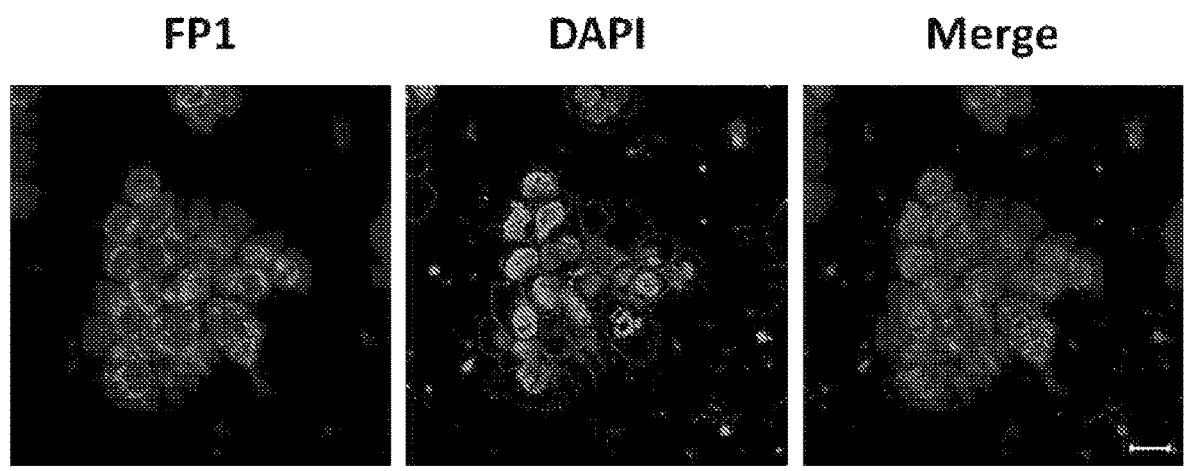
FIG. 16 depicts nuclear staining of HEK293TN cells with DAPI and demonstrates cell viability by showing intact nuclei after FP1 stained cells were treated with 5 mM FA for 3 hrs. DAPI was applied as a 300 nM solution in serum-free DMEM for 5 min. Left: Fluorescent signal from FP1 obtained by irradiation with the 633 nm HeNe laser. Middle: Fluorescent signal from DAPI obtained by irradiation with the 405 nm laser line. Right: Merged image of both signals. Scale bar represents 20 µm.

After demonstrating excellent responsiveness to FA and exceptional selectivity in vitro, the ability of FP1 to visualize FA in live cells was tested. To this end, HEK293TN cells were incubated with 2 μM FP1 at 37° C. for 8 min and then treated with buffer alone or buffer containing FA at 1, 2.5, or 5 mM for 3 hrs. Prior to imaging, cells were allowed to recover in FA-free buffer for 30 min. As shown in FIG. 8A FIG. 8D and quantified in FIG. 8E, treatment of HEK293TN cells with FA resulted in a dose-dependent increase in fluorescence. At 5 mM FA, a nearly 3-fold fluorescence increase was recorded. Likewise, a time-dependent turn-on response at each FA concentration was observed (FIG. 9 and FIG. 10). Having established the utility of FP1 in live HEK293TN cells, Neuroscreen-1 (NS1) cells, a subclone of the PC12 cell-line which is recognized as a standard neuronal model system, was examined (Greene and Tischler, *Proc. Natl. Acad. Sci. U.S.A.* 1976, 73:2424). As was the case with HEK293TN cells, incubation of NS1 cells with 1, 2.5, or 5 mM FA at 37° C. for 3 hrs gave rise to a robust dose-dependent signal enhancement of up to 2.3-fold (FIG. 11A to FIG. 11D), as well as a time-dependent turn-on response at each concentration (FIG. 12 and FIG. 13). The fluorescence increase was confirmed via HR-MS to have resulted from conversion of FP1 to carboxyaldehyde 4 by reacting FP1 with 5 mM FA in the presence of cellular lysates (FIG. 14B). Because FA is a powerful fixative, cell viability assays were performed to determine the cytotoxicity of FA under experimental conditions. A dye exclusion protocol was employed, utilizing trypan blue to selectively stain and distinguish dead cells from those that were viable. At 1 mM FA, only 5% of the HEK293TN cells were dead after 3 hrs, whereas nearly 35% of cells were no longer viable at 5 mM FA (FIG. 15A). NS1 cells on the other hand, were remarkably resilient when incubated with FA up to 2.5 mM. Specifically, at this concentration there was only ca. 12% loss in viability after 3 hrs. Incubation with 5 mM FA resulted in considerable cell death (FIG. 15B). To further verify that the cell populations under investigation were indeed alive, DAPI, a cell permeable nuclear and chromosome counterstain, was employed to identify intact nuclei (FIG. 16).

Figure 17A:
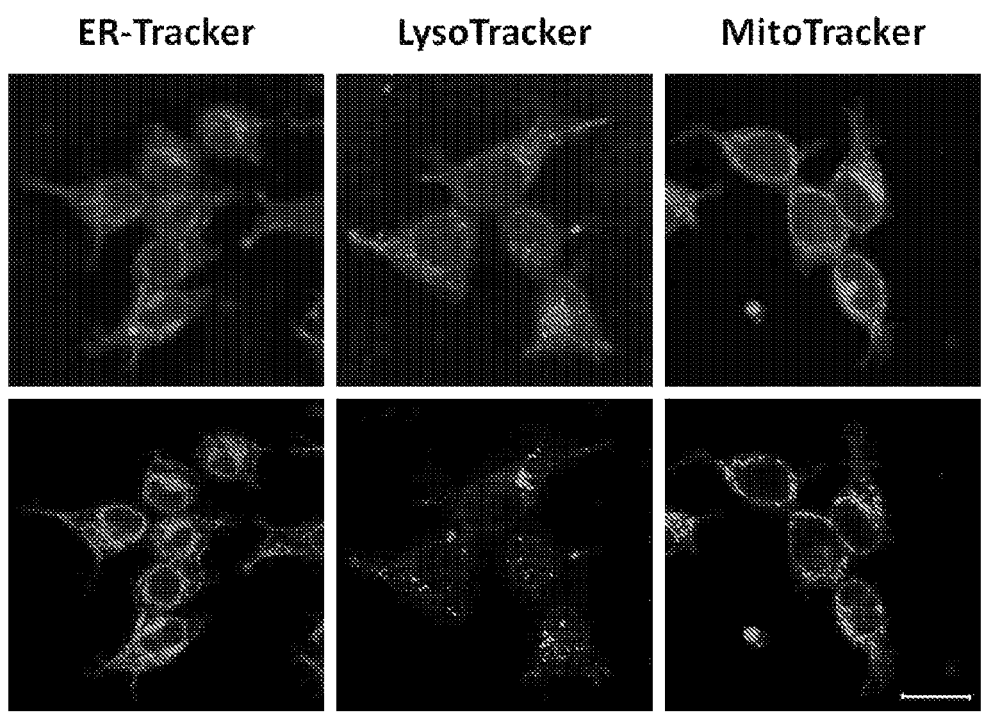
FIG. 17A-17B depict confocal microscopy images.
Figure 17B:
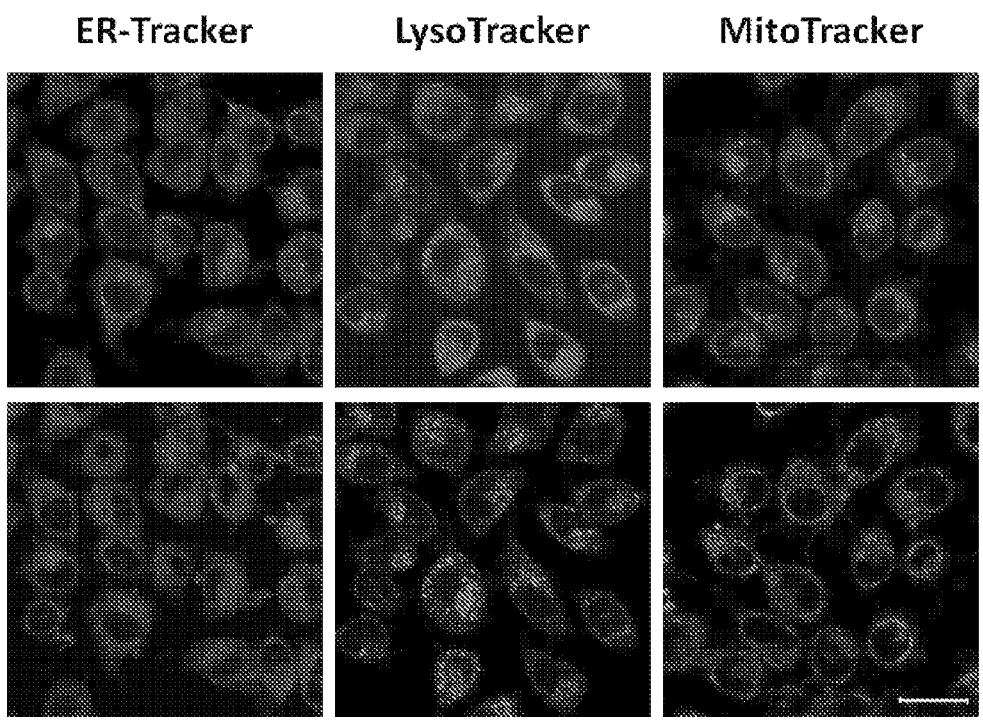
Figure 18:
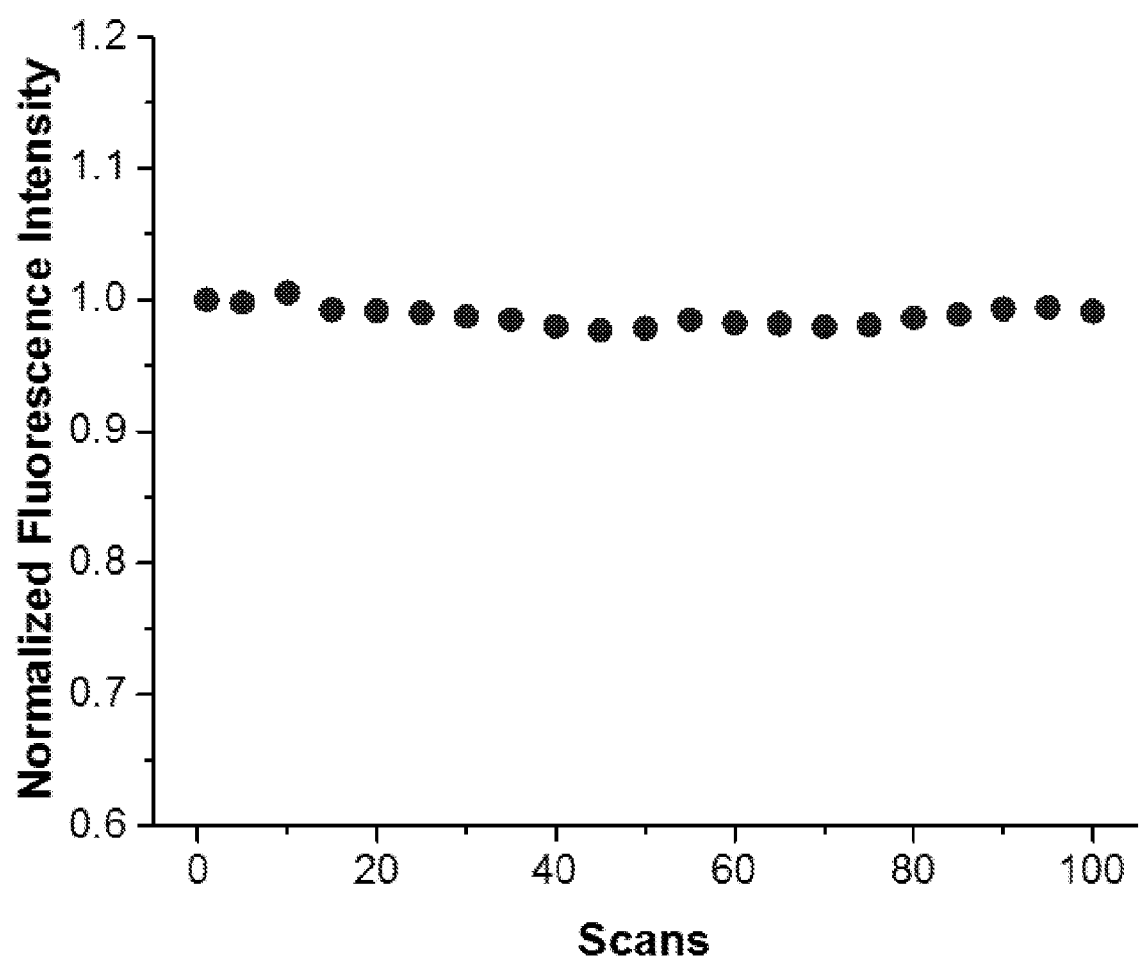
FIG. 18 depicts a photobleaching assay of FP1 in live cells. HEK293TN cells were stained with a solution of 2 µM FP1 in DMEM for 8 min, rinsed with fresh DMEM. After 30 min, a field of cells was subjected to irradiation for 100 scans with the 633 nm HeNe laser set at 25% power with a pinhole size of 1 airy unit. A data point is plotted for every 5 scans.

It was essential to determine the staining pattern of FP1 because enzymes that produce endogenous FA exhibit unique subcellular localization patterns. For example, semi-carbazide-sensitive amine oxidase (SSAO) is primarily localized to the plasma membrane (Andres et al., *J. Histochem. Cytochem.* 2001, 49:209). Thus, both HEK293TN and NS1 cells were costained with ER-Tracker Green, LysoTracker Green DND-26, and MitoTracker Green FM, fluorescent indicators that are known to selectively stain the endoplasmic reticulum, lysosome, and mitochondria, respectively in almost all cell types (FIG. 17A and FIG. 17B). From these imaging experiments, it was evident that FP1 stained the cytoplasm, as well as the endoplasmic reticulum in both cell lines as judged by excellent fluorescence overlay with ER-Tracker Green. In contrast, FP1 did not co-localize with the lysosomal or mitochondrial stains. Additionally, an assay was performed to determine dye efflux properties. HEK293TN and NS1 cells were stained with 1 µM FP1 for 8 min and then washed with fresh dye-free buffer. Images were acquired after a 30 min recovery period and then again after 8 hrs. It was found that there was no statistically significant decrease in fluorescence suggesting that FP1 is chemically stable and does not efflux into the cell media. The photostability of FP1 toward repeated irradiation cycles was examined There was no decrease in fluorescence after 100 scans at 25% laser power with a pinhole size of 1 airy unit (FIG. 18). Of note, 3% laser power is routinely used for all other imaging experiments described in this example. Owing to the exquisite photostability of FP1, a time-lapse imaging experiment in live NS1 cells was performed. For this experiment, NS1 cells were stained with 1 µM FP1 as previously described followed by on-stage addition of 1 mM FA at 25° C. Images were then acquired every min for 2 hrs. Under these conditions a 1.3-fold fluorescence increase was observed; it is also noted that a FA-induced cell rounding effect which could be reversed during a 30 min recovery period was observed.

Figure 19:
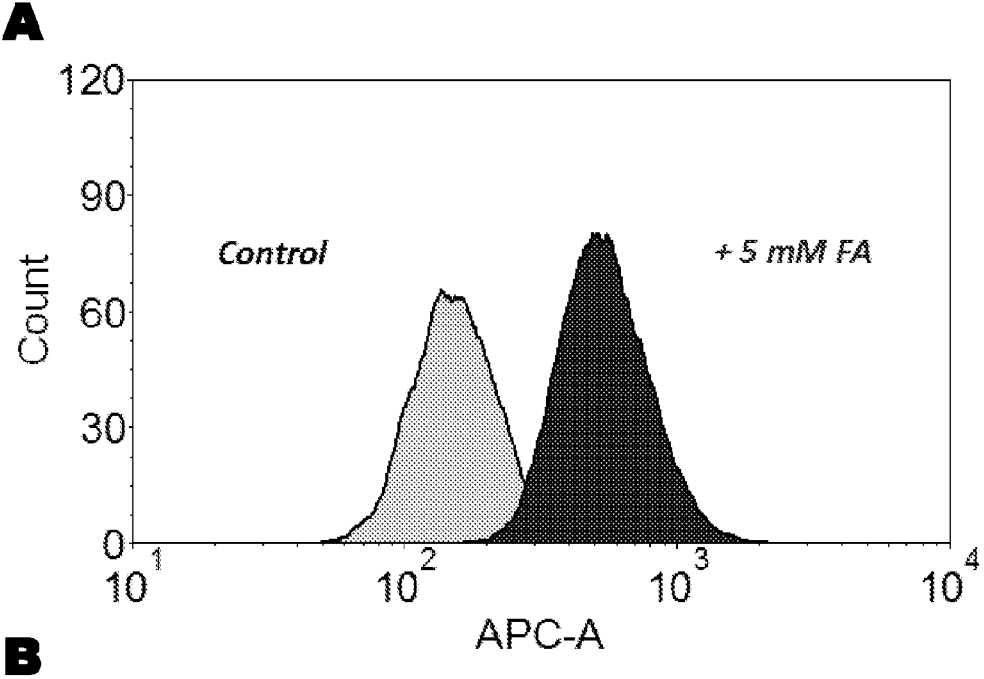
FIG. 19 depicts flow cytometry analysis of FIG. 19A, HEK293TN and FIG. 19B, NS1 cells stained with 1 µM FP1 and incubated with 5 mM FA at 37° C. for 3 hrs. Excitation was provided by the 633 nm HeNe laser and an APC-A filter set was applied. Only live cells were counted.
Figure 19:
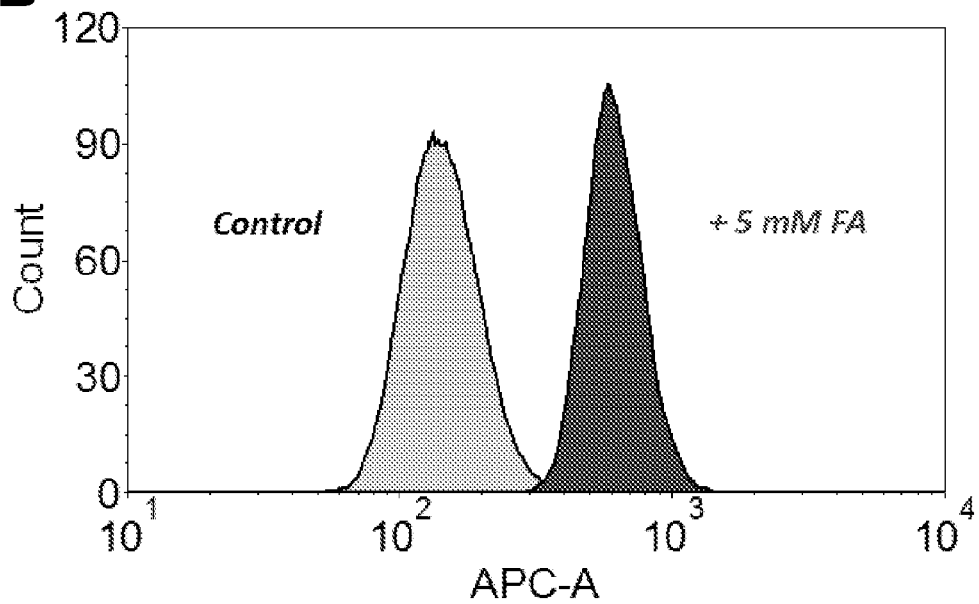

To support confocal imaging data, flow cytometry was used because this high-throughput technique allows for the rapid quantification of large cell populations. As such, HEK293TN and NS1 cells were stained with FP1 as previously described and then incubated with 1, 2.5, and 5 mM FA for up to 3 hrs. As with confocal imaging, a concentration- and time-dependent fluorescence signal enhancement was observed (FIG. 14A and FIG. 14B). There was a clear and unambiguous shift in the live cell population when FA was applied. Based on the median APC-A fluorescence intensity values (an APC-A filter set was used), treatment of HEK293TN cells with 5 mM FA at 37° C. for 3 hrs resulted in nearly a 2.5-fold turn-on, which is in agreement with the confocal imaging assays of 2.9-fold (FIG. 19A). In contrast, NS1 cells incubated with 5 mM FA afforded a 4.2-fold increase by flow cytometry, whereas, only a 2.3-fold turn-on was noted using confocal microscopy (FIG. 19B). This discrepancy can be attributed to the cytotoxicity of FA at this concentration which reduces the fluorescence of dead cells due to dye leakage. Thus, a lower apparent turn-on was recorded because it is difficult to image only viable cells in the presence of those that are dead.

Figure 20:
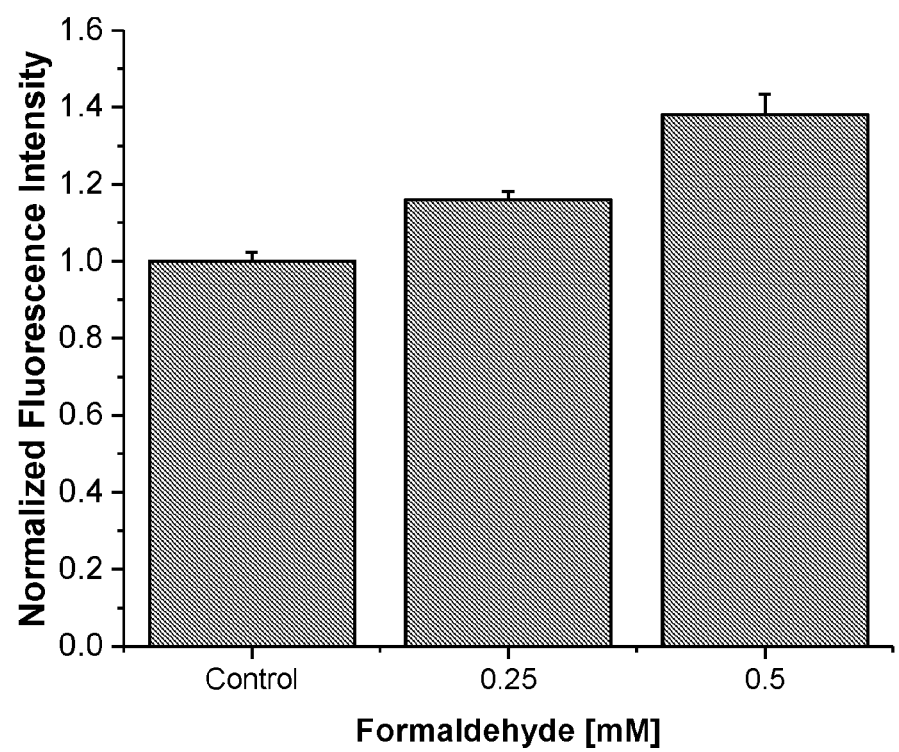
FIG. 20 depicts quantification of data obtained from confocal microscopy images acquired by irradiation of NS1 cells treated with a vehicle control, 0.25 mM and 0.5 mM FA at 37° C. for 3 hrs with the 633 nm HeNe laser. Cells incubated with 0.25 mM FA resulted in a 16% fluorescence increase, whereas, cells incubated with 0.5 mM FA gave rise to a 38% signal enhancement. For each condition, a minimum of 5 images were averaged (n>5). Errors represent standard deviation.
Figure 21:
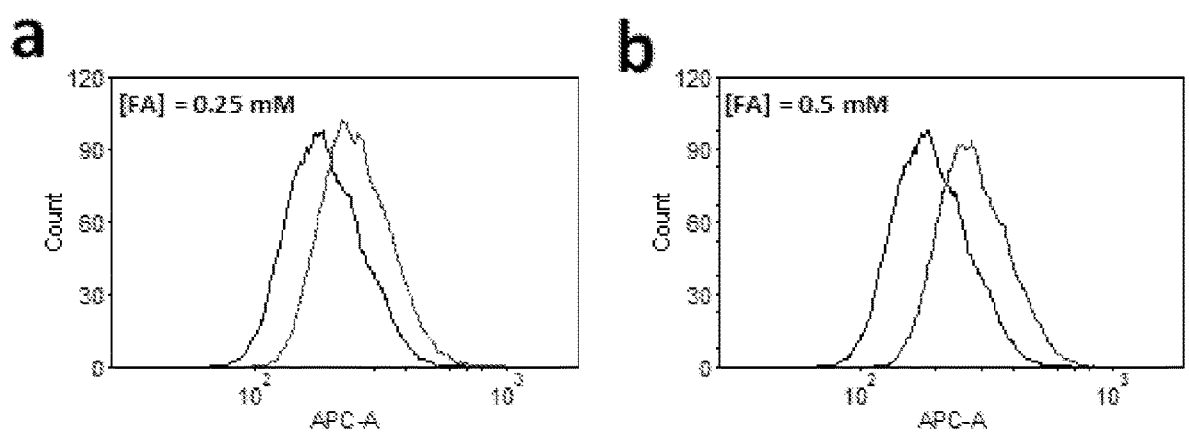
FIG. 21 depicts flow cytometry analysis of NS1 cells stained with 1 µM FP1 and incubated with a) 0.25 mM and b) 0.5 mM FA at 37° C. for 3 hrs. Excitation was provided by the 633 nm HeNe laser and an APC-A filter set was applied. Only live cells were counted.

To demonstrate that FP1 possessed sufficient sensitivity to detect physiologically relevant levels of FA, confocal imaging and flow cytometry assays were repeated by treating living NS1 cells stained with FP1 with 0.25 and 0.5 mM FA. As with higher concentrations of FA, incubation of NS1 cells with 0.25 and 0.5 mM FA at 37° C. for 3 hrs afforded a dose-dependent signal enhancement of 16% and 38%, respectively (FIG. 20). Likewise, flow cytometry analyses of NS1 cells incubated with 0.25 and 0.5 mM resulted in a 42% and 50% fluorescence turn-on, respectively (FIG. 21).

The following materials and methods were used in the Example described below.

General Materials and Methods

Figure 22:
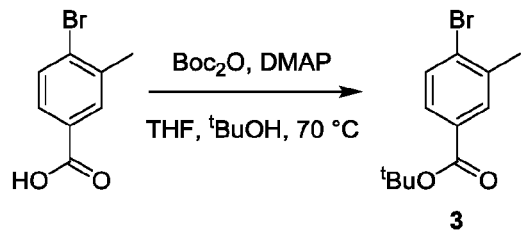
FIG. 22 depicts schematics of the steps involved in synthesizing FAP-1.
Figure 22:
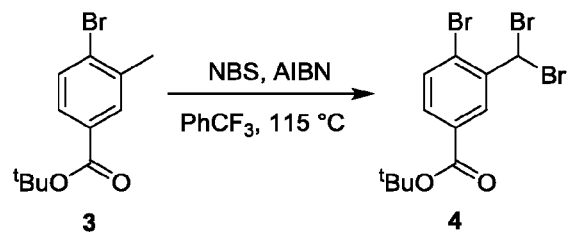
Figure 22:
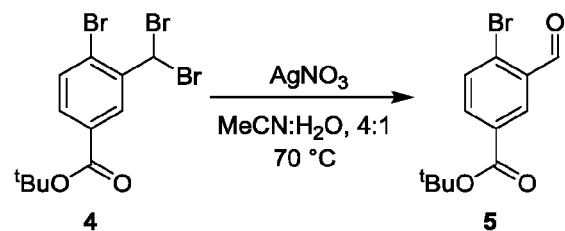
Figure 22:
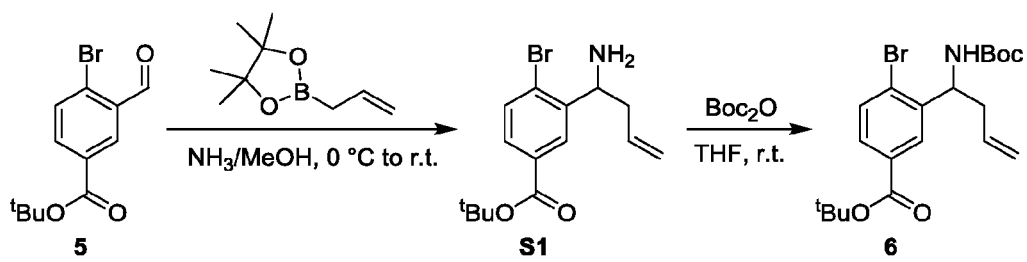
Figure 22:
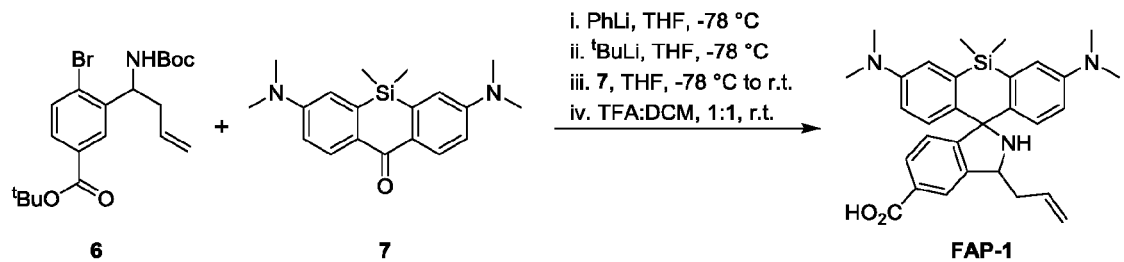

FIG. 22 shows the steps involved in synthesizing FAP-1. All reactions utilizing air- or moisture-sensitive reagents were performed in dried glassware under an atmosphere of dry $N_2$. When dry solvent was used the solvent was passed over activated alumina. Other reagents were used without further purification. Silica gel P60 (SiliCycle) was used for column chromatography and SiliCycle 60 F254 silica gel (precoated sheets, 0.25 mm thick) was used for analytical thin layer chromatography and visualized by fluorescence quenching under UV light. 3,7-Bis(N,N-dimethylamino)-5,5-dimethyldibenzo[b,e]silin-10(5H)-one (compound 7) was synthesized according to literature procedures (Pastierik et al., *J. Org. Chem.* 2014, 79:3374-3382). 4-bromo-3-methylbenzoic acid was purchased from AK Scientific (Union City, Calif.); 4-hydroxynonenal solution was purchased from Cayman Chemical (Ann Arbor, Mich.); glucosone and tranylcypromine were purchased from Santa Cruz Biotech (Dallas, Tex.); and all other reagents were purchased from Sigma-Aldrich (St. Louis, Mo.). $^1$H NMR and $^{13}$C NMR spectra were collected in $CDCl_3$ or $CD_3OD$ (Cambridge Isotope Laboratories, Cambridge, Mass.) at 25° C. on Bruker AVB-400 and AV-600 with $^{13}$C operating frequencies of 101 MHz and 150 MHz, respectively, at the College of Chemistry NMR Facility at the University of California, Berkeley. All chemical shifts are reported in the standard δ notation of parts per million relative to residual solvent peak at 7.26 ($CDCl_3$) or 3.31 ($CD_3OD$) for $^1$H and 77.16 ($CDCl_3$) or 49.00 ($CD_3OD$) for $^{13}$C as an internal reference. Splitting patterns are indicated as follows: br, broad; s, singlet; d, doublet; t, triplet; m, multiplet; dd, doublet of doublets. Low-resolution electrospray mass spectral analyses were carried out using a LC-MS (Agilent Technology 6130, Quadrupole LC/MS). High resolution mass spectral analyses (ESI-MS) and low-resolution electron-impact mass spectral analyses were carried out at the College of Chemistry Mass Spectrometry Facility at the University of California, Berkeley.

Probe Synthesis and New Compound Characterization tert-Butyl 4-bromo-3-methylbenzoate tert-Butyl 4-bromo-3-methylbenzoate (FIG. 22, compound 3) was synthesized as follows. To a stirred suspension of 4-bromo-3-methylbenzoic acid (20 g, 93 mmol) and DMAP (17 g, 140 mmol) in 200 mL of $^t$BuOH:THF, 1:1, was carefully added Boc$_2$O (40.6 g, 186 mmol) with evolution of gas. Once gas evolution had ceased, the reaction mixture was warmed to 70° C. TLC (5% EtOAc/hexanes) showed complete consumption of starting material after 12 h. The solvent was removed under reduced pressure. To remove residual Boc$_2$O (Basel and Hassner, *Synthesis.* 2001, 2001:0550-0552), the crude reaction mixture was re-dissolved in 150 mL EtOH, imidazole (15 g, 220 mmol) was added, and the solution was stirred at ambient temperature for 3 h. EtOH was removed under reduced pressure, and the residual solid was re-suspended in 200 mL EtOAc and washed sequentially with 10% aq $K_2CO_3$ (1×200 mL), $H_2O$ (1×200 mL), 1 M HCl (2×200 mL), and brine (1×200 mL). The organic layer was dried over anhydrous $MgSO_4$ and concentrated under reduced pressure. Purification by silica column chromatography (4% EtOAc/hexanes) afforded compound 3 as a colorless liquid (17.7 g, 70% yield). $^1$H NMR (400 MHz, $CDCl_3$) δ 7.82 (d, J=2.0 Hz, 1H), 7.63 (dd, J=8.3, 2.1 Hz, 1H), 7.55 (d, J=8.3 Hz, 1H), 2.42 (s, 3H), 1.58 (s, 9H); $^{13}$C NMR (151 MHz, $CDCl_3$) δ 165.2, 137.9, 132.2, 131.5, 131.1, 129.8, 128.1, 81.3, 28.1, 22.8; LRMS calcd. for $C_{12}H_{15}BrO_2$ (M+) 270.03. found 270.

tert-Butyl 4-bromo-3-(dibromomethyl)benzoate tert-Butyl 4-bromo-3-(dibromomethyl)benzoate (FIG. 22, compound 4) was synthesized as follows. To a stirred solution of compound 3 (7.7 g, 28.4 mmol) in 200 mL PhCF$_3$ in a 2-neck round-bottom flask fitted with a reflux condenser were added portions of NBS (5.05 g, 28.4 mmol) and AIBN (0.07 g, 0.42 mmol) at ambient temperature followed by heating at 115° C. for 2 hours for a total of three iterations. AIBN (0.07 g, 0.42 mmol) was added a final time, and the reaction mixture was heated at 115° C. for 2 hours, then cooled to ambient temperature. The reaction mixture was filtered through a sintered funnel, and the residual solid was washed with DCM (ca. 100 mL). The combined filtrate was washed sequentially with 1 M aq. NaOH (2×200 mL), H$_2$O (1×200 mL), and brine (1×200 mL). The organic layer was dried over anhydrous MgSO$_4$, and the solvent was removed under reduced pressure to afford compound 4 as a pale yellow liquid that crystallized on standing (11.7 g, 96% yield). $^1$H NMR (400 MHz, CDCl$_3$) δ 8.58 (d, J=2.1 Hz, 1H), 7.72 (dd, J=8.4, 2.1 Hz, 1H), 7.51 (d, J=8.3 Hz, 1H), 7.03 (s, 1H), 1.59 (s, 9H); $^{13}$C NMR (101 MHz, CDCl$_3$) δ 164.0, 140.5, 132.7, 132.6, 132.0, 131.6, 124.3, 82.1, 39.1, 28.2. LRMS calcd. for $C_{12}H_{13}Br_3O_2$ (M+) 425.85. found 426.

tert-Butyl 4-bromo-3-formylbenzoate tert-Butyl 4-bromo-3-formylbenzoate (FIG. 22, compound 5) was synthesized as follows. To a stirred solution of compound 4 (5.5 g, 12.8 mmol) in 150 mL MeCN was added a solution of AgNO$_3$ (5.45 g, 32 mmol) in 35 mL H$_2$O. The reaction mixture was heated to 70° C. for 24 h, whereupon TLC (5% EtOAc in hexanes) indicated complete consumption of starting material. The reaction mixture was cooled to 0° C., filtered through celite, and concentrated under reduced pressure. The resulting residue was diluted with H$_2$O (50 mL) and extracted with EtOAc (2×100 mL). The combined organic layers were washed with H$_2$O (2×150 mL) and brine (1×200 mL), then dried over anhydrous MgSO$_4$. The solvent was removed under reduced pressure, and purification by silica column chromatography (3% EtOAc/hexanes) afforded compound 5 as a colorless liquid that crystallized on standing (1.32 g, 36% yield). $^1$H NMR (400 MHz, CDCl$_3$) δ 10.28 (s, 1H), 8.36 (d, J=2.2 Hz, 1H), 7.96 (dd, J=8.3, 2.2 Hz, 1H), 7.63 (d, J=8.3 Hz, 1H), 1.53 (s, 9H); $^{13}$C NMR (101 MHz, CDCl$_3$) δ 190.8, 163.86, 135.4, 134.0, 133.3, 132.1, 131.0, 130.7, 82.2, 28.1. LRMS calcd. for $C_{12}H_{13}BrO_3$ (M+) 284.00, found 284.

tert-Butyl 4-bromo-3-(1-((tert-butoxycarbonyl)amino)but-3-en-1-yl)benzoate tert-Butyl 4-bromo-3-(1-((tert-butoxycarbonyl)amino)but-3-en-1-yl)benzoate (FIG. 22, compound 6) was synthesized as follows. To a solution of compound 5 (1.2 g, 4.2 mmol) in 40 mL MeOH at 0° C. was added 6 mL of NH$_3$ solution (7 N in MeOH, 42 mmol). The reaction mixture was stirred at 0° C. for 30 min, then allylboronic acid pinacol ester (0.95 mL, 5 mmol) was added, and the reaction mixture was warmed to ambient temperature and stirred for 10 h. The solvent was removed under reduced pressure, and purification by silica column chromatography (0→5% MeOH/DCM) afforded 0.98 g of a mixture of compound S1 and pinacol as a colorless liquid which was used directly without further purification. $^1$H NMR (asterisks denote pinacol peaks, 400 MHz, CDCl$_3$) δ 8.09 (d, J=2.1 Hz, 1H), 7.67 (dd, J=8.3, 2.2 Hz, 1H), 7.56 (d, 1H, J=8.3 Hz), 5.85-5.73 (m, 1H), 5.20-5.07 (m, 2H), 4.41 (dd, J=8.4, 4.5 Hz, 1H), 2.54 (m, 1H), 2.36-2.22 (m, 1H), 1.58 (s, 9H), 1.22* (s, 19H). $^{13}$C NMR (asterisks denote pinacol peaks, 101 MHz, CDCl$_3$) δ 165.3, 144.8, 134.9, 132.9, 131.7, 129.1, 128.4, 128.2, 118.3, 81.6, 75.1*, 53.7, 42.1, 28.3, 25.0*. LRMS calcd. for $C_{15}H_{21}BrNO_2$(M+H) 326.08, found 326.0.

To a solution of crude amine compound S1 in 100 mL THF was added Boc$_2$O (0.50 g, 2.2 mmol, 1.2 eq as determined by $^1$H NMR of crude compound S1) and the reaction was stirred for 14 h, whereupon TLC (10% EtOAc/hexanes) indicated complete consumption of compound Si. The solvent was removed under reduced pressure, and purification by silica column chromatography (5% EtOAc/hexanes) afforded compound 6 as a colorless oil which crystallized on standing (630 mg, 35% yield over 2 steps). $^1$H NMR (3:1 rotamer ratio, asterisks denote minor rotamer peaks, 400 MHz, CDCl$_3$) δ 7.89 (s, 1H), 7.64 (dd, T=8.3, 2.1 Hz, 1H), 7.51 (d, T=8.3 Hz, 1H), 5.78-5.57 (m, 1H), 5.45* (br. s., 1H), 5.33-5.16 (m, 1H), 5.17-4.99 (m, 2H), 2.62-2.40 (m, 1H), 2.40-2.25 (m, 1H), 1.52 (s, 9H), 1.35 (s, 9H), 1.21* (br. s., 9H). $^{13}$C NMR (101 MHz, CDCl$_3$) δ 165.0, 155.0, 142.0, 133.4, 133.0, 131.4, 129.1, 128.0, 127.5, 118.7, 81.4, 79.5, 53.3, 39.5, 28.3, 28.1. LRMS calcd. for $C_{20}H_{27}BrNO_4$ (M−H) 424.11, found 424.0.

Formaldehyde Probe-1 (FAP-1)

Formaldehyde Probe-1 (FAP-1) (FIG. 22) was synthesized as follows. To a flame-dried 2-neck round-bottomed flask was added compound 6 (0.315 g, 0.74 mmol) and 10 mL of anhydrous THF. The resultant solution was cooled to −78° C. and a solution of PhLi (1.9 M in dibutyl ether, 0.39 mL, 0.74 mmol) was added dropwise. After 1 hour of reaction at −78° C., a solution of t-BuLi (1.7 M in pentane, 0.87 mL, 1.5 mmol) was added dropwise to the reaction mixture. After 10 min at −78° C., a solution of compound 7 (0.048 g, 0.15 mmol) in anhydrous THF (7 mL) was added dropwise, and the reaction mixture was allowed to warm to ambient temperature and stirred for 3 h, during which time the solution changed from pale yellow to dark red in color. The reaction was quenched with 1 M HCl (5 mL), causing a change to dark blue in color. The crude reaction mixture was diluted with saturated aq. NaHCO$_3$ (100 mL) and extracted with EtOAc (4×50 mL). The combined organic layers were washed with brine (200 mL) and dried over anhydrous MgSO$_4$. The solvent was removed under reduced pressure, and the crude material was dissolved in TFA:DCM, 1:1 (50 mL) and stirred at ambient temperature for 12 hours. The solvent was removed under reduced pressure, and purification by preparative reverse-phase HPLC (linear gradient from 30% MeCN/70% H$_2$O/0.05% formic acid to 100% MeCN/0.05% formic acid over 60 minutes) afforded FAP-1 as a pale blue powder (25.0 mg, 34% yield). $^1$H NMR (400 MHz, CD$_3$OD) δ 8.16 (s, 1H), 8.04 (d, 1H, J=8.1 Hz), 7.07 (dd, J=9.4, 2.9 Hz, 2H), 6.96 (d, J=7.9 Hz, 1H), 6.80 (d, J=9.0 Hz, 1H), 6.74 (dd, J=9.0, 2.8 Hz, 1H), 6.63 (dd, J=9.0, 2.9 Hz, 1H), 6.44 (d, T=9.0 Hz, 1H), 5.97-5.82 (m, 1H), 5.32-5.18 (m, 2H), 2.98 (d, T=15.1 Hz, 12H), 2.93-2.73 (m, 2H), 2.65 (s, 1H), 0.64 (s, 3H), 0.54 (s, 3H). $^{13}$C NMR (101 MHz, CD$_3$OD) δ151.3, 151.2, 149.0, 140.7, 138.8, 138.1, 133.5, 133.0, 132.6, 132.1, 132.0, 131.0, 126.5, 125.0, 120.5, 118.2, 117.4, 115.1, 115.1, 80.0, 62.9, 40.4, 40.3, 38.2, 0.6, −1.9. Note: carboxylic acid carbon not observed. HRMS calcd. for $C_{30}H_{36}O_2N_3Si$ (M+H) 498.2571. found 498.2563.

Spectroscopic Materials and Methods

Milli-Q water was used to prepare all aqueous solutions. All spectroscopic measurements were performed in 20 mM PBS, pH 7.4. Absorption spectra were recorded using a Varian Cary 50 spectrophotometer, and fluorescence spectra were recorded using a Photon Technology International Quanta Master 4 L-format scan spectrofluorometer equipped with an LPS-220B 75-W xenon lamp and power supply, A-1010B lamp housing with integrated igniter, switchable 814 photocounting/analog photomultiplier detection unit, and MD5020 motor driver. Samples for absorption and emission measurements were contained in 1-cm×1-cm quartz cuvettes (1.4-mL volume, Starna).

Quantum Yield

Quantum yield was determined using zinc phthalocyanine (ZnPc) as a standard according to a published method (Williams et al., Analyst. 1983, 108:1067-1071). For FAP-1 and ZnPc, the absorbance spectra were measured within an absorbance range below 0.1. The quantum yield was calculated according to the equation: $\phi_{sample} = \phi_{standard}(\text{Grad}_{sample}/\text{Grad}_{standard})(\eta_{sample}^2/\eta_{standard}^2)$; where $\phi$ is the quantum yield, $\phi_{standard} = 0.34$ in 1% pyridine/toluene (Bishop et al., *J. Photochem. Photobiol.* 1995, 90:39-44), Grad is the slope of the plot of absorbance versus integrated emission intensity, and $\eta$ is the refractive index of the solvent.

Measurement of Partition Coefficient

A modified version of the shake method was used to determine the partition coefficient or log $D_{oct/wat}$ value for FAP-1 (Rothbard et al., *J. Am. Chem. Soc.* 2004, 126:9506-9507). Briefly, 1-octanol-saturated PBS (248 μL), PBS-saturated 1-octanol (248 μL), and 1 mM solution of FAP-1 in DMSO (5 μL) were added to a 0.6-mL microcentrifuge tube. The dye was partitioned between the layers via vortexing for 30 s. The microcentrifuge tube was centrifuged on a bench-top minifuge at 4 k rpm for 4 minutes to separate the layers. A portion of the 1-octanol layer (200 μL) was transferred to a 96-well plate, and the fluorescence emission from 665-700 nm was measured (excitation at 645 nm) using a Synergy Mx multimode microplate reader (BioTek Instruments, Inc.) equipped with fluorescence module. The concentration of dye in the 1-octanol layer was determined by comparison with a standard curve constructed from six data points. Measurements were performed in triplicate to give log $D_{oct/wat} = 0.53 \pm 0.01$ (mean±standard deviation).

FAP-1 Fluorescence Response to FA

Figure 24A:
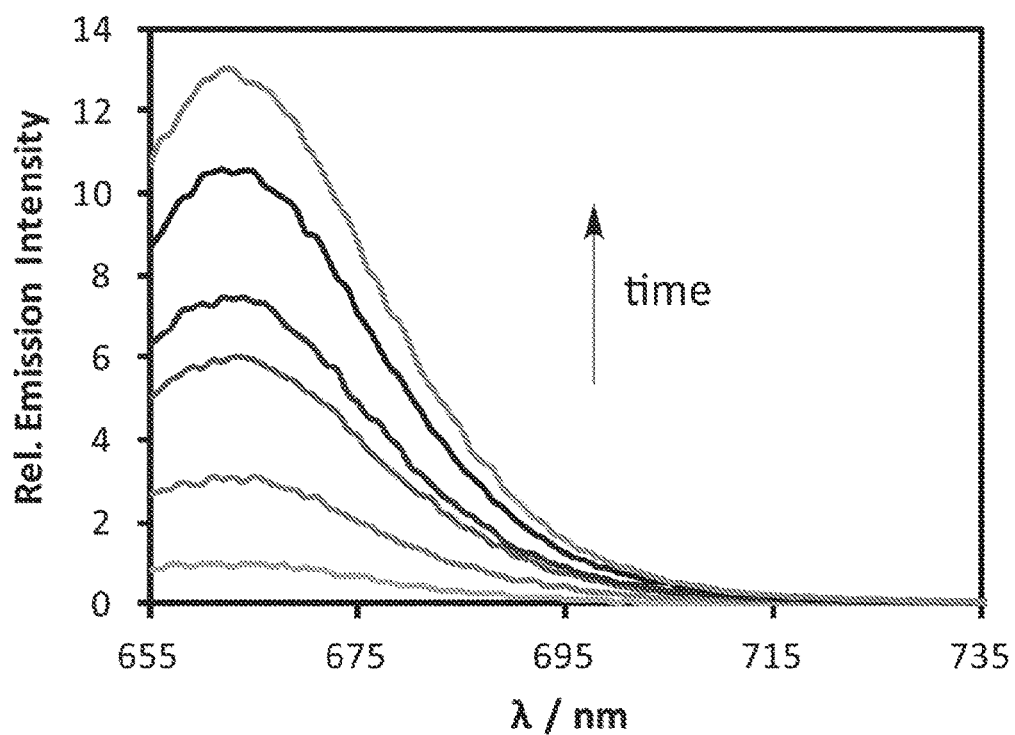
FIG. 24A-24B depict fluorescence responses.

999 μL of a 10.01 μM solution of FAP-1 in 20 mM PBS (pH 7.4) was prepared by diluting a 10 mM dimethylsulfoxide (DMSO) stock solution of FAP-1 into pre-warmed PBS (37° C.) in a 1-cm×1-cm quartz cuvette. 1 μL of 100 mM stock solution of FA (freshly prepared by diluting commercial 37 wt. % in H$_2$O FA solution) was added (for a final concentration of 100 μM), and the mixture was mixed by vigorous pipetting for 5 s, followed by acquisition of the t=0 spectrum. Emission spectra ($\lambda_{ex}$=645 nm, $\lambda_{em}$=655-750 nm) were collected at 0, 20, 45, 60, 90, and 120 min (see FIG. 24A). Temperature was maintained at 37° C. throughout the experiment by immersing the cuvette in a heated water bath between measurements.

FAP-1 In Vitro Detection Limit

999 μL of a 10.01 μM solution of FAP-1 in 20 mM PBS (pH 7.4) was prepared by diluting a 10 mM DMSO stock solution of FAP-1 into pre-warmed PBS (37° C.) in a 1-cm×1-cm quartz cuvette. 1 μL of a FA stock solution (either 5 mM or 1 mM, freshly prepared by diluting commercial 37 wt. % FA solution with Milli-Q water) or 1 μL of PBS was added (for a final concentration of 5 μM, 1 μM, or 0 μM FA), and the mixture was mixed by vigorous pipetting for 5 s and placed in a 37° C. water bath. Emission spectra were obtained after 120 min. Statistical analyses for multiple comparisons were performed using one-way ANOVA with the Bonferroni correction in the statistical analysis software, R.

Selectivity Tests

999 μL of a 10.01 μM solution of FAP-1 (for 4-hydroxynonenal cuvette: 998.4 μL of a 10.02 μM solution of FAP-1; for glutathione cuvette: 950 μL of a 10.53 μM solution of FAP-1) in 20 mM PBS (pH 7.4) was prepared by diluting a 10 mM DMSO stock solution of FAP-1 into pre-warmed PBS (37° C.) in a 1-cm×1-cm quartz cuvette. The analyte of interest was added to the cuvette to bring the concentration of analyte to 100 μM (unless otherwise specified) and the concentration of FAP-1 to 10 μM, followed by mixing by vigorous pipetting for 5 seconds, and a t=0 spectrum was acquired. The cuvette was placed in a 37° C. water bath. Emission spectra were recorded by quickly removing the cuvette from the water bath, obtaining the spectrum, and returning the cuvette to the bath. Spectra were taken at t=0, 20, 45, 60, 90, and 120 min (see FIG. 24B).

FA:

1 μL of 100 mM stock solution of FA in Milli-Q water (freshly prepared by diluting 3.76 μL commercial 37 wt. % FA solution to 500 μL with Milli-Q water) was added to 999 μL of a 10.01 μM solution of FAP-1 in PBS.

Acetaldehyde:

1 μL of 100 mM stock solution of acetaldehyde in Milli-Q water (freshly prepared by diluting 2.8 μL neat acetaldehyde to 500 μL with Milli-Q water) was added to 999 μL of a 10.01 μM solution of FAP-1 in PBS.

Glucose:

1 μL of 1 M stock solution of glucose in Milli-Q water (freshly prepared by dissolving 180 mg of glucose in 1 mL Milli-Q water) was added to 999 μL of a 10.01 μM solution of FAP-1 in PBS.

4-Hydroxynonenal (4-HNE):

1.56 μL of 64 mM stock solution of 4-HNE in EtOH (commercial stock) was added to 998.4 μL of a 10.02 μM solution of FAP-1 in PBS.

Dehydroascorbate:

1 μL of 100 mM stock solution of dehydroascorbic acid in Milli-Q water (freshly prepared by dissolving 0.87 mg of dehydroascorbic acid in 50 μL Milli-Q water) was added to 999 μL of a 10.01 μM solution of FAP-1 in PBS.

Glucosone:

1 μL of 100 mM stock solution of glucosone in Milli-Q water (freshly prepared by dissolving 0.9 mg of glucosone in 50 μL Milli-Q water) was added to 999 μL of a 10.01 μM solution of FAP-1 in PBS.

Sodium Pyruvate:

1 μL of 100 mM stock solution of sodium pyruvate in Milli-Q water (freshly prepared by dissolving 11 mg of sodium pyruvate in 1 mL Milli-Q water) was added to 999 μL of a 10.01 μM solution of FAP-1 in PBS.

Oxaloacetate:

1 μL of 100 mM stock solution of oxaloacetate in Milli-Q water (freshly prepared by dissolving 15 mg of oxaloacetic acid in 1.135 mL Milli-Q water) was added to 999 μL of a 10.01 μM solution of FAP-1 in PBS.

H$_2$O$_2$:

1 μL of 100 mM stock solution of H$_2$O$_2$ in Milli-Q water (freshly prepared by diluting 10.2 μL of commercial 9.8 M H$_2$O$_2$ to 1 mL with Milli-Q water) was added to 999 μL of a 10.01 μM solution of FAP-1 in PBS.

Glutathione:

All buffers and stocks were deoxygenated by bubbling a stream of nitrogen gas for 30 minutes. 50 µL of a 100 mM stock solution of glutathione in PBS (freshly prepared by dissolving 615 mg of glutathione in deoxygenated PBS; pH was brought to 7.4 with deoxygenated 1 M NaOH for a final volume of 20 mL) was added to 950 µL of a 10.53 µM solution of FAP-1 in deoxygenated PBS. The screw-top cuvette was capped for the duration of the timecourse.

Methylglyoxal:

1 µL of 100 mM stock solution of methylglyoxal in Milli-Q water (freshly prepared by diluting 7.7 µL of neat methylglyoxal to 500 µL with Milli-Q water) was added to 999 µL of a 10.01 µM solution of FAP-1 in PBS.

Cell Culture Procedures

HEK293T cells were maintained in exponential growth as a monolayer in Dulbecco's Modified Eagle Medium, high glucose, (DMEM, Invitrogen) supplemented with glutamax (Gibco), 10% fetal bovine serum (FBS, Hyclone) and 1% non-essential amino acids (NEAA, Gibco), and incubated at 37° C. in 5% $CO_2$. One day before imaging, the cells were passaged and plated in DMEM with glutamax (phenol red-free) supplemented with 10% FBS on poly-d-lysine-coated 4-well Lab Tek borosilicate chambered coverglass slides (Nunc) at $1.8 \times 10^5$ per well and allowed to grow to 65% confluence before imaging experiments. MCF7 cells were maintained in exponential growth as a monolayer in DMEM, high glucose, supplemented with glutamax and sodium pyruvate (Gibco), 10% FBS, and 1% NEAA. Two days before imaging, the cells were passaged and plated in DMEM with glutamax (phenol red-free) supplemented with 10% FBS on poly-d-lysine-coated 4-well Lab Tek borosilicate chambered coverglass slides at $8 \times 10^4$ per well and allowed to grow to 50% confluence before imaging experiments. Inhibitor treatments were begun after one day of growth.

Confocal Fluorescence Imaging Experiments

Confocal fluorescence imaging studies were performed with a Zeiss laser scanning microscope 710 with a 20× objective lens using Zen 2009 software (Carl Zeiss). FAP-1 was excited using a 633 nm HeNe laser, and emission was collected using a META detector between 638 to 747 nm. Hoechst 33342 was excited with a 405 nm diode laser, and emission was collected using a META detector between 450 and 500 nm. BSS (136.9 mM NaCl, 5.37 mM KCl, 1.26 mM $CaCl_2$, 0.81 mM $MgSO_4$, 0.44 mM $KH_2PO_4$, 0.335 mM $Na_2HPO_4$, 10 mM PIPES; pH to 7.2 with NaOH) was used as the imaging buffer for all confocal experiments. The cells were imaged at 37° C. throughout the course of the experiment. Image analysis and quantification was performed using ImageJ (National Institutes of Health). For quantification of fluorescence intensity, four fields of cells within the same well were imaged. A region of interest (ROI) was created around each cell in each image. The mean fluorescence intensity of each cell was measured (using "Measure" function) and averaged across the four fields imaged. For each condition, multiple wells were analyzed using this process, and the values were averaged across independent experiments for statistical analysis. Statistical analyses for multiple comparisons were performed using one-way ANOVA with the Bonferroni correction in the statistical analysis software, R.

HEK293T Cell Experiments.

The DMEM media was aspirated from the chambers containing cells and replaced with 500 µL BSS containing 10 µM FAP-1 (diluted from 10 mM stock in DMSO) and incubated at 37° C. for 30 minutes. The buffer was then replaced with 500 µL fresh BSS containing no probe, and the cells were imaged to provide the t=0 timepoint. 200 µL of the buffer was removed from each well and mixed with vehicle control (5 µL $H_2O$) or FA (5 µL of 20.2 mM FA for 200 µM final concentration upon re-addition to well, 5 µL 50.5 mM FA for 500 µM final concentration upon re-addition to well, 5 µL 101 mM FA for 1 mM final concentration upon re-addition to well; all FA stocks freshly prepared by diluting 37 wt. % commercial FA). The cells were then incubated at 37° C. for 30 min prior to imaging for the t=30 timepoint. For nuclear staining studies, cells were incubated with 1 µM Hoechst 33342 at 37° C. for 15 min prior to imaging.

MCF7 Cell Experiments.

Vehicle (10 µL Milli-Q water), tranylcypromine (TCP; 0.5 µL of a 20.2 mM stock in Milli-Q water, 20 µM final concentration), or GSK-LSD1 (10 µL of a 51 mM stock in Milli-Q water, 1 µM final concentration) were added to wells containing MCF7 cells in DMEM supplemented with 10% FBS and incubated at 37° C. in 5% $CO_2$ for 20 hours. The DMEM media was removed from the chambers containing cells and replaced with 500 µL BSS containing 10 µM FAP-1 (diluted from 10 mM stock in DMSO) and the same concentration of inhibitor as the 20-hour treatment (no inhibitor, 20 µM TCP, or 1 µM GSK-LSD1) and incubated at 37° C. for 60 minutes, then imaged. For nuclear staining studies, cells were incubated with 1 µM Hoechst 33342 at 37° C. for 15 min prior to imaging.

Colocalization Experiments.

Colocalization experiments were performed in live HEK293T cells. HEK293T cells were labeled with ER-Tracker Green, BODIPY FL $C_5$-Ceramide, LysoTracker Green DND-26, MitoTracker Green FM, and Hoechst 33342 (Life Technologies) according to the manufacturer's instructions. Labeled HEK293T cells were then loaded with FAP-1 by incubating with 10 µM FAP-1 in BSS (diluted from 10 mM stock in DMSO) for 30 minutes at 37° C. The buffer was then replaced with 500 µL fresh BSS containing no probe (for FA addition experiment, the buffer was instead replaced with 500 µL BSS containing 1 mM FA followed by 30 min incubation), and the cells were imaged using a Zeiss laser scanning microscope 710 with a 63× oil-immersion objective lens using Zen 2009 software (Carl Zeiss). FAP-1 was excited using a 633 nm HeNe laser, and emission was collected using a META detector between 638 to 747 nm. ER-Tracker Green, BODIPY FL $C_5$-Ceramide, LysoTracker Green DND-26, and MitoTracker Green FM were excited using a 488 nm Ar laser, and emission was collected using a META detector between 500 and 600 nm. Hoechst 33342 was excited with a 405 nm diode laser, and emission was collected using a META detector between 450 and 500 nm.

Figure 23A:
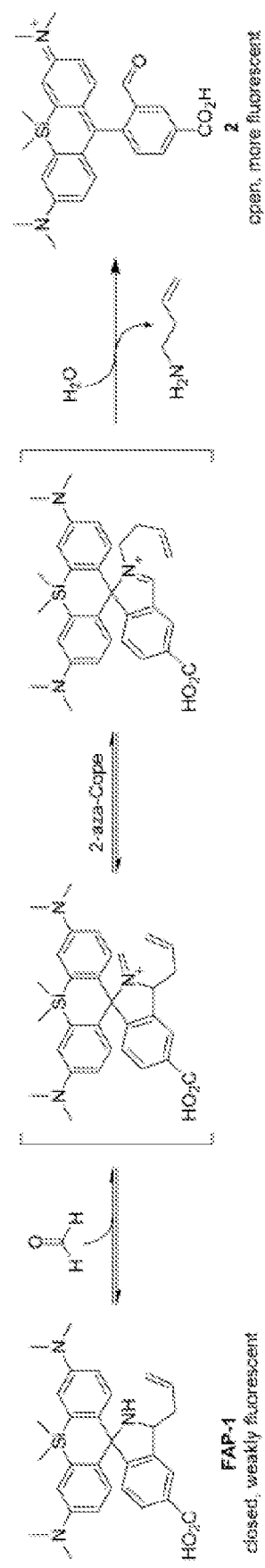
FIG. 23A-23B depict schematics for FIG. 23A, design of formaldehyde probe FAP-1 and FIG. 23B, synthesis of formaldehyde probe FAP-1. $^a$Reagents and conditions: (i) Boc$_2$O, DMAP, THF, $^t$BuOH, 70° C., 12 h; (ii) NBS, AIBN, PhCF$_3$, 115° C., 8 h; (iii) AgNO$_3$, H$_2$O, MeCN, 70° C., 24 h; (iv) NH$_3$, MeOH, 0° C., then allylboronic acid pinacol ester, rt, 10 h; (v) Boc$_2$O, THF, rt, 14 h; (vi) PhLi, THF, −78° C., then $^t$BuLi, THF, −78° C., then 7, −78° C. to rt, 3 h; (vii) TFA:DCM, 1:1, rt, 12 h.
Figure 23B:
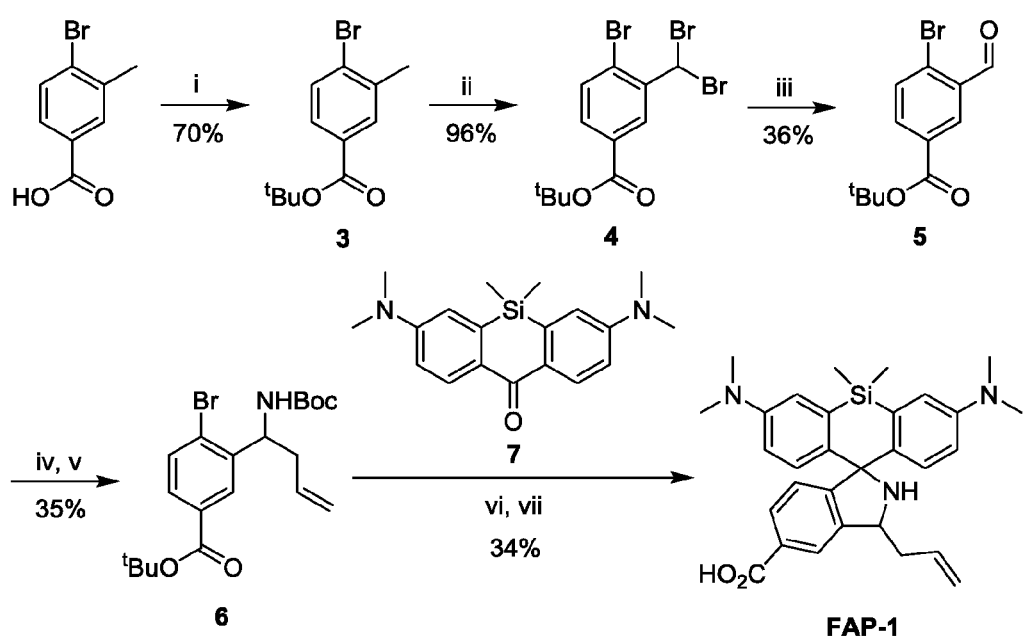

Example 2: An Aza-Cope Reactivity-Based Fluorescent Probe for Imaging Formaldehyde in Living Cells Reactivity-based fluorescence detection for transient small-molecule analytes, including carbonyl species such as CO (Wang et al., *Angew. Chem.* 2012, 124:9790-9794; Michel et al., *J. Am. Chem. Soc.* 2012, 134:15668-15671; Zheng et al., *Chem. Sci.* 2014, 5:3439-3448; Chaves-Ferreira et al., *Angew. Chem. Int. Ed.* 2015, 54:1172-1175; Wilson et al., *Chem. Eur. J.* 2014, 20:14698-14704) and methylglyoxal (Wang et al., *J. Am. Chem. Soc.* 2013, 135: 12429-12433), have previously been exploited, and this general approach was applied to FA detection. The present design exploits an FA-induced 2-aza-Cope reaction to trans-form a homoallylic amine into an aldehyde coupled to a fluorogenic turn-on response. Indeed, previous attempts to monitor FA have relied on formimine formation (Song et al., *Tetrahedron Lett.* 2012, 53:4913-4916; Zhou et al., *Sens. Actuators, B.* 2015, 209:664-669); however, this condensation tends to have an unfavorable equilibrium constant in water, leading to difficulty in detecting low concentrations of the RCS. It was reasoned that an aza-Cope rearrangement could trap the imine and lead to accumulation of a fluorescent product after hydrolysis (FIG. 23A). Inspired by the work of Urano, Nagano, and co-workers that aminomethyl silicon rhodamine dyes are weakly emissive at physiologically-relevant pH due to spirocyclization (Uno et al., *Nat. Chem.* 2014, 6:681-689; Lukinavicius and Johnsson, *Nat. Chem.* 2014, 6:663-664), FAP-1 was designed with a homoallylamine that would favor ring closure and low fluorescence. Upon reaction with FA, imine formation and subsequent 2-aza-Cope rearrangement and hydrolysis yielded an aldehyde product that is incapable of spirocyclization would give a fluorescence turn-on. Spirocyclization-based strategies have been employed fruitfully to detect a wide variety of biological analytes (Chen et al., *Chem. Rev.* 2012, 112:1910-1956; Grimm et al., *ACS Chem. Biol.* 2013, 8:1303-1310). FAP-1 was synthesized in 7 steps, utilizing a key boronate-mediated aminoallylation to install the reactive trigger (FIG. 23B).

Figure 25:
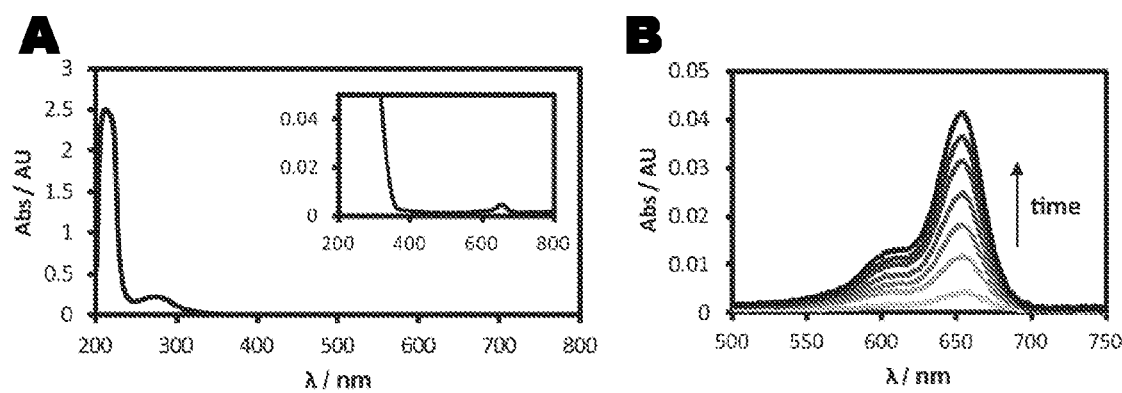
FIG. 25 depicts the UV-visible spectra of FAP-1. Data were acquired in 20 mM PBS (pH 7.4) with 10 μM FAP-1. (a) UV-visible spectrum of FAP-1 with magnified inset. (b) UV-visible response of 10 μM FAP-1 to 100 μM FA. Time points represent 0, 20, 40, 60, 80, 100, and 120 (black trace) minutes after addition of 100 μM FA; saturation was not reached during this time.
Figure 26A:
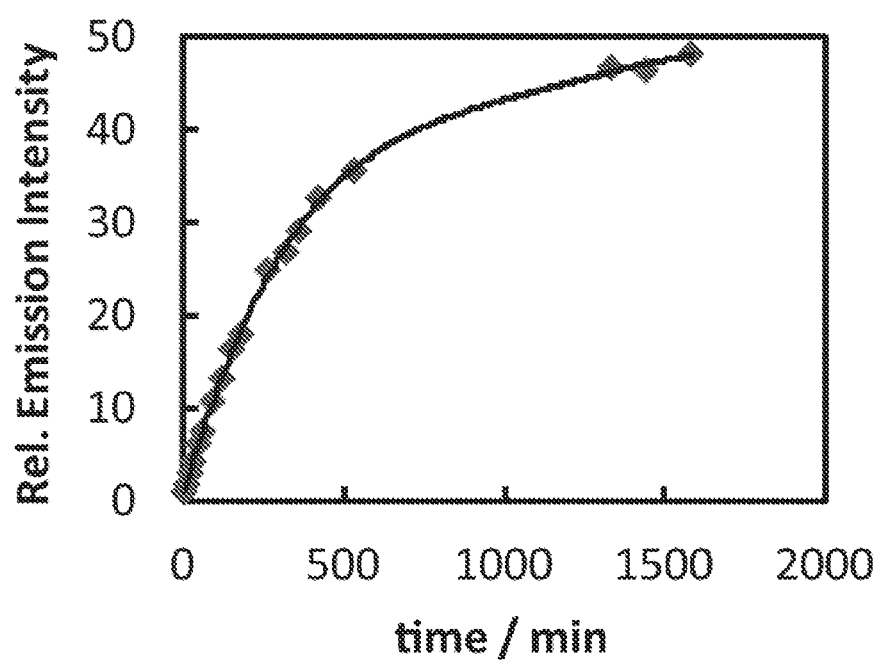
FIG. 26A depicts the turn-on saturation of 10 μM FAP-1 to 100 μM FA. Data were acquired at 37° C. in 20 mM PBS (pH 7.4) with excitation at $\lambda_e$=645 nm. Emission was collected between 655 and 750 nm.
Figure 26B:
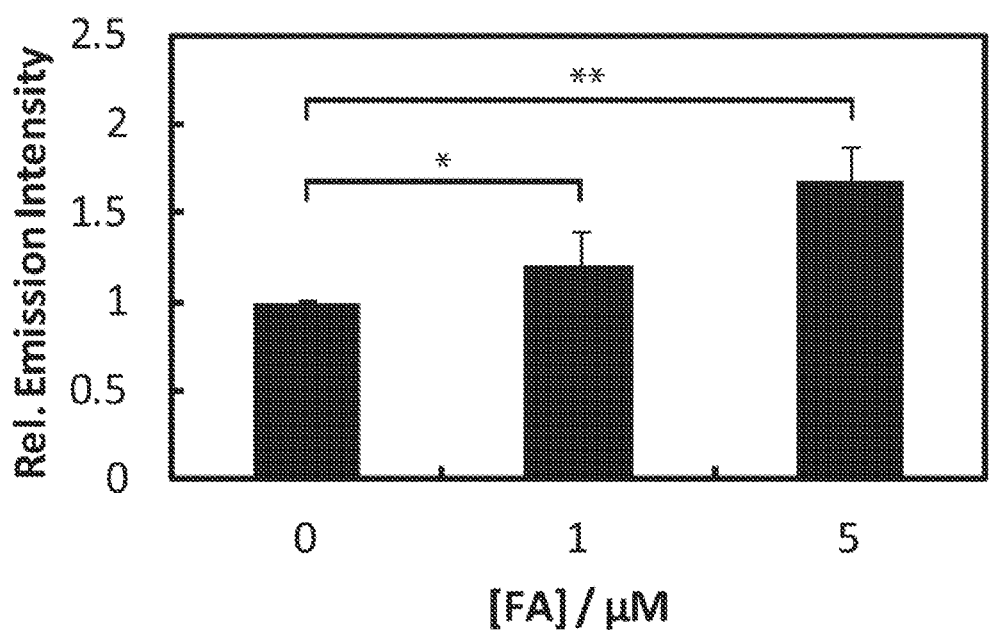
FIG. 26B depicts the fluorescence response of 10 μM FAP-1 to low concentrations of FA. Data were acquired in 20 mM PBS (pH 7.4) at 37° C. with excitation at $\lambda_e$=645 nm. Bars represent relative emission from 655-700 nm 2 hours after addition. Statistical analyses for multiple comparisons were performed using one-way ANOVA with the Bonferroni correction in the statistical analysis software, R. Values are shown as mean±standard deviation (n=3). *P>0.01, **P<0.01.
Figure 27:
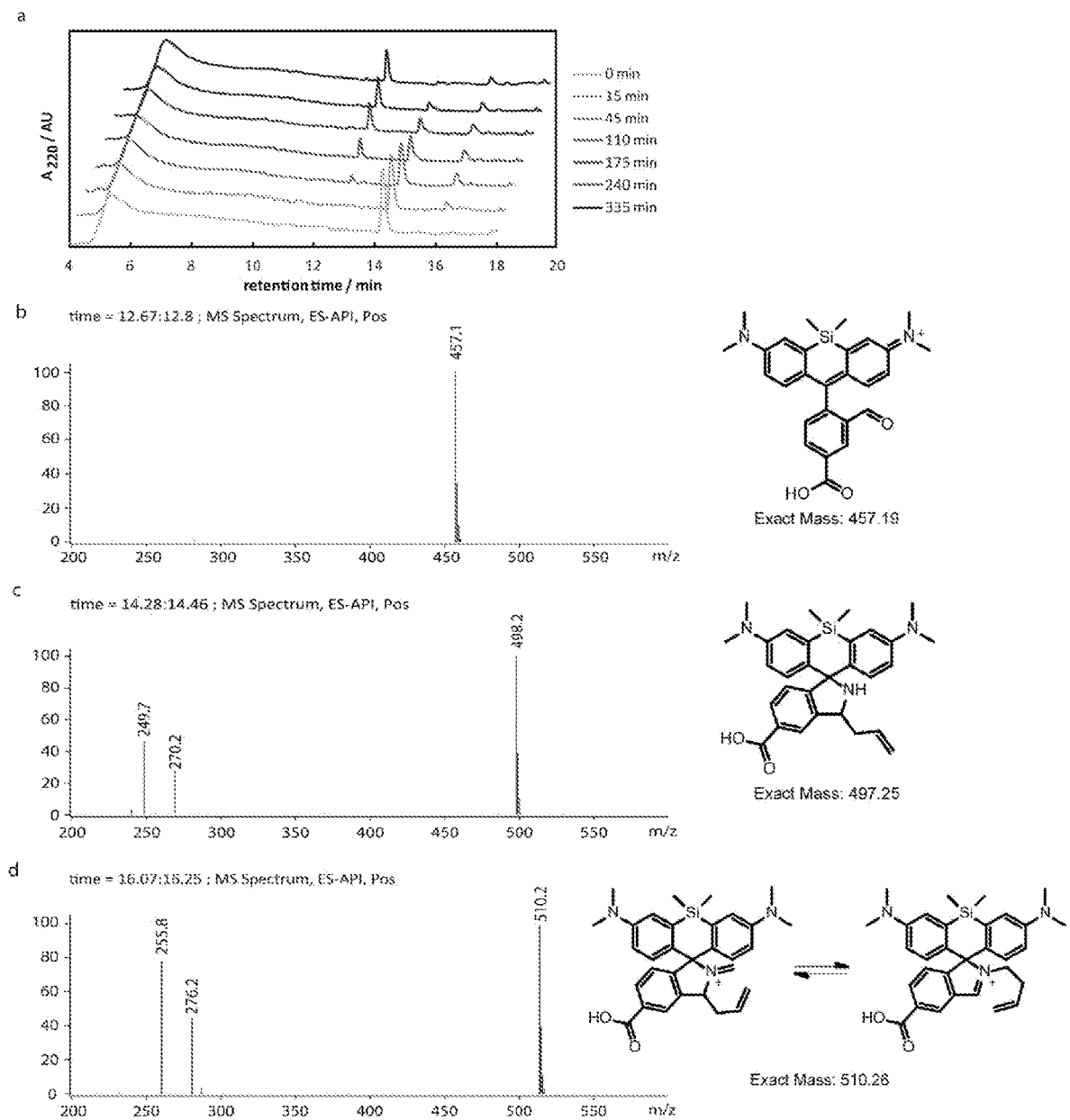
FIG. 27 depicts the LC-MS timecourse of reaction between 100 μM FAP-1 and 1 mM FA at 25° C. in 20 mM PBS (pH 7.4). HPLC runs used a linear gradient from 5% MeCN/95% H$_2$O/0.05% formic acid to 95% MeCN/5% H$_2$O/0.05% formic acid over 16 min using an Agilent 300extend-C18, 3.5 μm, 4.6×100 mm column. (a) Reversephase HPLC profile at 220 nm at different timepoints during reaction. Mass spectra of peaks eluting at (b) 12.7 min, (c) 14.3 min, and (d) 16.1 min during gradient.

With FAP-1 in hand, its fluorescence turn-on response to FA in aqueous solution buffered to pH 7.4, in which it shows good solubility (log $D_{oct/wat}$=0.53±0.01) was tested. FAP-1 was weakly fluorescent ($\varepsilon_{650}$=190 M$^{-1}$ cm$^{-1}$, $\varphi_{fl}$=0.36; FIG. 25) and exhibited a ca. 8-fold fluorescence turn-on response ($\lambda_{max}$=645 nm, $\lambda_{em}$=662 nm) upon treatment with 100 μM FA, a physiological concentration of this RCS, within 1 h (FIG. 24A) (Heck et al., *AIHA J.* 1985, 46:1-3; Andersen et al., *Toxicol. Sci.* 2010, 118:716-731). This fluorescence enhancement is likely due to the increase in absorptivity observed during FA treatment (FIG. 25B). At extended incubation times, the turn-on response saturates at ca. 45-fold (FIG. 26A). At a 10 μM FAP-1 concentration and a 2-hour cutoff, the in vitro detection limit for FA was found to be 5 μM (FIG. 26B). To verify that the observed fluorescence turn-on response was the result of the proposed 2-aza-Cope reaction, the reaction between FAP-1 and FA was monitored by LC-MS, which showed clean conversion from FAP-1 to a product with the expected mass of aldehyde (FIG. 27).

Figure 24B:
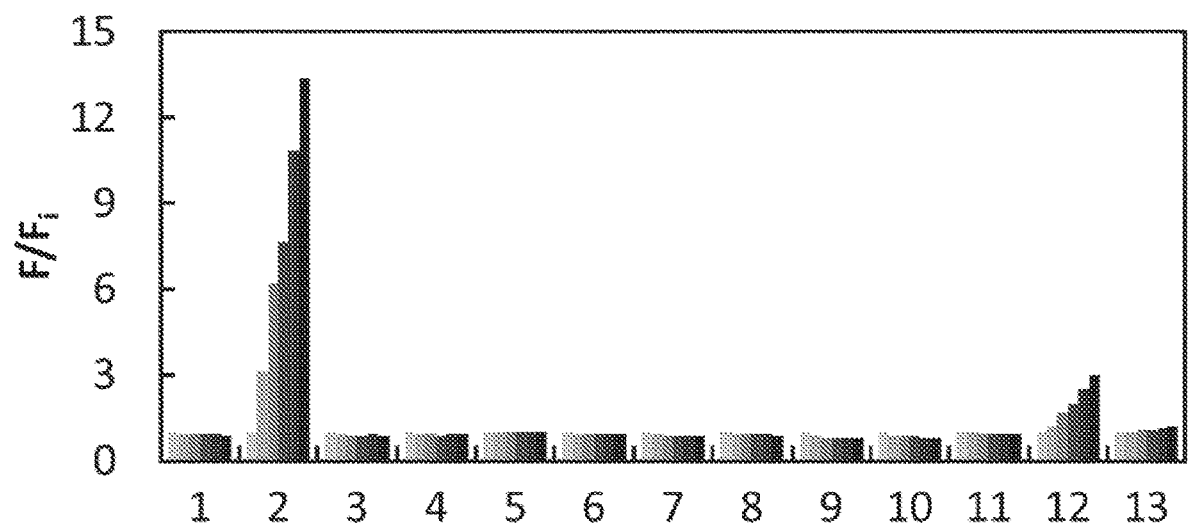

FAP-1 shows good selectivity for FA over potentially competing biological RCS, including 4-hydroxynonenal, dehydroascorbate, glucosone, oxaloacetate, and methylglyoxal, as well as over simple carbonyl-containing molecules including acetaldehyde, pyruvate, and glucose (FIG. 24B). FAP-1 is not responsive to 10 μM methylglyoxal, which is above its single-digit micromolar physiological range (Kalapos, *Diabetes Res. Gin. Pract.* 2013, 99:260-271), but does show a small response to super-physiological levels (100 μM) of this RCS. In addition, exposure of FAP-1 to oxidizing and reducing conditions that could be encountered in the cell-specifically, 100 μM $H_2O_2$ and 5 mM glutathione resulted in no change in fluorescence (FIG. 24B).

Figure 28A:
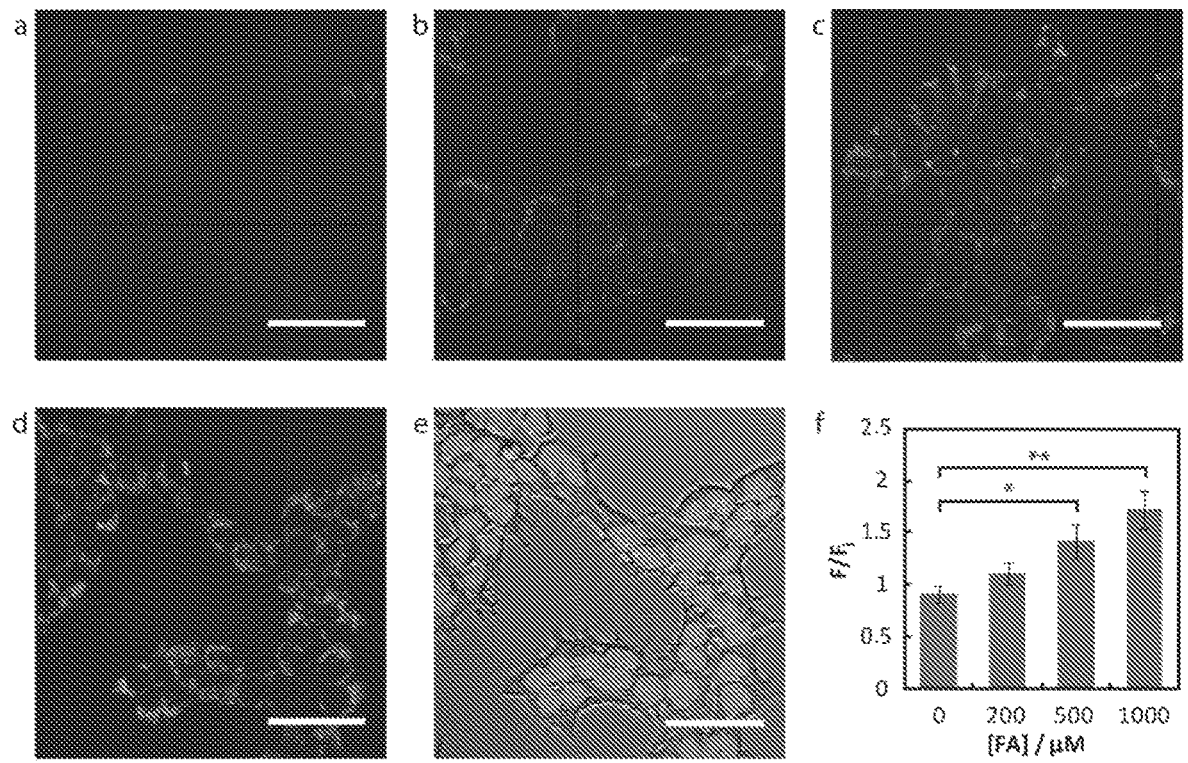
Figure 29:
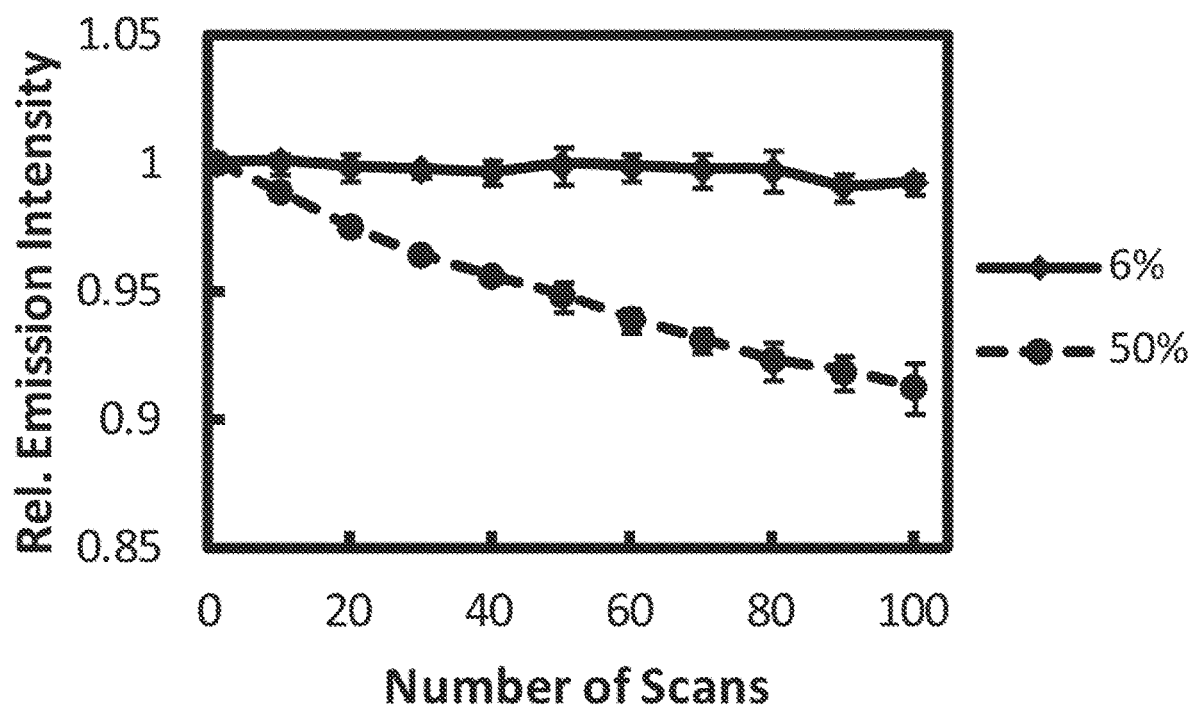
FIG. 29 depicts a photostability study with FAP-1. A field of HEK293T cells loaded with 10 μM FAP-1 in BSS at 37° C. was irradiated using 50% laser power (dashed line) or 6% laser power (solid line) with a pinhole of 1 airy unit for 100 scans. Emission was normalized to the first scan for each field. Error bars represent standard deviation, n=5.
Figure 30:
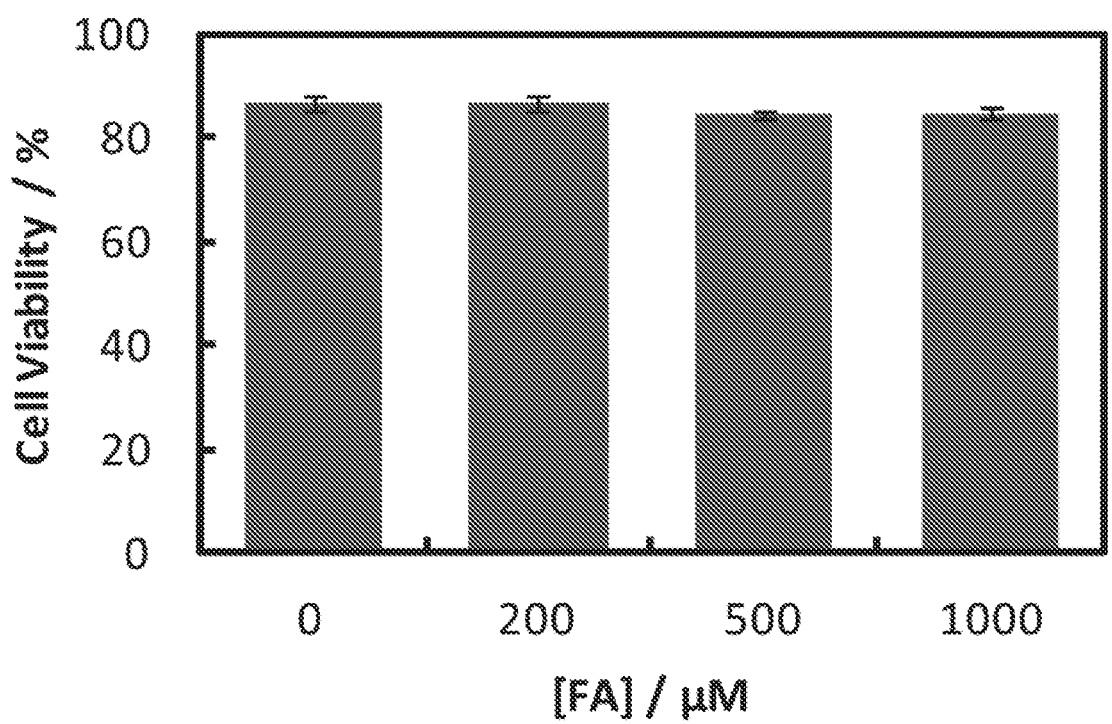
FIG. 30 depicts flow cytometric analysis of cell viability using propidium iodide (PI) staining. Cells were plated in 12-well polystyrene culture plates (Corning). After the designated treatments below, cells were dislodged from wells by gentle agitation and filtered through 35 μm nylon mesh cap into a 12×75 mm polystyrene tube (Corning) for flow cytometry. Cell viability was calculated as the percentage of PI-negative cells.
Figure 30:
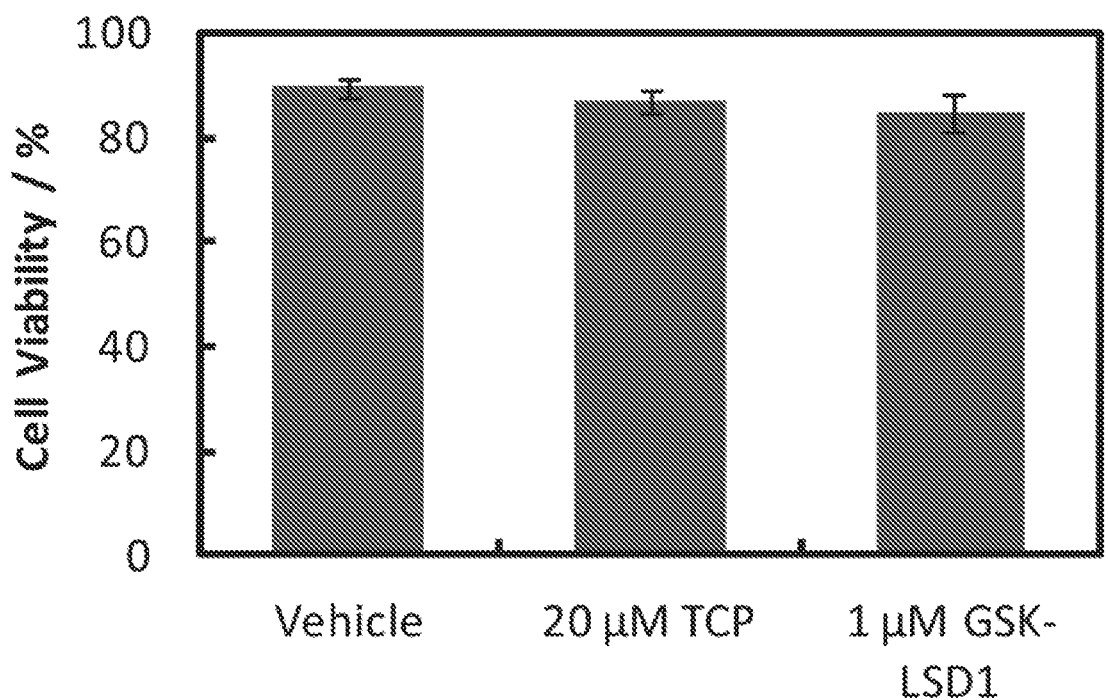
Figure 31:
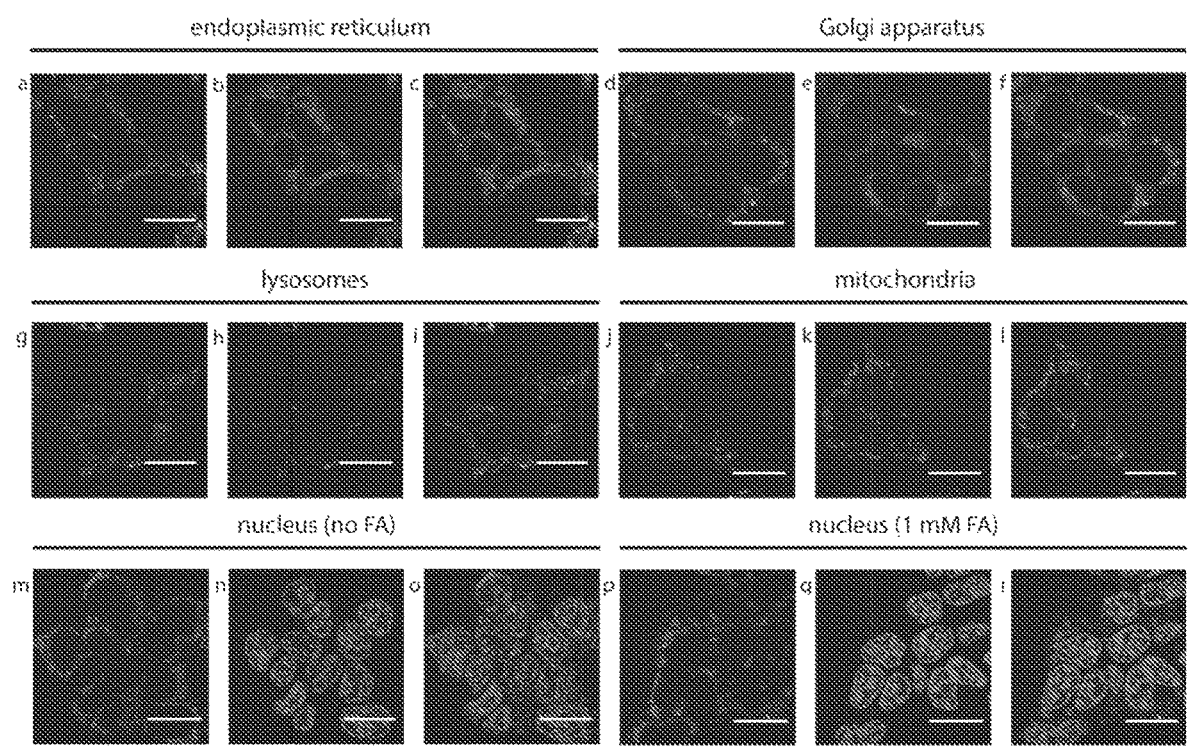
FIG. 31 depicts colocalization studies with FAP1 in HEK293T cells. Endoplasmic reticulum: (a) FAP-1 (red), (b) ER-Tracker Green (green), (c) merge of (a) and (b). Golgi apparatus: (d) FAP-1 (red), (e) BODIPY FL C$_5$-Ceramide (green), (f) merge of (d) and (e). Lysosomes: (g) FAP-1 (red), (h) LysoTracker Green DND-26 (green), (i) merge of (g) and (h). Mitochondria: (j) FAP-1 (red), (k) MitoTracker Green FM (green), (l) merge of (j) and (k). Nuclei: (m) FAP-1 (red), (n) Hoechst 33342 (blue), (o) merge of (m) and (n). Nuclei after treatment of HEK293T cells with 1 mM FA for 30 min: (p) FAP-1 (red), (q) Hoechst 33342 (blue), (r) merge of (p) and (q). Scale bar represents 20 μm in all images.

Having established that the 2-aza-Cope-based trigger of FAP-1 can selectively detect FA in solution at physiological levels, its ability to visualize changes in FA in living cells using confocal microscopy was evaluated (FIG. 28A). Treatment of HEK293T cells with 10 μM FAP-1 for 30 min followed by washing to remove excess probe and addition of various concentrations of FA (200 μM to 1 mM) showed a significant and dose-dependent fluorescence turn-on in FA-treated cells over control cells (FIG. 28A (panels a-d, f)), demonstrating the ability of FAP-1 to detect FA in a cellular context. Notably, these FA concentrations fall well within a physiological concentration range, which is estimated at ca. 100 μM in blood (Heck et al., *AIHA J.* 1985, 46:1-3), 400 μM intracellularly (Andersen et al., *Toxicol. Sci.* 2010, 118:716-731), and up to 700-800 μM in several cancer tissues (Tong et al., *PLoS ONE.* 2010, 5:e10234). To rule out the possibility of photoactivation and/or photobleaching interfering with fluorescence intensity measurements, photostability studies in HEK293T cells were performed. FAP-1 exhibited consistent fluorescence intensity during 100 scans with 6% laser power (used for all imaging experiments), but exhibits slight photobleaching at 50% laser power (FIG. 29). Moreover, cell viability was verified using Hoechst 33342 staining, which clearly showed intact and viable nuclei (FIG. 28A panel e), as well as a propidium iodide assay, which indicated no difference between FA-treated and untreated cells (FIG. 30A). To further probe the cellular distribution of FAP-1, colocalization studies using commercial organelle-targeted dyes were performed. FAP-1 was found to be excluded from the nucleus (FIG. 31 panels m-r, FIG. 32), but showed overlap with endoplasmic reticulum-, Golgi apparatus-, lysosome-, and mitochondria-targeted dyes (FIG. 31 panels a-1, FIG. 32). In addition, the distribution of FAP-1 was not appreciably affected by the addition of 1 mM FA (FIG. 31 panels p-r).

Figure 28B:
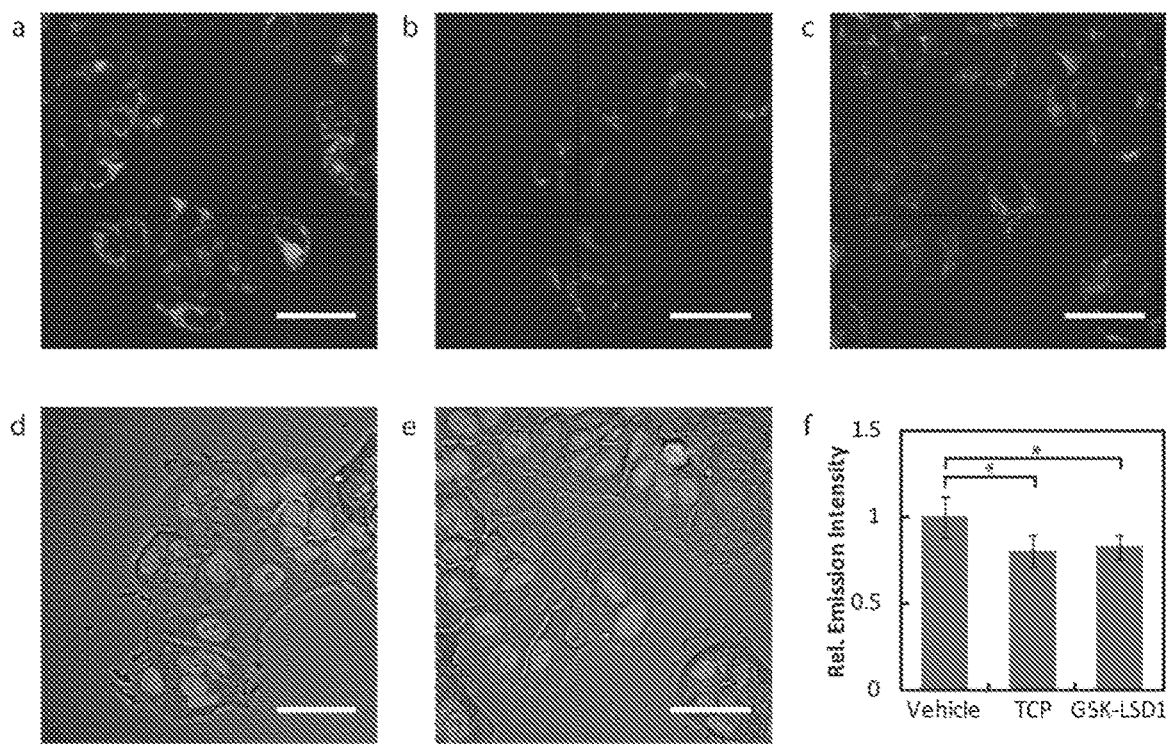

Next, it was tested whether FAP-1 could be applied to image endogenous FA levels in a disease model. Specifically, elevated FA levels in certain cancers have been attributed to overexpression of LSD1, where pharmacological inhibition of LSD1 can lead to an observable decrease in FA (Mei et al., *PLoS ONE.* 2013, 8:e58957). To determine whether FAP-1 was able to visualize changes in endogenously-produced FA, the MCF7 human breast cancer cell line that is known to overexpress LSD1 was used (Lim et al., *Carcinogenesis.* 2009, 31:512-520). Upon treatment of MCF7 cells with 20 μM tranylcypromine (TCP), an LSD1 inhibitor with an IC50 of 2 μM (Lee et al., *Chem. Biol.* 2006, 13:563-567), a ca. 20% decrease in FAP-1 fluorescence signal compared to control cells was observed. Additionally, treatment with 1 μM GSK-LSD1, a more potent LSD-1 inhibitor (IC50 of 42 nM) (Ortega Munoz, et al., U.S. Patent Application No. 2015/0025054), also attenuated FAP-1 fluorescence (FIG. 28B). Taken together, the data show that FAP-1 is capable of detecting endogenously-produced FA in a disease model.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A formaldehyde probe of the formula:

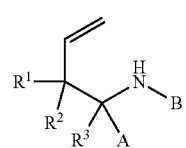

wherein:

R¹, R², R³, and B are each independently selected from the group consisting of hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy and an amido; and wherein A is a fluorophore, wherein the fluorophore is attached to the formula via a bond directly to a cyclic group in the fluorophore; or A is of the formula:

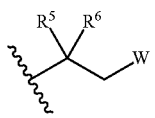

wherein W comprises a fluorophore; and

R⁵ and R⁶ are independently selected from the group consisting of hydrogen, an alkyl, a substituted alkyl, an aryl, a substituted aryl, a heteroaryl, a substituted heteroaryl, a halogen, a cyano, an azido, an alkoxy, a substituted alkoxy, a hydroxyl, a carboxy and an amido; or A and B are cyclically linked; and wherein B comprises a quencher that is in energy-receiving proximity to the fluorophore.

2. The probe of claim 1, wherein the probe has the formula:

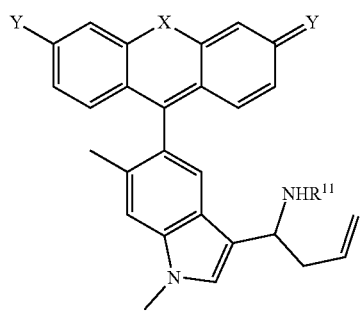

wherein:

X is selected from the group consisting of O, SiR₂, CR₂, SnR₂, BF₂, S, Se, Te, PO₂H, AsO₂H, wherein each R is independently H or an alkyl (e.g., methyl);

each Y is independently selected from =O, —OH, —NH₂, =NH, —NR'R", =N⁺R'R", wherein R' and R" are independently an alkyl or a substituted alkyl, or R' and R" are cyclically linked to form, with the N to which they are attached, a five or six-membered heterocycle or substituted heterocycle; and R¹¹ is selected from the group consisting of hydrogen, alkyl, substituted alkyl, alkoxy, substituted alkoxy, aralkyl, substituted aralkyl, aryl, substituted aryl, heteroaryl and substituted heteroaryl, and wherein R¹¹ comprises the quencher.

3. A formaldehyde probe of the formula:

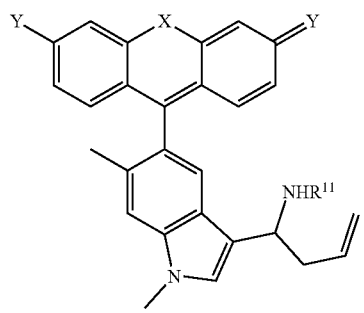

wherein:

each Y is independently selected from one of the following structures:

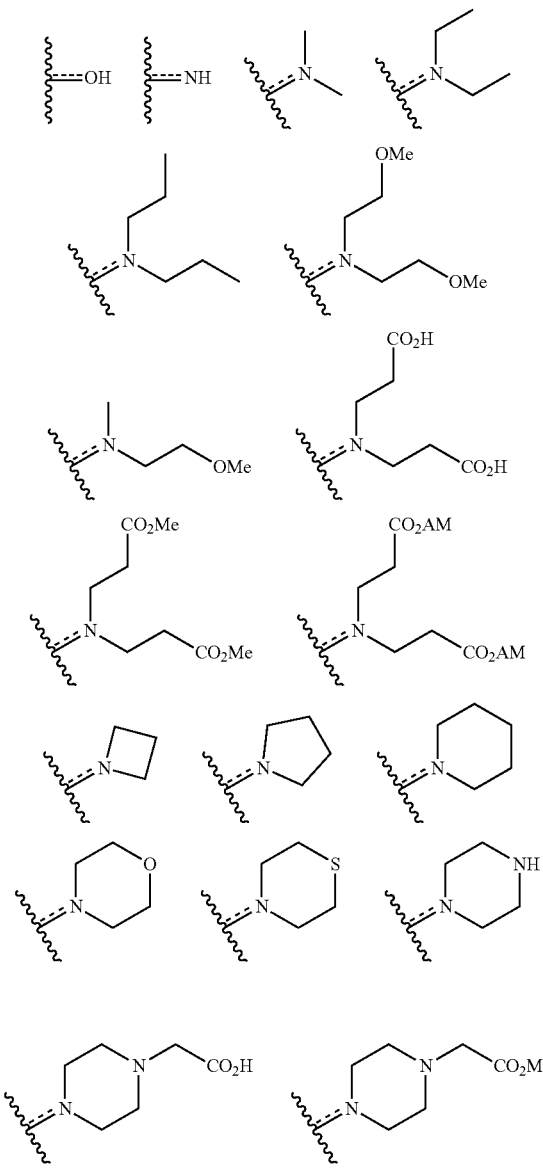

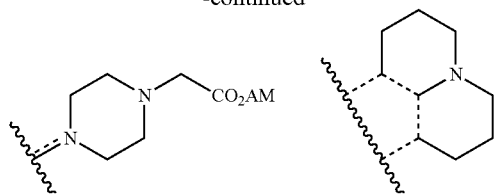

wherein when Y is connected to the probe via a double bond, it can be positively charged; and $R^{11}$ is selected from one of the following structures:

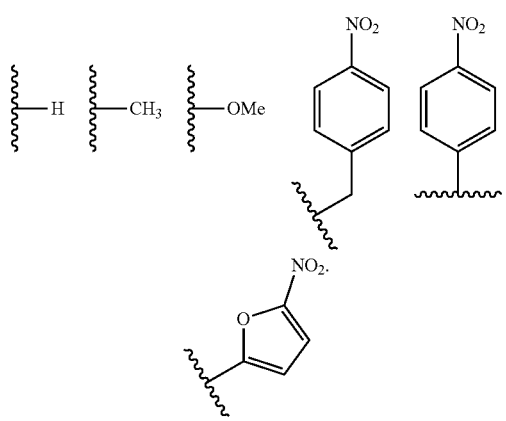

4. A formaldehyde probe of the formula:

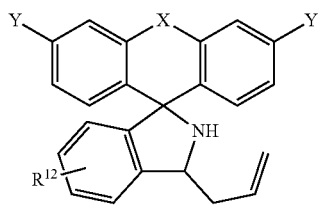

wherein:
X is selected from the group consisting of O, $SiR_2$, $CR_2$, $SnR_2$, $BF_2$, S, Se, Te, $PO_2H$, $AsO_2H$, wherein each R is independently H or an alkyl;
each Y is independently selected from =O, —OH, —$NH_2$, =NH, —NR'R", =$N^+$R'R", wherein R' and R" are independently an alkyl or a substituted alkyl, or R' and R" are cyclically linked to form, with the N to which they are attached, a five or six membered heterocycle or substituted heterocycle; and
$R^{12}$ is hydrogen, carboxy, an ester, an amido, an alkyl-amido or a substituted alkyl-amido, wherein $R^{12}$ optionally comprises a chemoselective tag.

5. The probe of claim 4, wherein:
each Y is independently selected from one of the following structures:

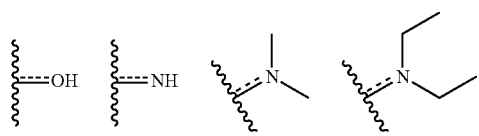

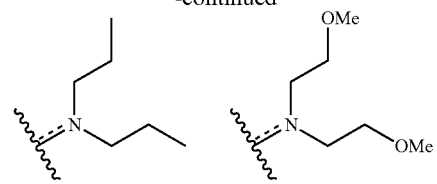

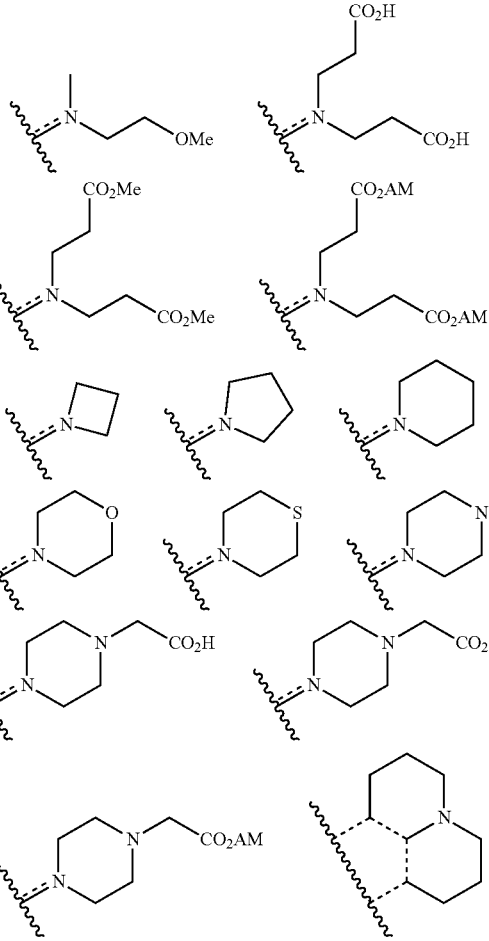

wherein when Y is connected to the probe via a double bond, it can be positively charged; and $R^{12}$ is selected from one of the following structures:

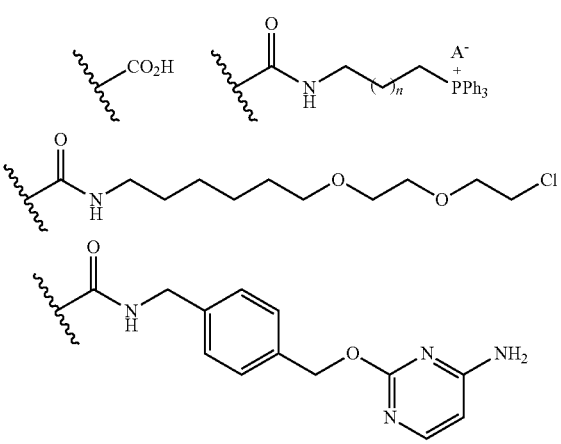

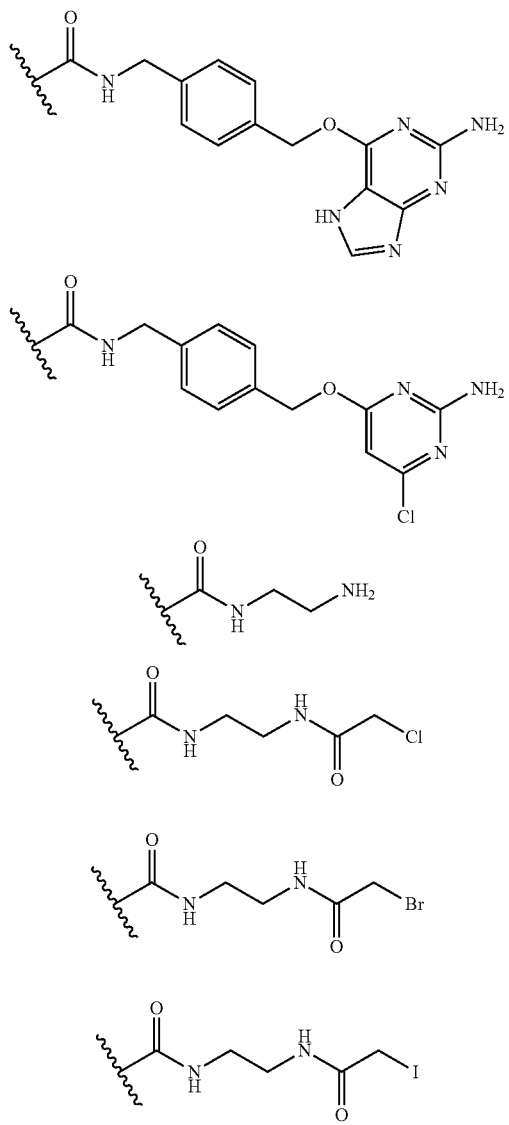

wherein n is 0, 1, 2, 3, 4, 5 or 6; and A⁻ is a counteranion.

6. The probe of claim 1, wherein A has the formula:

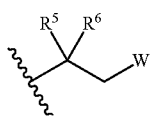

wherein W comprises a fluorophore selected from the group consisting of a xanthene dye, a xanthene analog, a fluorescein dye, and a rhodamine dye; and $R^5$ and $R^6$ are independently selected from the group consisting of hydrogen, an alkyl, a substituted alkyl, an aryl, a substituted aryl, a heteroaryl, a substituted heteroaryl, a halogen, a cyano, an azido, an alkoxy, a substituted alkoxy, a hydroxyl, a carboxy and an amido.

7. The probe of claim 1, wherein the probe has one of the following formulae:

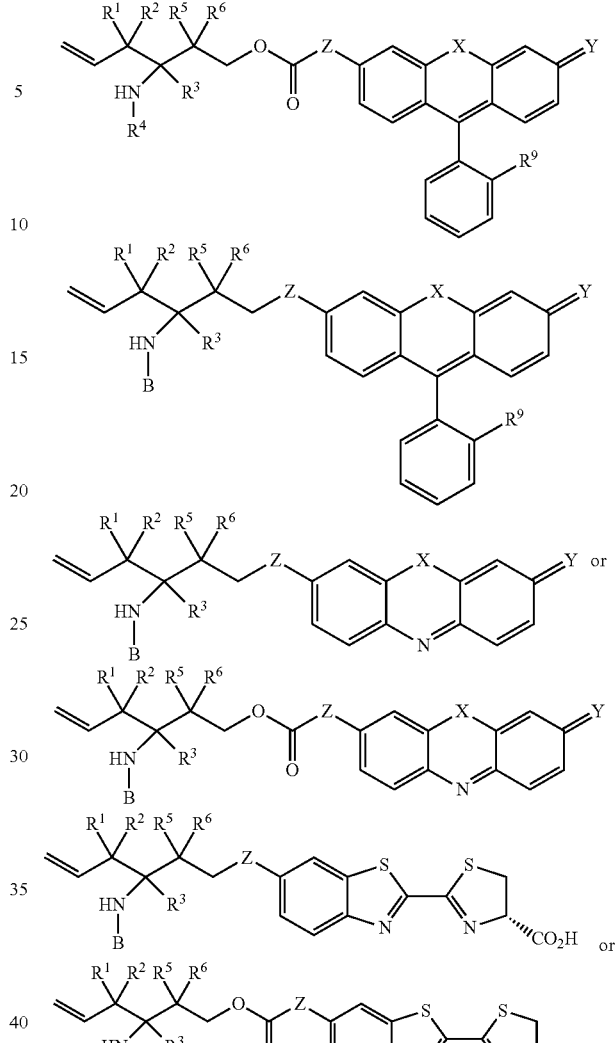

wherein:

Z is O, S, NH or NR' wherein R' is an alkyl or substituted alkyl;

$R^9$ is selected from the group consisting of hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy, a carboxy ester, and an amido; and X, Y, and B are as defined in claim 1.

8. A formaldehyde probe of one of the following structures:

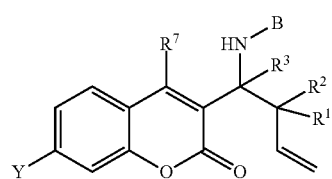

-continued

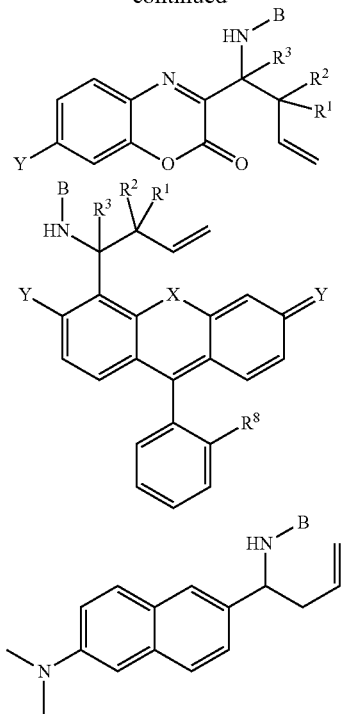

wherein:
R¹-R³ and Y are as defined above;
R⁷ and R⁸ are independently selected from the group consisting of hydrogen, an alkyl, a substituted alkyl, an aryl, a substituted aryl, a heterocycle, a substituted heterocycle, a heteroaryl, a substituted heteroaryl, a halogen, a cyano, an azido, an alkoxy, a substituted alkoxy, a hydroxyl, a carboxy, a carboxy ester and an amido; and
B is selected from the group consisting of hydrogen, alkyl, substituted alkyl, hydroxy, alkoxy, substituted alkoxy, aryl, substituted aryl, aralkyl, substituted aralkyl, heterarylalkyl, and substituted heterarylalkyl.

9. The probe of claim 8, wherein:
each Y is independently selected from one of the following structures:

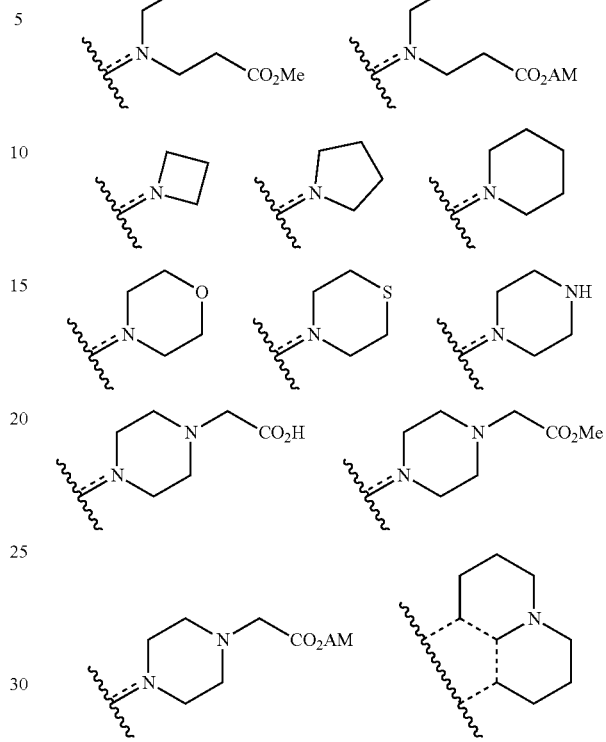

-continued

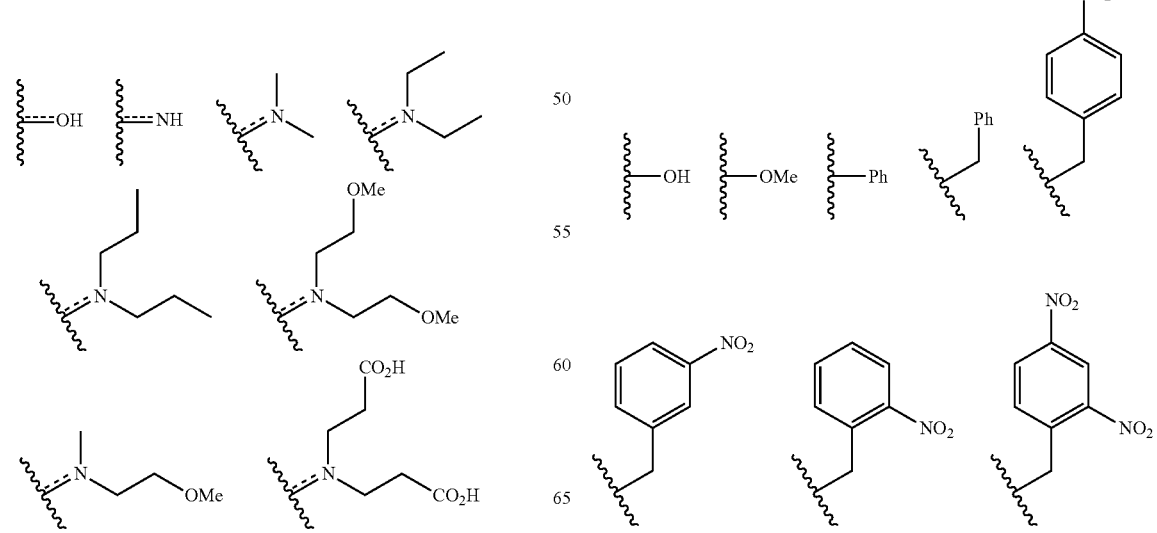

wherein when Y is connected to the probe via a double bond, it can be positively charged;

B is selected from one of the following structures:

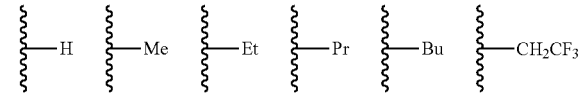

-continued

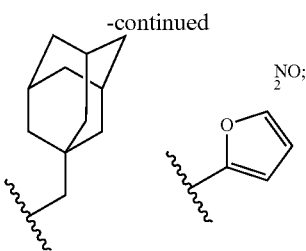

and $R^1$, $R^2$, $R^3$, $R^7$ and $R^8$ are independently selected from one of the following structures:

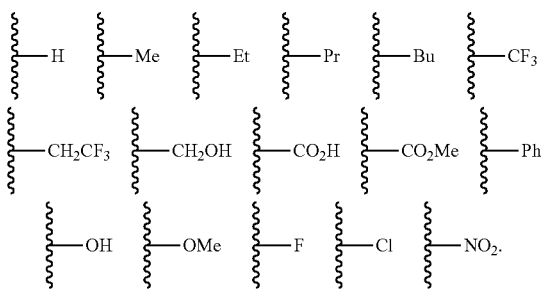

10. A method of detecting formaldehyde in a sample, the method comprising (a) contacting a sample comprising formaldehyde with a probe of claim 1, 3, 4, or 8, thereby selectively reacting the probe with the formaldehyde in the sample to release a reporter group comprising a detectable moiety; and (b) detecting the detectable moiety thereby providing for detection of the formaldehyde in the sample.

11. The method of claim 10, wherein the detecting comprises fluorescently imaging the sample.

12. The method of claim 10, further comprising analyzing the level of formaldehyde in the sample.

13. The method of claim 10, further comprising analyzing the activity of an enzyme endogenous to the sample.

14. The method of claim 10, wherein the sample is a biological sample comprising a cell, a cell lysate, a tissue, or a fluid.

15. The method of claim 10, wherein the sample is a biological sample that is in vivo.

16. A method of detecting formaldehyde in a cell, tissue, organ or fluid in a living subject, the method comprising:

(a) administering to the subject a probe of claim 1, 3, 4, or 8, thereby selectively reacting the probe with the formaldehyde in the sample to release a reporter group comprising a detectable moiety; and (b) detecting the detectable moiety in the cell, tissue, organ or fluid, thereby providing for detection of the formaldehyde.

17. The method of claim 16, wherein the cell, tissue, or organ is a diseased cell, tissue, or organ.

* * * * *